US011725212B2

(12) United States Patent
Grimon et al.

(10) Patent No.: US 11,725,212 B2
(45) Date of Patent: Aug. 15, 2023

(54) POLYNUCLEOTIDE SHUFFLING METHOD

(71) Applicants: Universiteit Gent, Ghent (BE); Katholieke Universiteit Leuven, Leuven (BE)

(72) Inventors: Dennis Grimon, Ghent (BE); Hans Gerstmans, Merksem (BE); Yves Briers, Nederokkerzeel (BE); Rob Lavigne, Ekeren (BE)

(73) Assignees: Universiteit Gent, Ghent (BE); Katholieke Universiteit Leuven, Leuven (BE)

( * ) Notice: Subject to any disclaimer, the term of this patent is extended or adjusted under 35 U.S.C. 154(b) by 218 days.

(21) Appl. No.: 16/471,078

(22) PCT Filed: Dec. 19, 2017

(86) PCT No.: PCT/EP2017/083596
§ 371 (c)(1),
(2) Date: Jun. 19, 2019

(87) PCT Pub. No.: WO2018/144980
PCT Pub. Date: Jun. 28, 2018

(65) Prior Publication Data

US 2019/0323017 A1 Oct. 24, 2019

(30) Foreign Application Priority Data

Dec. 19, 2016 (GB) ..................................... 1621589

(51) Int. Cl.
*C12N 15/66* (2006.01)

(52) U.S. Cl.
CPC .......... *C12N 15/66* (2013.01); *C12N 2330/30* (2013.01); *C12N 2800/80* (2013.01); *C12Q 2523/313* (2013.01)

(58) Field of Classification Search
None
See application file for complete search history.

(56) References Cited

U.S. PATENT DOCUMENTS

2014/0329233 A1 11/2014 Minshull

OTHER PUBLICATIONS

Engler et al., "A One Pot, One Step, Precision Cloning Method with High Throughput Capability," PLoS ONE 2008, 3(11):e3647. (Year: 2008).*

(Continued)

*Primary Examiner* — Kaijiang Zhang
(74) *Attorney, Agent, or Firm* — Dinsmore & Shohl LLP

(57) ABSTRACT

It is a first object of the present invention to provide a method for preparing a Tile vector, being a vector, which comprises a selectable marker and a coding polynucleotide, wherein said coding polynucleotide is immediately preceded and followed by a type IIs recognition sequence, wherein said preceding and following recognition sequences are recognized by a same type IIs restriction enzyme, but have an opposite orientation. More particularly, the position and orientation of said preceding and following type IIs recognition sequences provides for the cleavage of said Tile vector by a corresponding type IIs restriction enzyme resulting in the release of said coding polynucleotide sequence having at its respective ends overhang sequences with a known orientation and length, while lacking said preceding and following type IIs recognition sequences.
In a second object the present invention provides a method for using such Tile vectors obtained as previously described for joining two or more coding polynucleotides to form a product polynucleotide. Typically, said product polynucleotide is integrated in a vector.

9 Claims, 19 Drawing Sheets

Figure 1:
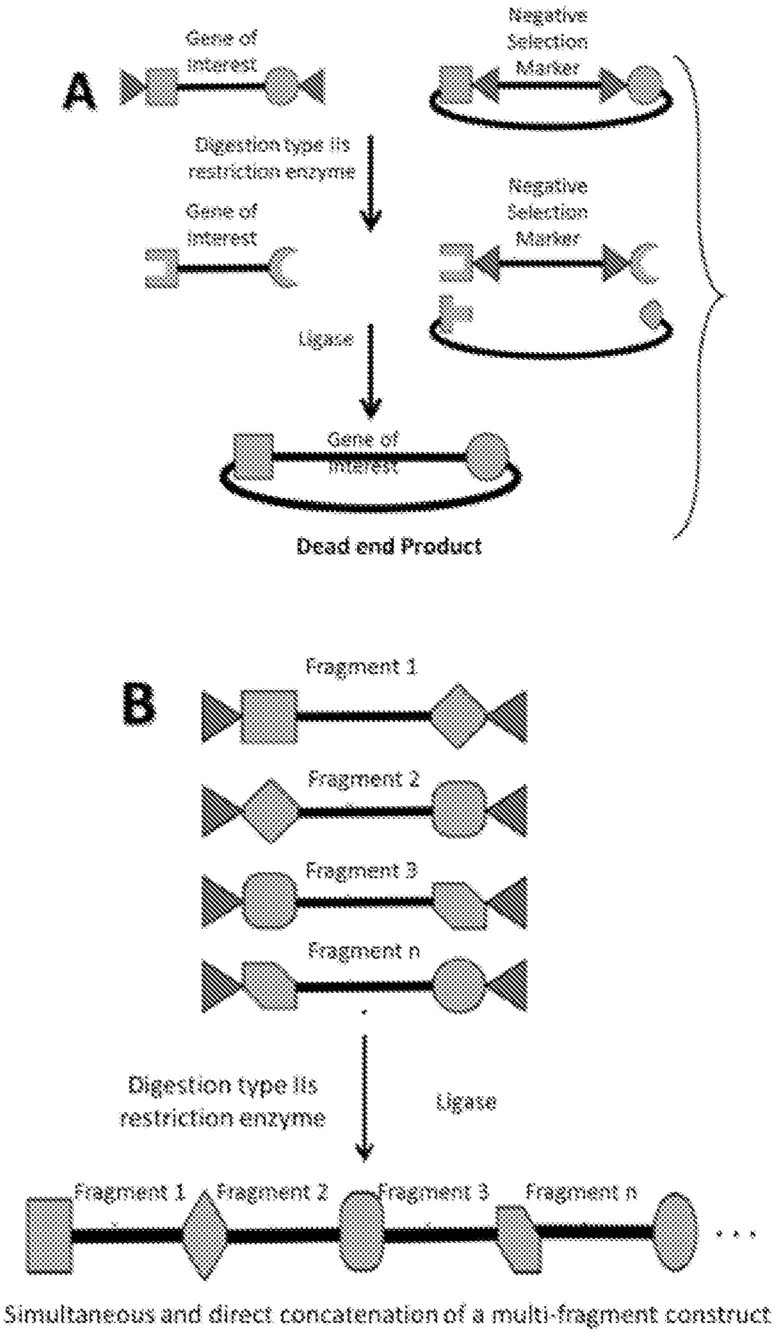

Specification includes a Sequence Listing.

(56) References Cited

OTHER PUBLICATIONS

European Patent Office Search report dated Mar. 19, 2018, in reference to co-pending European Patent Applicatior No. PCT/EP2017/083596 filed Dec. 19, 2017.
Lee, et al., "Sequential amplification of cloned DNA as tandem multimers using class-IIS restriction enzymes", Genetic Analysis: Biomolecular Engineering, Els ev i er Science Publishing, us, vol. 13. No. 6, Dec. 1, 1996 (Dec. 1, 1996), pp. 139-145, XP004017262.
Veerle, et al., "Synthetic biology of modular proteins", Bioengineered, vol. 8, No. 3, Sep. 20, 2016 (Sep. 20, 2016), pp. 196-202, XP002778834.
Villiers, et al., "USER friendly DNA recombination (USERec): a simple and flexible near homology-independent method for gene library construction", Protein Engineering, Design and Selection, Oxford Journal, London, GB, vo 1 • 23, No. 1, Jan. 1, 2010 (Jan. 1, 2010), pp. 1-8, XP002608544.
Benkovi c, et al., "A combinatorial approach to hybrid enzymes independent of DNA homology", Nature Biotechnology (Advance Online Publication), vol. 17, No. 12, Dec. 1, 1999 (Dec. 1, 1999), pp. 1205-1209, XP55456937.
Won, et al., "A New Cloning Method for the Preparation of Long Repetitive Polypeptides without a Sequence Requirement", Macromolecules, vol. 1 • 35, No. 22, Oct. 1, 2002 (Oct. 1, 2002), pp. 8281-8287, XP055065185.
Vad-Nielson, et al., "Golden Gate Assembly of CRISPR gRNA expression array for simultaneously targeting multiple genes", Cellular and Molecular Life Sciences, pp. 4315-4325, 2016.
O'Mallie, et al., "Structure-based Combinatorial Protein Engineering (SCOPE)", J. Mol. Biology, pp. 677-691, 2002.
Ostermeier, et al., "A combinatorial approach to hybrid enzymes independent of DNA homology", Nature America Inc., vol. 17, pp. 1205-1209, Dec. 1999.
Weber, et al., "A Modular Cloning System for Standardized Assembly of Multigene Constructs", PLos One, vol. 6, Issue 2, pp. 1-11, Feb. 18, 2011.
Lutz, et al., "Homology-independent protein engineering", Protein technologies and commercial enzymes, pp. 319-324, 2000.
Kawarasaki, et al., "Enhanced crossover SCRATCHY: construction and high-throughput screening of a combinatorial library containing multiple non-homologous crossovers", Nucleic Acids Research, vol. 31, No. 21, Jun. 11, 2003.
Lutz, "Beyond directed evolution-semi-rational protein engineering and design", ScienceDirect, pp. 734-743, 2010.
Patrick, et al., "ITCHY: Incremental Truncation for the Creation of Hybrid Enzymes", Methods in Molecular Biology, Chapter 16, pp. 225-244, 2014.
Sarrion-Perdigones, et al., "GoldenBraid: An Iterative Cloning System for Standardized Assembly of Reusable Genetic Modules", PLosone, vol. 6, Issue 7, Jul. 2011.
Sieber, et al., "Libraries of hybrid proteins from distantly related sequences", Nature Publishing Group, vol. 19, pp. 456-460, May 2001.

* cited by examiner

A.

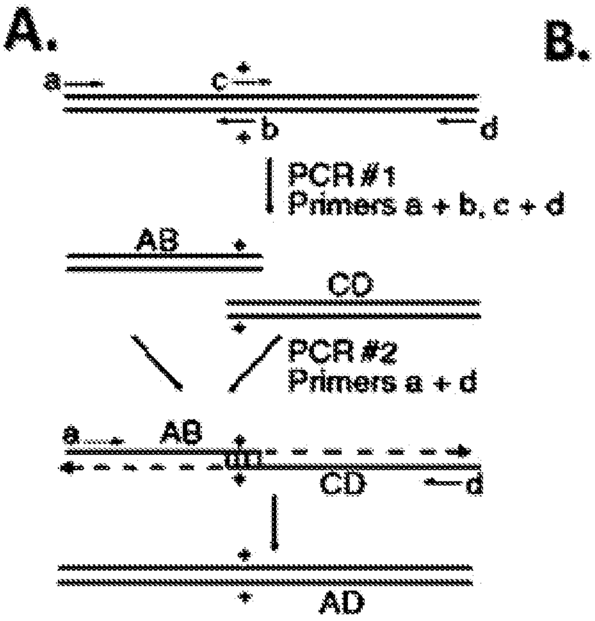

B.

| Temperature | Time |
|---|---|
| 98°C | 30sec |
| 98°C | 10sec |
| 58°C | 30sec |
| 72°C | 25sec |
| 98°C | 10sec |
| 56°C | 30sec |
| 72°C | 25sec |
| 98°C | 10sec |
| 54°C | 30sec |
| 72°C | 25sec |
| 98°C | 10sec |
| 52°C | 30sec |
| 72°C | 25sec |
| 98°C | 10sec |
| Tm + 3°C | 30sec |
| 72°C | 50sec |
| 72°C | 5min |

X 26

C.

| | EAD 10 | |
|---|---|---|
| Primer a | TACGACATTGCGTGGAG | (SEQ ID N°34) |
| Primer b | CTGAATGTCTGGCCGGTTTCAAAAGCCATACAGGC | (SEQ ID N°35) |
| Primer c | GCCTGTATGGCTTTTGAAACCGGCCAGACATTCAG | (SEQ ID N°36) |
| Primer d | ATACGAAATAACGTGACGATTTTCAG | (SEQ ID N°37) |

| | EAD 16 | |
|---|---|---|
| Primer a | AAAAGCCCCGCTTATCC | (SEQ ID N°38) |
| Primer b | CGCTCGAACAGGATCGATACCTGGCCATCGTCCTGG | (SEQ ID N°39) |
| Primer c | CCAGGACGATGGCCAGGTATCGATCCTGTTCGAGCG | (SEQ ID N°40) |
| Primer d | CGACCCGCCCCCGAAC | (SEQ ID N°41) |

FIG. 2

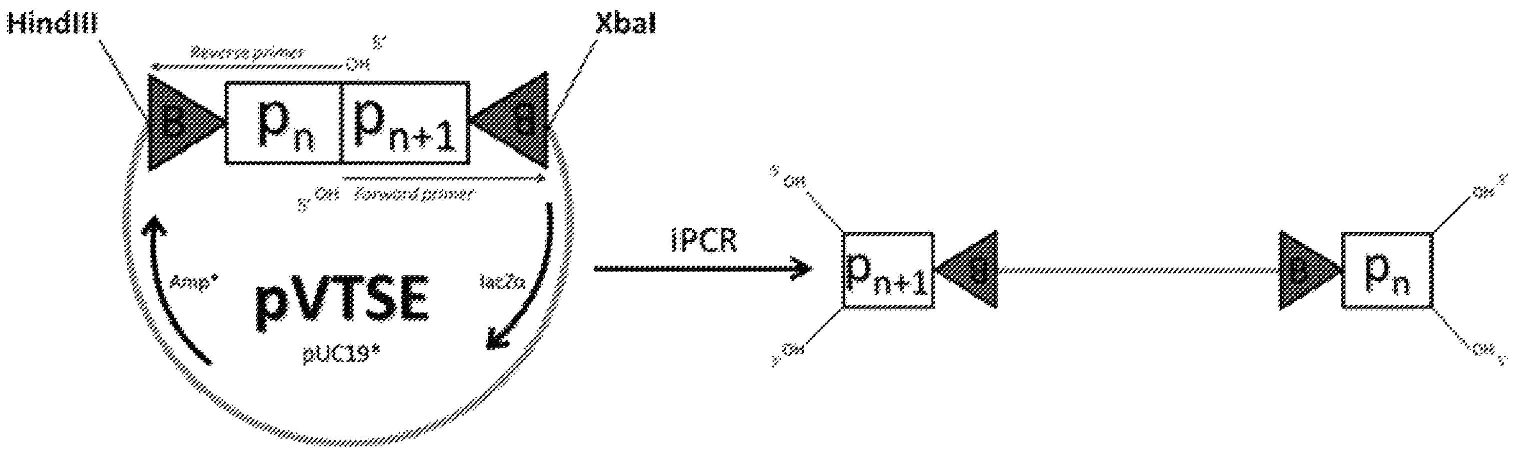
| Position marker | Nucleotide sequence | Amino acid sequence |
|---|---|---|
| $P_1$ | ACCATG | T-START(M) |
| $P_2$ | GGTGCA | G-A |
| $P_3$ | GCAGGT | A-G |
| $P_4$ | GGAAGC | G-S |
| $P_5$ | AAGTAG | L-STOP |
| BsaI recognition site | Nucleotide sequence |
|---|---|
| 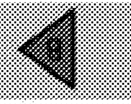 | GAGACC |
| 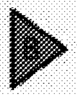 | GGTCTC |
FIG. 3

Table 1: Overview used coding extension sequences

| | Tile position | Preceding coding extension sequence (3xn) | Following coding extension sequence (3xn) | Final coding extension sequence after assembly (preceding Tile) | Final coding extension sequence after assembly (following Tile) | Amino acid extension sequence preceding Tile | Amino acid extension sequence following on Tile |
|---|---|---|---|---|---|---|---|
| **Experi-mental setup 1** | 1 | NCCATG | GGTGCN | ACCATG | GGTGCT | -/START | Gly/Ala |
| | 2 | NGTGCT | GCAGGN | GGTGCT | GCAGGC | Gly/Ala | Ala/Gly |
| | 3 | NCAGGC | GGAAGN | GCAGGC | GGAAGC | Ala/Gly | Gly/Ser |
| | 4 | NGAAGC | AAGTAN | GGAAGC | AAGTA(A/C) | Gly/Ser | Lys/Stop or Tyr |
| **Experi-mental setup 2** | 1 | NCCATG | AGCACN | ACCATG | AGCACA | -/START | Ser/Thr |
| | 2 | NGCACA | CCAACN | AGCACA | CCAACG | Ser/Thr | Pro/Thr |
| | 3 | NCAACG | ACGAGN | CCAACG | ACGAGC | Pro/Thr | Thr/Ser |
| | 4 | NCGAGC | CCGTCN | ACGAGC | CCGTCT | Thr/Ser | Pro/Ser |
| | 5 | NCGTCT | AAGTAN | CCGTCT | AAGTA(A/C) | Pro/Ser | Lys/Stop or Tyr |
| **Experi-mental setup 3** | 1 | NCCATG | TCTGGN | ACCATG | TCTGGT | -/START | Ser/Gly |
| | 2 | NCTGGT | GGTTCN | TCTGGT | GGTTCA | Ser/Gly | Gly/Ser |
| | 3 | NGTTCA | AAGTAN | GGTTCA | AAGTA(A/C) | Gly/Ser | Lys/Stop or Tyr |

[1] (A/C) the respective nucleotide that is added depends on the destination vector used (P1 destination vector = ACCATN; Pn+1 destination vector = NAGTAA if destination vector has a lysin (Lys) and stop codon immediately following on the product nucleotide or = NAGTAC if destination vector has a lysin (Lys) and tyrosine (Tyr) immediately following on the product nucleotide. The latter destination vectors add a C-terminal sequence such a purification tag to the protein

[2] N : This nucleotide can be chosen freely for the generation of Tiles. This will be removed during assembly

FIG. 17

Table 3: Overview Blunt end ligation reaction mix.

| **Component** | **Amount** |
|---|---|
| pVTSE | 1 µL (50 ng) |
| Insert | 1 µL (3:1 molar ratio over vector) |
| 10x T4 DNA ligase buffer | 2 µL |
| T4 DNA ligase (5 U/µL) | 1 µL |
| 50% PEG 4000 | 2 µL |
| Add mQ up to a total volume of 20 µL | |

FIG. 18

Table 4: Reaction mixture and composition VTS reaction

| **Reaction mixture** | | **Temperature program** | | |
|---|---|---|---|---|
| 100ng | pVTSEII/III | 2min | 37°C | X30 |
| 50ng | Tile | 3min | 16°C | |
| 1µL | type IIs restriction enzyme | 5min | 50°C | |
| 3µL | T4 DNA ligase (1U) | 5min | 80°C | |
| 2µL | T4 DNA ligase buffer | | | |
| Add mQ to 20µL | | | | |

FIG. 19

Table 8: 2-step PCR protocol for Tile amplification with reduced primer dimer formation

| Step | Temperature (°C) | Time | Number of cycles |
|---|---|---|---|
| Initial denaturation | 98 | 30 s | 1 |
| Denaturation | 98 | 10 s | 10 |
| Annealing | TA1 | 25 s | |
| Extension | 72 | 30 s/kb | |
| Denaturation | 98 | 10 s | 20 |
| Annealing | TA2 | 25 s | |
| Extension | 72 | 30 s/kb | |
| Final extension | 72 | 10 min | 1 |

**TA1 annealing temperature initial coding polynucleotide overlap*
**TA2 annealing temperature initial coding polynucleotide and terminal sequence overlap*

FIG. 20

Table 9: Optimized of the VersaTile Shuffling protocol for rational assembly

| VersaTile Shuffling reaction mix | | Temperature | Time | Cycles |
|---|---|---|---|---|
| pVTSDx | 1 µL (100 ng) | 37°C | 2min | 10 |
| Each tile (plasmid/PCR) | 1 µL (50 ng) | 16°C | 3min | |
| BsaI | 1 µL (10U) | 50°C | 5min | 1 |
| T4 DNA ligase | 1 µL (1U) | 8°C | 5min | 1 |
| 10x ligation buffer | 2 µL | | | |
| Add ultrapure water up to a total volume 20 µL | | | | |

FIG. 21

Table 10: Optimized protocol for semi-random and random assembly

| VersaTile reaction mix | | Temperature | time | cycles |
|---|---|---|---|---|
| pVTSDx | 1 µL (100 ng) | 37°C | 2min | 50 |
| Each tile (plasmid/PCR) | 1 µL (50 ng) | 16°C | 3min | |
| BsaI | 1 µL (10U) | 50°C | 5min | 1 |
| T4 DNA ligase | 1 µL (1U) | 8°C | 5min | 1 |
| 10x ligation buffer | 2 µL | | | |
| Add ultrapure water up to a total volume 20 µL | | | | |

FIG. 22

Table 11: Composition VersaTile reaction mix

| VersaTile reaction mix | |
|---|---|
| pVTSDx | 1 µL (100 ng) |
| Each tile (plasmid/PCR) | 1 µL (50 ng) |
| BsaI | 1 µL (10U) |
| T4 DNA ligase | 3 µL (3U) |
| 10x ligation buffer | 2 µL |
| Add mQ up to a total volume 20 µL | |

FIG. 23

Table 12: Temperature program VersaTile shuffling

| VersaTile temperature program | |
|---|---|
| 37°C | 2 minutes |
| 16°C | 3 minutes |
| 50°C | 5 minutes |
| 80°C | 5 minutes |

X50

FIG. 24

Table 13: Error prone protocol. Initially 96µL of the master mix is taken and 2µL template DNA, 1µL Dreamtaq DNA polymerase and 1µL 50mM $MnCl_2$ is added. After ten cycles 10µL of the reaction mixture is taken and added to 90µL fresh master mix. This is repeated three times in order to increase the mutation ratio.

| **Component initial concentration** | **amount** | **Final concentration** | **PCR program** | | |
|---|---|---|---|---|---|
| dCTP 20mM | 15µL | 1mM | 94°C | 3 min | |
| dTTP 20mM | 15µL | 1mM | 94°C | 30sec | X10 |
| dATP 20mM | 3µL | 0.2mM | 50°C | 30sec | |
| dGTP 20mM | 3µL | 0.2mM | 72°C | 1.20min | |
| Forward primer 20µM | 15µL | 1µM | | | |
| Reverse Primer 20µM | 15µL | 1µM | | | |
| Dreamtaq buffer | 30µL | / | | | |
| $MgCl_2$ 1M | 1.5µL | 5mM | | | |
| mQ | 202.5µL | / | | | |

FIG. 25

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: pVTSE1 Forward Primer

<400> SEQUENCE: 1

ggtgctgaga cctctagagg                                                  20


<210> SEQ ID NO 2
<211> LENGTH: 20
<212> TYPE: DNA
<213> ORGANISM: Artificial Sequence
<220> FEATURE:
<223> OTHER INFORMATION: pVTSE1 Reverse Primer

<400> SEQUENCE: 2

catggtgaga ccaagcttgg                                                  20


<210> SEQ ID NO 3
<211> LENGTH: 20
<212> TYPE: DNA
<213> ORGANISM: Artificial Sequence
<220> FEATURE:
<223> OTHER INFORMATION: pVTSE2 Forward Primer

<400> SEQUENCE: 3

gcaggtgaga cctctagagg                                                  20


<210> SEQ ID NO 4
<211> LENGTH: 20
<212> TYPE: DNA
<213> ORGANISM: Artificial Sequence
```

<220> FEATURE:
<223> OTHER INFORMATION: pVTSE2 Reverse Primer

<400> SEQUENCE: 4
tgcactgaga ccaagcttgg 20

<210> SEQ ID NO 5
<211> LENGTH: 20
<212> TYPE: DNA
<213> ORGANISM: Artificial Sequence
<220> FEATURE:
<223> OTHER INFORMATION: pVTSE3 Forward Primer

<400> SEQUENCE: 5
ggaagcgaga cctctagagg 20

<210> SEQ ID NO 6
<211> LENGTH: 20
<212> TYPE: DNA
<213> ORGANISM: Artificial Sequence
<220> FEATURE:
<223> OTHER INFORMATION: pVTSE3 Reverse Primer

<400> SEQUENCE: 6
acctgtgaga ccaagcttgg 20

<210> SEQ ID NO 7
<211> LENGTH: 20
<212> TYPE: DNA
<213> ORGANISM: Artificial Sequence
<220> FEATURE:
<223> OTHER INFORMATION: pVTSE4 Forward Primer

<400> SEQUENCE: 7
aagtaggaga cctctagagg 20

<210> SEQ ID NO 8
<211> LENGTH: 20
<212> TYPE: DNA
<213> ORGANISM: Artificial Sequence
<220> FEATURE:
<223> OTHER INFORMATION: pVTSE4 Reverse Primer

<400> SEQUENCE: 8
gcttctgaga ccaagcttgg 20

<210> SEQ ID NO 9
<211> LENGTH: 3811
<212> TYPE: DNA
<213> ORGANISM: Artificial Sequence
<220> FEATURE:
<223> OTHER INFORMATION: pVTSEII Vector

<400> SEQUENCE: 9
agcttgacgt caggtggcac ttttcgggga aatgtgcgcg gaacccctat ttgtttattt 60
ttctaaatac attcaaatat gtatccgctc atgagacaat aaccctgata aatgcttcaa 120
taatattgaa aaaggaagag tatgagtatt caacatttcc gtgtcgccct tattcccttt 180
tttgcggcat tttgccttcc tgtttttgct cacccagaaa cgctggtgaa agtaaaagat 240
gctgaagatc agttgggtgc acgagtgggt tacatcgaac tggatctcaa cagcggtaag 300
atccttgaga gttttcgccc cgaagaacgt tttccaatga tgagcacttt taaagttctg 360
ctatgtggcg cggtattatc ccgtattgac gccgggcaag agcaactcgg tcgccgcata 420

```
cactattctc agaatgactt ggttgagtac tcaccagtca cagaaaagca tcttacggat    480
ggcatgacag taagagaatt atgcagtgct gccataacca tgagtgataa cactgcggcc    540
aacttacttc tgacaacgat cggaggaccg aaggagctaa ccgctttttt gcacaacatg    600
ggggatcatg taactcgcct tgatcgttgg gaaccggagc tgaatgaagc cataccaaac    660
gacgagcgtg acaccacgat gcctgtagca atggcaacaa cgttgcgcaa actattaact    720
ggcgaactac ttactctagc ttcccggcaa caattaatag actggatgga ggcggataaa    780
gttgcaggac cacttctgcg ctcggccctt ccggctggct ggtttattgc tgataaatct    840
ggagccggtg agcgtggttc tcgcggtatc attgcagcac tggggccaga tggtaagccc    900
tcccgtatcg tagttatcta cacgacgggg agtcaggcaa ctatggatga acgaaataga    960
cagatcgctg agataggtgc ctcactgatt aagcattggt aactgtcaga ccaagtttac   1020
tcatatatac tttagattga tttaaaactt catttttaat ttaaaaggat ctaggtgaag   1080
atcctttttg ataatctcat gaccaaaatc ccttaacgtg agttttcgtt ccactgagcg   1140
tcagaccccg tagaaaagat caaaggatct tcttgagatc ctttttttct gcgcgtaatc   1200
tgctgcttgc aaacaaaaaa accaccgcta ccagcggtgg tttgtttgcc ggatcaagag   1260
ctaccaactc tttttccgaa ggtaactggc ttcagcagag cgcagatacc aaatactgtt   1320
cttctagtgt agccgtagtt aggccaccac ttcaagaact ctgtagcacc gcctacatac   1380
ctcgctctgc taatcctgtt accagtggct gctgccagtg gcgataagtc gtgtcttacc   1440
gggttggact caagacgata gttaccggat aaggcgcagc ggtcgggctg aacggggggt   1500
tcgtgcacac agcccagctt ggagcgaacg acctacaccg aactgagata cctacagcgt   1560
gagctatgag aaagcgccac gcttcccgaa gggagaaagg cggacaggta tccggtaagc   1620
ggcagggtcg gaacaggaga gcgcacgagg gagcttccag ggggaaacgc ctggtatctt   1680
tatagtcctg tcgggtttcg ccacctctga cttgagcgtc gatttttgtg atgctcgtca   1740
ggggggcgga gcctatggaa aaacgccagc aacgcggcct ttttacggtt cctggccttt   1800
tgctggcctt ttgctcacat gttctttcct gcgttatccc ctgattctgt ggataaccgt   1860
attaccgcct ttgagtgtct agatagtctt cgacgtccac atatacctgc cgttcactat   1920
tatttagtga aatgagatat tatgatattt tctgaattgt gattaaaaag gcaactttat   1980
gcccatgcaa cagaaactat aaaaaataca gagaatgaaa agaaacagat agatttttta   2040
gttctttagg cccgtagtct gcaaatcctt ttatgatttt ctatcaaaca aaagaggaaa   2100
atagaccagt tgcaatccaa acgagagtct aatagaatga ggtcgaaaag taaatcgcgc   2160
gggtttgtta ctgataaagc aggcaagacc taaaatgtgt aaagggcaaa gtgtatactt   2220
tggcgtcacc ccttacatat tttaggtctt tttttattgt gcgtaactaa cttgccatct   2280
tcaaacagga gggctggaag aagcagaccg ctaacacagt acataaaaaa ggagacatga   2340
acgatgaaca tcaaaaagtt tgcaaaacaa gcaacagtat taacctttac taccgcactg   2400
ctggcaggag gcgcaactca agcgtttgcg aaagaaacga accaaaagcc atataaggaa   2460
acatacggca tttcccatat tacacgccat gatatgctgc aaatccctga acagcaaaaa   2520
aatgaaaaat ataaagttcc tgagttcgat tcgtccacaa ttaaaaatat ctcttctgca   2580
aaaggcctgg acgtttggga cagctggcca ttacaaaaca ctgacggcac tgtcgcaaac   2640
tatcacggct accacatcgt ctttgcatta gccggagatc ctaaaaatgc ggatgacaca   2700
tcgatttaca tgttctatca aaaagtcggc gaaacttcta ttgacagctg gaaaaacgct   2760
ggccgcgtct ttaaagacag cgacaaattc gatgcaaatg attctatcct aaaagaccaa   2820
```

acacaagaat ggtcaggttc agccacattt acatctgacg gaaaaatccg tttattctac 2880
actgatttct ccggtaaaca ttacggcaaa caaacactga caactgcaca agttaacgta 2940
tcagcatcag acagctcttt gaacatcaac ggtgtagagg attataaatc aatctttgac 3000
ggtgacggaa aaacgtatca aaatgtacag cagttcatcg atgaaggcaa ctacagctca 3060
ggcgacaacc atacgctgag agatcctcac tacgtagaag ataaaggcca caaatactta 3120
gtatttgaag caaacactgg aactgaagat ggctaccaag gcgaagaatc tttatttaac 3180
aaagcatact atggcaaaag cacatcattc ttccgtcaag aaagtcaaaa acttctgcaa 3240
agcgataaaa aacgcacggc tgagttagca aacggcgctc tcggtatgat tgagctaaac 3300
gatgattaca cactgaaaaa agtgatgaaa ccgctgattg catctaacac agtaacagat 3360
gaaattgaac gcgcgaacgt ctttaaaatg aacggcaaat ggtacctgtt cactgactcc 3420
cgcggatcaa aaatgacgat tgacggcatt acgtctaacg atatttacat gcttggttat 3480
gtttctaatt ctttaactgg cccatacaag ccgctgaaca aaactggcct tgtgttaaaa 3540
atggatcttg atcctaacga tgtaaccttt acttactcac acttcgctgt acctcaagcg 3600
aaaggaaaca atgtcgtgat tacaagctat atgacaaaca gaggattcta cgcagacaaa 3660
caatcaacgt ttgcgcctag cttcctgctg aacatcaaag gcaagaaaac atctgttgtc 3720
aaagacagca tccttgaaca aggacaatta acagttaaca aataaaaacg caaaagaaaa 3780
tgccgatatc ctattggcat tggaagacat a 3811

<210> SEQ ID NO 10
<211> LENGTH: 3877
<212> TYPE: DNA
<213> ORGANISM: Artificial Sequence
<220> FEATURE:
<223> OTHER INFORMATION: pVTSEIII Vector

<400> SEQUENCE: 10
gcgatgcgtc tcgactcctc gacgtcaggt ggcacttttc ggggaaatgt gcgcggaacc 60
cctatttgtt tatttttcta aatacattca aatatgtatc cgctcatgag acaataaccc 120
tgataaatgc ttcaataata ttgaaaaagg aagagtatga gtattcaaca tttccgtgtc 180
gcccttattc ccttttttgc ggcattttgc cttcctgttt ttgctcaccc agaaacgctg 240
gtgaaagtaa aagatgctga agatcagttg ggtgcacgag tgggttacat cgaactggat 300
ctcaacagcg gtaagatcct tgagagtttt cgccccgaag aacgttttcc aatgatgagc 360
acttttaaag ttctgctatg tggcgcggta ttatcccgta ttgacgccgg gcaagagcaa 420
ctcggtcgcc gcatacacta ttctcagaat gacttggttg agtactcacc agtcacagaa 480
aagcatctta cggatggcat gacagtaaga gaattatgca gtgctgccat aaccatgagt 540
gataacactg cggccaactt acttctgaca acgatcggag gaccgaagga gctaaccgct 600
tttttgcaca acatggggga tcatgtaact cgccttgatc gttgggaacc ggagctgaat 660
gaagccatac caaacgacga gcgtgacacc acgatgcctg tagcaatggc aacaacgttg 720
cgcaaactat taactggcga actacttact ctagcttccc ggcaacaatt aatagactgg 780
atggaggcgg ataaagttgc aggaccactt ctgcgctcgg cccttccggc tggctggttt 840
attgctgata aatctggagc cggtgagcgt ggttctcgcg gtatcattgc agcactgggg 900
ccagatggta agccctcccg tatcgtagtt atctacacga cggggagtca ggcaactatg 960
gatgaacgaa atagacagat cgctgagata ggtgcctcac tgattaagca ttggtaactg 1020

-continued

```
tcagaccaag tttactcata tatactttag attgatttaa aacttcattt ttaatttaaa   1080
aggatctagg tgaagatcct ttttgataat ctcatgacca aaatccctta acgtgagttt   1140
tcgttccact gagcgtcaga ccccgtagaa aagatcaaag gatcttcttg agatcctttt   1200
tttctgcgcg taatctgctg cttgcaaaca aaaaaaccac cgctaccagc ggtggtttgt   1260
ttgccggatc aagagctacc aactcttttt ccgaaggtaa ctggcttcag cagagcgcag   1320
ataccaaata ctgttcttct agtgtagccg tagttaggcc accacttcaa gaactctgta   1380
gcaccgccta catacctcgc tctgctaatc ctgttaccag tggctgctgc cagtggcgat   1440
aagtcgtgtc ttaccgggtt ggactcaaga cgatagttac cggataaggc gcagcggtcg   1500
ggctgaacgg ggggttcgtg cacacagccc agcttggagc gaacgaccta caccgaactg   1560
agatacctac agcgtgagct atgagaaagc gccacgcttc ccgaagggag aaaggcggac   1620
aggtatccgg taagcggcag ggtcggaaca ggagagcgca cgagggagct tccaggggga   1680
aacgcctggt atctttatag tcctgtcggg tttcgccacc tctgacttga gcgtcgattt   1740
ttgtgatgct cgtcaggggg gcggagccta tggaaaaacg ccagcaacgc ggccttttta   1800
cggttcctgg ccttttgctg gccttttgct cacatgttct ttcctgcgtt atcccctgat   1860
tctgtggata accgtattac cgcctttgag tggaggagtc gagacgcatc gctagatgaa   1920
gagcaggtta gatagtcttc gacgtccaca tatacgtgcc gttcactatt atttagtgaa   1980
atgagatatt atgatatttt ctgaattgtg attaaaaagg caactttatg cccatgcaac   2040
agaaactata aaaaatacag agaatgaaaa gaaacagata gattttttag ttctttaggc   2100
ccgtagtctg caaatccttt tatgattttc tatcaaacaa aagaggaaaa tagaccagtt   2160
gcaatccaaa cgagagtcta atagaatgag gtcgaaaagt aaatcgcgcg ggtttgttac   2220
tgataaagca ggcaagacct aaaatgtgta aagggcaaag tgtatacttt ggcgtcaccc   2280
cttacatatt ttaggtcttt ttttattgtg cgtaactaac ttgccatctt caaacaggag   2340
ggctggaaga agcagaccgc taacacagta cataaaaaag gagacatgaa cgatgaacat   2400
caaaaagttt gcaaaacaag caacagtatt aacctttact accgcactgc tggcaggagg   2460
cgcaactcaa gcgtttgcga aagaaacgaa ccaaaagcca tataaggaaa catacggcat   2520
ttcccatatt acacgccatg atatgctgca aatccctgaa cagcaaaaaa atgaaaaata   2580
taaagttcct gagttcgatt cgtccacaat taaaaatatc tcttctgcaa aggcctgga    2640
cgtttgggac agctggccat tacaaaacac tgacggcact gtcgcaaact atcacggcta   2700
ccacatcgtc tttgcattag ccggagatcc taaaaatgcg gatgacacat cgatttacat   2760
gttctatcaa aaagtcggcg aaacttctat tgacagctgg aaaaacgctg gccgcgtctt   2820
taaagacagc gacaaattcg atgcaaatga ttctatccta aaagaccaaa cacaagaatg   2880
gtcaggttca gccacattta catctgacgg aaaaatccgt ttattctaca ctgatttctc   2940
cggtaaacat tacggcaaac aaacactgac aactgcacaa gttaacgtat cagcatcaga   3000
cagctctttg aacatcaacg gtgtagagga ttataaatca atctttgacg gtgacggaaa   3060
aacgtatcaa aatgtacagc agttcatcga tgaaggcaac tacagctcag gcgacaacca   3120
tacgctgaga gatcctcact acgtagaaga taaaggccac aaatacttag tatttgaagc   3180
aaacactgga actgaagatg gctaccaagg cgaagaatct ttatttaaca aagcatacta   3240
tggcaaaagc acatcattct tccgtcaaga aagtcaaaaa cttctgcaaa gcgataaaaa   3300
acgcacggct gagttagcaa acggcgctct cggtatgatt gagctaaacg atgattacac   3360
actgaaaaaa gtgatgaaac cgctgattgc atctaacaca gtaacagatg aaattgaacg   3420
```

```
cgcgaacgtc tttaaaatga acggcaaatg gtacctgttc actgactccc gcggatcaaa   3480

aatgacgatt gacggcatta cgtctaacga tatttacatg cttggttatg tttctaattc   3540

tttaactggc ccatacaagc cgctgaacaa aactggcctt gtgttaaaaa tggatcttga   3600

tcctaacgat gtaaccttta cttactcaca cttcgctgta cctcaagcga aaggaaacaa   3660

tgtcgtgatt acaagctata tgacaaacag aggattctac gcagacaaac aatcaacgtt   3720

tgcgcctagc ttcctgctga acatcaaagg caagaaaaca tctgttgtca aagacagcat   3780

ccttgaacaa ggacaattaa cagttaacaa ataaaaacgc aaaagaaaat gccgatatcc   3840

tattggcatt ggaagacata agcacctgct cttctaa                            3877
```

<210> SEQ ID NO 11
<211> LENGTH: 5415
<212> TYPE: DNA
<213> ORGANISM: Artificial Sequence
<220> FEATURE:
<223> OTHER INFORMATION: pYVTSD Vector

<400> SEQUENCE: 11

```
ccaaagacga aaggttgaat gaaacctttt tgccatccga catccacagg tccattctca     60

cacataagtg ccaaacgcaa caggagggga tacactagca gcagaccgtt gcaaacgcag    120

gacctccact cctcttctcc tcaacaccca cttttgccat cgaaaaacca gcccagttat    180

tgggcttgat tggagctcgc tcattccaat tccttctatt aggctactaa caccatgact    240

ttattagcct gtctatcctg gcccccctgg cgaggttcat gtttgtttat ttccgaatgc    300

aacaagctcc gcattacacc cgaacatcac tccagatgag ggctttctga gtgtggggtc    360

aaatagtttc atgttcccca aatggcccaa aactgacagt ttaaacgctg tcttggaacc    420

taatatgaca aaagcgtgat ctcatccaag atgaactaag tttggttcgt tgaaatgcta    480

acggccagtt ggtcaaaaag aaacttccaa aagtcggcat accgtttgtc ttgtttggta    540

ttgattgacg aatgctcaaa aataatctca ttaatgctta gcgcagtctc tctatcgctt    600

ctgaaccccg gtgcacctgt gccgaaacgc aaatggggaa acacccgctt tttggatgat    660

tatgcattgt ctccacattg tatgcttcca agattctggt gggaatactg ctgatagcct    720

aacgttcatg atcaaaattt aactgttcta acccctactt gacagcaata tataaacaga    780

aggaagctgc cctgtcttaa accttttttt ttatcatcat tattagctta ctttcataat    840

tgcgactggt tccaattgac aagcttttga ttttaacgac ttttaacgac aacttgagaa    900

gatcaaaaaa caactaatta ttcgaaacga tgagatttcc ttcaattttt actgctgttt    960

tattcgcagc atcctccgca ttagctgctc cagtcaacac tacaacagaa gatgaaacgg   1020

cacaaattcc ggctgaagct gtcatcggtt actcagattt agaaggggat ttcgatgttg   1080

ctgttttgcc attttccaac agcacaaata acgggttatt gtttataaat actactattg   1140

ccagcattgc tgctaaagaa gaaggggtat ctctcgagaa aagagaggct gaagccatgg   1200

agaccgacgt ccacatatac ctgccgttca ctattattta gtgaaatgag atattatgat   1260

attttctgaa ttgtgattaa aaaggcaact ttatgcccat gcaacagaaa ctataaaaaa   1320

tacagagaat gaaaagaaac agatagattt tttagttctt taggcccgta gtctgcaaat   1380

ccttttatga ttttctatca aacaaaagag gaaaatagac cagttgcaat ccaaacgaga   1440

gtctaataga atgaggtcga aaagtaaatc gcgcgggttt gttactgata aagcaggcaa   1500

gacctaaaat gtgtaaaggg caaagtgtat actttggcgt caccccttac atattttagg   1560
```

```
tctttttta ttgtgcgtaa ctaacttgcc atcttcaaac aggagggctg gaagaagcag   1620
accgctaaca cagtacataa aaaaggagac atgaacgatg aacatcaaaa agtttgcaaa   1680
acaagcaaca gtattaacct ttactaccgc actgctggca ggaggcgcaa ctcaagcgtt   1740
tgcgaaagaa acgaaccaaa agccatataa ggaaacatac ggcatttccc atattacacg   1800
ccatgatatg ctgcaaatcc ctgaacagca aaaaaatgaa aaatataaag ttcctgagtt   1860
cgattcgtcc acaattaaaa atatctcttc tgcaaaaggc ctggacgttt gggacagctg   1920
gccattacaa aacactgacg gcactgtcgc aaactatcac ggctaccaca tcgtctttgc   1980
attagccgga gatcctaaaa atgcggatga cacatcgatt tacatgttct atcaaaaagt   2040
cggcgaaact tctattgaca gctggaaaaa cgctggccgc gtctttaaag acagcgacaa   2100
attcgatgca aatgattcta tcctaaaaga ccaaacacaa gaatggtcag gttcagccac   2160
atttacatct gacggaaaaa tccgtttatt ctacactgat ttctccggta aacattacgg   2220
caaacaaaca ctgacaactg cacaagttaa cgtatcagca tcagacagct ctttgaacat   2280
caacggtgta gaggattata aatcaatctt tgacggtgac ggaaaaacgt atcaaaatgt   2340
acagcagttc atcgatgaag gcaactacag ctcaggcgac aaccatacgc tgagagatcc   2400
tcactacgta gaagataaag gccacaaata cttagtattt gaagcaaaca ctggaactga   2460
agatggctac caaggcgaag aatctttatt taacaaagca tactatggca aaagcacatc   2520
attcttccgt caagaaagtc aaaaacttct gcaaagcgat aaaaaacgca cggctgagtt   2580
agcaaacggc gctctcggta tgattgagct aaacgatgat tacacactga aaaaagtgat   2640
gaaaccgctg attgcatcta acacagtaac agatgaaatt gaacgcgcga acgtctttaa   2700
aatgaacggc aaatggtacc tgttcactga ctcccgcgga tcaaaaatga cgattgacgg   2760
cattacgtct aacgatattt acatgcttgg ttatgtttct aattctttaa ctggcccata   2820
caagccgctg aacaaaactg gccttgtgtt aaaaatggat cttgatccta acgatgtaac   2880
ctttacttac tcacacttcg ctgtacctca agcgaaagga aacaatgtcg tgattacaag   2940
ctatatgaca aacagaggat tctacgcaga caaacaatca acgtttgcgc ctagcttcct   3000
gctgaacatc aaaggcaaga aaacatctgt tgtcaaagac agcatccttg aacaaggaca   3060
attaacagtt aacaaataaa aacgcaaaag aaaatgccga tatcctattg gcattgacgg   3120
tctcaagtac catcatcatc atcatcattg agtttgtagc cttagacatg actgttcctc   3180
agttcaagtt gggcacttac gagaagaccg gtcttgctag attctaatca agaggatgtc   3240
agaatgccat ttgcctgaga gatgcaggct tcatttttga tactttttta tttgtaacct   3300
atatagtata ggattttttt tgtcattttg tttcttctcg tacgagcttg ctcctgatca   3360
gcctatctcg cagctgatga atatcttgtg gtaggggttt gggaaaatca ttcgagtttg   3420
atgtttttct tggtatttcc cactcctctt cagagtacag aagattaagt gagacattcg   3480
tttgtgcgga tcccccacac accatagctt caaaatgttt ctactccttt tttactcttc   3540
cagattttct cggactccgc gcatcgccgt accacttcaa aacacccaag cacagcatac   3600
taaatttccc ctctttcttc ctctagggtg tcgttaatta cccgtactaa aggtttggaa   3660
aagaaaaaag agacagcctc gtttcttttt cttcgtcgaa aaaggcaata aaaattttta   3720
tcacgtttct ttttcttgaa attttttttt ttagtttttt tctctttcag tgacctccat   3780
tgatatttaa gttaataaac ggtcttcaat ttctcaagtt tcagtttcat ttttcttgtt   3840
ctattacaac tttttttact tcttgttcat tagaaagaaa gcatagcaat ctaatctaag   3900
gggcggtgtt gacaattaat catcggcata gtatatcggc atagtataat acgacaaggt   3960
```

gaggaactaa accatggcca agttgaccag tgccgttccg gtgctcaccg cgcgcgacgt 4020
cgccggagcg gtcgagttct ggaccgaccg gctcgggttc tcccgggact tcgtggagga 4080
cgacttcgcc ggtgtggtcc gggacgacgt gaccctgttc atcagcgcgg tccaggacca 4140
ggtggtgccg gacaacaccc tggcctgggt gtgggtgcgc ggcctggacg agctgtacgc 4200
cgagtggtcg gaggtcgtgt ccacgaactt ccgggacgcc tccgggccgg ccatgaccga 4260
gatcggcgag cagccgtggg ggcgggagtt cgccctgcgc gacccggccg gcaactgcgt 4320
gcacttcgtg gccgaggagc aggactgaca cgtccgacgg cggcccacgg gtcccaggcc 4380
tcggagatcc gtcccccttt tcctttgtcg atatcatgta attagttatg tcacgcttac 4440
attcacgccc tccccccaca tccgctctaa ccgaaaagga aggagttaga caacctgaag 4500
tctaggtccc tatttatttt tttatagtta tgttagtatt aagaacgtta tttatatttc 4560
aaatttttct ttttttctg tacagacgcg tgtacgcatg taacattata ctgaaaacct 4620
tgcttgagaa ggttttggga cgctcgaagg ctttaatttg caagctggag actaacatgt 4680
gagcaaaagg ccagcaaaag gccaggaacc gtaaaaaggc cgcgttgctg gcgtttttcc 4740
ataggctccg cccccctgac gagcatcaca aaaatcgacg ctcaagtcag aggtggcgaa 4800
acccgacagg actataaaga taccaggcgt ttccccctgg aagctccctc gtgcgctctc 4860
ctgttccgac cctgccgctt accggatacc tgtccgcctt tctcccttcg ggaagcgtgg 4920
cgctttctca atgctcacgc tgtaggtatc tcagttcggt gtaggtcgtt cgctccaagc 4980
tgggctgtgt gcacgaaccc cccgttcagc ccgaccgctg cgccttatcc ggtaactatc 5040
gtcttgagtc caacccggta agacacgact tatcgccact ggcagcagcc actggtaaca 5100
ggattagcag agcgaggtat gtaggcggtg ctacagagtt cttgaagtgg tggcctaact 5160
acggctacac tagaaggaca gtatttggta tctgcgctct gctgaagcca gttaccttcg 5220
gaaaaagagt tggtagctct tgatccggca aacaaaccac cgctggtagc ggtggttttt 5280
ttgtttgcaa gcagcagatt acgcgcagaa aaaaaggatc tcaagaagat cctttgatct 5340
tttctacggg gtctgacgct cagtggaacg aaaactcacg ttaagggatt ttggtcatga 5400
gatcagatct aacat 5415

<210> SEQ ID NO 12
<211> LENGTH: 3274
<212> TYPE: DNA
<213> ORGANISM: Artificial Sequence
<220> FEATURE:
<223> OTHER INFORMATION: pLVTSD Vector

<400> SEQUENCE: 12
tagtcttata actatactga caatagaaac attaacaaat ctaaaacagt cttaattcta 60
tcttgagaaa gtattggtaa taatattatt gtcgataacg cgagcataat aaacggctct 120
gattaaattc tgaagtttgt tagatacaat gatttcgttc gaaggaacta caaaataaat 180
tataaggagg cactcaaaat gagtacaaaa gattttaact tggatttggt atctgtttcg 240
aagaaagatt caggtgcatc accacgcatt acaagtattt cgctatgtac acccggttgt 300
aaaacaggag actctgcatg gatccatgaa gaagaagatt atctcagcta ttttaatgtc 360
tacagtgata ctttctgctg cagccccgtt gtcaggtgtt tacgctgcca tggagaccga 420
cgtgctagct gctactccgg acattgacgg tctccagtaa gaattcgcat gcgagctcgt 480
cgacagatct tctagactcg agtgcatatt ttcggcaatc ttctcaatga gatgctcttc 540

-continued

```
agcatgttca atgatgtcga ttttttatta aaacgtctca aaatcgtttc tgagacgttt    600
tagcgtttat ttcgtttagt tatcggcata atcgttaaaa caggcgttat cgtagcgtaa    660
aagcccttga gcgtagcgtg ctttgcagcg aagatgttgt ctgttagatt atgaaagccg    720
atgactgaat gaaataataa gcgcagcgtc cttctatttc ggttggagga ggctcaaggg    780
agtttgaggg aatgaaattc cctcatgggt ttgattttaa aaattgcttg caattttgcc    840
gagcggtagc gctggaaaat ttttgaaaaa aatttggaat ttggaaaaaa atggggggaa    900
aggaagcgaa ttttgcttcc gtactacgac cccccattaa gtgccgagtg ccaatttttg    960
tgccaaaaac gctctatccc aactggctca agggtttgag ggttttttca atcgccaacg   1020
aatcgccaac gttttcgcca acgtttttta taaatctata tttaagtagc tttattgttg   1080
tttttatgat tacaaagtga tacactaatt ttataaaatt atttgattgg agtttttttaa   1140
atggtgattt cagaatcgaa aaaaagagtt atgatttctc tgacaaaaga gcaagataaa   1200
aaattaacag atatggcgaa acaaaaaggt ttttcaaaat ctgcggttgc ggcgttagct   1260
atagaagaat atgcaagaaa ggaatcagaa caaaaaaaat aagcgaaagc tcgcgttttt   1320
agaaggatac gagttttcgc tacttgtttt tgataaggta atatatcatg gctattaaaa   1380
atactaaagc tagaaatttt ggatttttat tatatcctga ctcaattcct aatgattgga   1440
aagaaaaatt agagagtttg ggcgtatcta tggctgtcag tcctttacac gatatggacg   1500
aaaaaaaaga taaagataca tggaatagta gtgatgttat acgaaatgga aagcactata   1560
aaaaaccaca ctatcacgtt atatatattg cacgaaatcc tgtaacaata gaaagcgtta   1620
ggaacaagat taagcgaaaa ttggggaata gttcagttgc tcatgttgag atacttgatt   1680
atatcaaagg ttcatatgaa tatttgactc atgaatcaaa ggacgctatt gctaagaata   1740
aacatatata cgacaaaaaa gatattttga acattaatga ttttgatatt gaccgctata   1800
taacacttga tgaaagccaa aaaagagaat tgaagaattt acttttagat atagtggatg   1860
actataattt ggtaaataca aaagatttaa tggcttttat tcgccttagg ggagcggagt   1920
ttggaatttt aaatacgaat gatgtaaaag atattgtttc aacaaactct agcgccttta   1980
gattatggtt tgagggcaat tatcagtgtg gatatagagc aagttatgca aaggttcttg   2040
atgctgaaac gggggaaata aaatgacaaa caaagaaaaa gagttatttg ctgaaaatga   2100
ggaattaaaa aaagaaatta aggacttaaa agagcgtatt gaaagataca gagaaatgga   2160
agttgaatta agtacaacaa tagatttatt gagaggaggg attattgaat aaataaaagc   2220
ccccctgacg aaagtcgacg gcaatagtta cccttattat caagataaga aagaaaagga   2280
tttttcgcta cgctcaaatc ctttaaaaaa acacaaaaga ccacattttt taatgtggtc   2340
tttattcttc aactaaagca cccattagtt caacaaacga aaattggata aagtgggata   2400
tttttaaaat atatatttat gttacagtaa tattgacttt taaaaaagga ttgattctaa   2460
tgaagaaagc agacaagtaa gcctcctaaa ttcactttag ataaaaattt aggaggcata   2520
tcaaatgaac tttaataaaa ttgatttaga caattggaag agaaaagaga tatttaatca   2580
ttatttgaac caacaaacga cttttagtat aaccacagaa attgatatta gtgttttata   2640
ccgaaacata aaacaagaag gatataaatt ttaccctgca tttattttct tagtgacaag   2700
ggtgataaac tcaaatacag cttttagaac tggttacaat agcgacggag agttaggtta   2760
ttgggataag ttagagccac tttatacaat ttttgatggt gtatctaaaa cattctctgg   2820
tatttggact cctgtaaaga atgacttcaa agagttttat gatttatacc tttctgatgt   2880
agagaaatat aatggttcgg ggaaattgtt tcccaaaaca cctataccctg aaaatgcttt   2940
```

ttctctttct attattccat ggacttcatt tactgggttt aacttaaata tcaataataa 3000
tagtaattac cttctaccca ttattacagc aggaaaattc attaataaag gtaattcaat 3060
atatttaccg ctatctttac aggtacatca ttctgtttgt gatggttatc atgcaggatt 3120
gtttatgaac tctattcagg aattgtcaga taggcctaat gactggcttt tataatatga 3180
gataatgccg actgtacttt ttacagtcgg ttttctaatg tcactaacct gccccgttag 3240
ttgaagaagg tttttatatt acagctccaa gatc 3274

<210> SEQ ID NO 13
<211> LENGTH: 7284
<212> TYPE: DNA
<213> ORGANISM: Artificial Sequence
<220> FEATURE:
<223> OTHER INFORMATION: pVTSD1 Vector

<400> SEQUENCE: 13
taatacgact cactataggg gaattgtgag cggataacaa ttcccctcta gaaataattt 60
tgtttaactt taagaaggag atatacatat gcaccatcat catcatcatt cttctggtgt 120
agatctgggt accgagaacc tgtacttcca atccatggag accgacgtcc acatatacct 180
gccgttcact attatttagt gaaatgagat attatgatat tttctgaatt gtgattaaaa 240
aggcaacttt atgcccatgc aacagaaact ataaaaaata cagagaatga aaagaaacag 300
atagattttt tagttcttta ggcccgtagt ctgcaaatcc ttttatgatt ttctatcaaa 360
caaaagagga aaatagacca gttgcaatcc aaacgagagt ctaatagaat gaggtcgaaa 420
agtaaatcgc gcgggtttgt tactgataaa gcaggcaaga cctaaaatgt gtaaagggca 480
aagtgtatac tttggcgtca ccccttacat attttaggtc tttttttatt gtgcgtaact 540
aacttgccat cttcaaacag gagggctgga agaagcagac cgctaacaca gtacataaaa 600
aaggagacat gaacgatgaa catcaaaaag tttgcaaaac aagcaacagt attaaccttt 660
actaccgcac tgctggcagg aggcgcaact caagcgtttg cgaaagaaac gaaccaaaag 720
ccatataagg aaacatacgg catttcccat attacacgcc atgatatgct gcaaatccct 780
gaacagcaaa aaaatgaaaa atataaagtt cctgagttcg attcgtccac aattaaaaat 840
atctcttctg caaaaggcct ggacgtttgg gacagctggc cattacaaaa cactgacggc 900
actgtcgcaa actatcacgg ctaccacatc gtctttgcat tagccggaga tcctaaaaat 960
gcggatgaca catcgattta catgttctat caaaaagtcg gcgaaacttc tattgacagc 1020
tggaaaaacg ctggccgcgt ctttaaagac agcgacaaat tcgatgcaaa tgattctatc 1080
ctaaaagacc aaacacaaga atggtcaggt tcagccacat ttacatctga cggaaaaatc 1140
cgtttattct acactgattt ctccggtaaa cattacggca aacaaacact gacaactgca 1200
caagttaacg tatcagcatc agacagctct ttgaacatca acggtgtaga ggattataaa 1260
tcaatctttg acggtgacgg aaaaacgtat caaaatgtac agcagttcat cgatgaaggc 1320
aactacagct caggcgacaa ccatacgctg agagatcctc actacgtaga agataaaggc 1380
cacaaatact tagtatttga agcaaacact ggaactgaag atggctacca aggcgaagaa 1440
tctttattta acaaagcata ctatggcaaa agcacatcat tcttccgtca agaaagtcaa 1500
aaacttctgc aaagcgataa aaaacgcacg gctgagttag caaacggcgc tctcggtatg 1560
attgagctaa acgatgatta cacactgaaa aaagtgatga aaccgctgat tgcatctaac 1620
acagtaacag atgaaattga acgcgcgaac gtctttaaaa tgaacggcaa atggtacctg 1680

-continued

```
ttcactgact cccgcggatc aaaaatgacg attgacggca ttacgtctaa cgatatttac   1740
atgcttggtt atgtttctaa ttctttaact ggcccataca agccgctgaa caaaactggc   1800
cttgtgttaa aaatggatct tgatcctaac gatgtaacct ttacttactc acacttcgct   1860
gtacctcaag cgaaaggaaa caatgtcgtg attacaagct atatgacaaa cagaggattc   1920
tacgcagaca aacaatcaac gtttgcgcct agcttcctgc tgaacatcaa aggcaagaaa   1980
acatctgttg tcaaagacag catccttgaa caaggacaat taacagttaa caaataaaaa   2040
cgcaaaagaa aatgccgata tcctattggc attgacggtc tccagtaaag gtggatacgg   2100
atccgaattc gagctccgtc gacaagcttg cggccgcact cgagcaccac caccaccacc   2160
actgagatcc ggctgctaac aaagcccgaa aggaagctga gttggctgct gccaccgctg   2220
agcaataact agcataaccc cttggggcct ctaaacgggt cttgaggggt tttttgctga   2280
aaggaggaac tatatccgga ttggcgaatg ggacgcgccc tgtagcggcg cattaagcgc   2340
ggcgggtgtg gtggttacgc gcagcgtgac cgctacactt gccagcgccc tagcgcccgc   2400
tcctttcgct ttcttccctt cctttctcgc cacgttcgcc ggctttcccc gtcaagctct   2460
aaatcggggg ctccctttag ggttccgatt tagtgcttta cggcacctcg accccaaaaa   2520
acttgattag ggtgatggtt cacgtagtgg gccatcgccc tgatagacgg tttttcgccc   2580
tttgacgttg gagtccacgt tctttaatag tggactcttg ttccaaactg gaacaacact   2640
caaccctatc tcggtctatt cttttgattt ataagggatt ttgccgattt cggcctattg   2700
gttaaaaaat gagctgattt aacaaaaatt taacgcgaat tttaacaaaa tattaacgtt   2760
tacaatttca ggtggcactt ttcggggaaa tgtgcgcgga acccctattt gtttattttt   2820
ctaaatacat tcaaatatgt atccgctcat gaattaattc ttagaaaaac tcatcgagca   2880
tcaaatgaaa ctgcaattta ttcatatcag gattatcaat accatatttt tgaaaaagcc   2940
gtttctgtaa tgaaggagaa aactcaccga ggcagttcca taggatggca agatcctggt   3000
atcggtctgc gattccgact cgtccaacat caatacaacc tattaatttc ccctcgtcaa   3060
aaataaggtt atcaagtgag aaatcaccat gagtgacgac tgaatccggt gagaatggca   3120
aaagtttatg catttctttc cagacttgtt caacaggcca gccattacgc tcgtcatcaa   3180
aatcactcgc atcaaccaaa ccgttattca ttcgtgattg cgcctgagcg agacgaaata   3240
cgcgatcgct gttaaaagga caattacaaa caggaatcga atgcaaccgg cgcaggaaca   3300
ctgccagcgc atcaacaata ttttcacctg aatcaggata ttcttctaat acctggaatg   3360
ctgttttccc ggggatcgca gtggtgagta accatgcatc atcaggagta cggataaaat   3420
gcttgatggt cggaagaggc ataaattccg tcagccagtt tagtctgacc atctcatctg   3480
taacatcatt ggcaacgcta cctttgccat gtttcagaaa caactctggc gcatcgggct   3540
tcccatacaa tcgatagatt gtcgcacctg attgcccgac attatcgcga gcccatttat   3600
acccatataa atcagcatcc atgttggaat ttaatcgcgg cctagagcaa gacgtttccc   3660
gttgaatatg gctcataaca ccccttgtat tactgtttat gtaagcagac agttttattg   3720
ttcatgacca aaatccctta acgtgagttt tcgttccact gagcgtcaga ccccgtagaa   3780
aagatcaaag gatcttcttg agatcctttt tttctgcgcg taatctgctg cttgcaaaca   3840
aaaaaaccac cgctaccagc ggtggtttgt ttgccggatc aagagctacc aactcttttt   3900
ccgaaggtaa ctggcttcag cagagcgcag ataccaaata ctgtccttct agtgtagccg   3960
tagttaggcc accacttcaa gaactctgta gcaccgccta catacctcgc tctgctaatc   4020
ctgttaccag tggctgctgc cagtggcgat aagtcgtgtc ttaccgggtt ggactcaaga   4080
```

```
cgatagttac cggataaggc gcagcggtcg ggctgaacgg ggggttcgtg cacacagccc   4140
agcttggagc gaacgaccta caccgaactg agatacctac agcgtgagct atgagaaagc   4200
gccacgcttc ccgaagggag aaaggcggac aggtatccgg taagcggcag ggtcggaaca   4260
ggagagcgca cgagggagct tccaggggga aacgcctggt atctttatag tcctgtcggg   4320
tttcgccacc tctgacttga gcgtcgattt ttgtgatgct cgtcaggggg gcggagccta   4380
tggaaaaacg ccagcaacgc ggccttttta cggttcctgg ccttttgctg gccttttgct   4440
cacatgttct ttcctgcgtt atcccctgat tctgtggata accgtattac cgcctttgag   4500
tgagctgata ccgctcgccg cagccgaacg accgagcgca gcgagtcagt gagcgaggaa   4560
gcggaagagc gcctgatgcg gtattttctc cttacgcatc tgtgcggtat ttcacaccgc   4620
atatatggtg cactctcagt acaatctgct ctgatgccgc atagttaagc cagtatacac   4680
tccgctatcg ctacgtgact gggtcatggc tgcgccccga cacccgccaa cacccgctga   4740
cgcgccctga cgggcttgtc tgctcccggc atccgcttac agacaagctg tgaccgtctc   4800
cgggagctgc atgtgtcaga ggttttcacc gtcatcaccg aaacgcgcga ggcagctgcg   4860
gtaaagctca tcagcgtggt cgtgaagcga ttcacagatg tctgcctgtt catccgcgtc   4920
cagctcgttg agtttctcca gaagcgttaa tgtctggctt ctgataaagc gggccatgtt   4980
aagggcggtt ttttcctgtt tggtcactga tgcctccgtg taagggggat ttctgttcat   5040
gggggtaatg ataccgatga aacgagagag gatgctcacg atacgggtta ctgatgatga   5100
acatgcccgg ttactggaac gttgtgaggg taaacaactg gcggtatgga tgcggcggga   5160
ccagagaaaa atcactcagg gtcaatgcca gcgcttcgtt aatacagatg taggtgttcc   5220
acagggtagc cagcagcatc ctgcgatgca gatccggaac ataatggtgc agggcgctga   5280
cttccgcgtt tccagacttt acgaaacacg gaaaccgaag accattcatg ttgttgctca   5340
ggtcgcagac gttttgcagc agcagtcgct tcacgttcgc tcgcgtatcg gtgattcatt   5400
ctgctaacca gtaaggcaac cccgccagcc tagccgggtc ctcaacgaca ggagcacgat   5460
catgcgcacc cgtggggccg ccatgccggc gataatggcc tgcttctcgc cgaaacgttt   5520
ggtggcggga ccagtgacga aggcttgagc gagggcgtgc aagattccga ataccgcaag   5580
cgacaggccg atcatcgtcg cgctccagcg aaagcggtcc tcgccgaaaa tgacccagag   5640
cgctgccggc acctgtccta cgagttgcat gataaagaag acagtcataa gtgcggcgac   5700
gatagtcatg ccccgcgccc accggaagga gctgactggg ttgaaggctc tcaagggcat   5760
cggtcgagat cccggtgcct aatgagtgag ctaacttaca ttaattgcgt tgcgctcact   5820
gcccgctttc cagtcgggaa acctgtcgtg ccagctgcat taatgaatcg gccaacgcgc   5880
ggggagaggc ggtttgcgta ttgggcgcca gggtggtttt tcttttcacc agtgagacgg   5940
gcaacagctg attgcccttc accgcctggc cctgagagag ttgcagcaag cggtccacgc   6000
tggtttgccc cagcaggcga aaatcctgtt tgatggtggt taacggcggg atataacatg   6060
agctgtcttc ggtatcgtcg tatcccacta ccgagatatc cgcaccaacg cgcagcccgg   6120
actcggtaat ggcgcgcatt gcgcccagcg ccatctgatc gttggcaacc agcatcgcag   6180
tgggaacgat gccctcattc agcatttgca tggtttgttg aaaaccggac atggcactcc   6240
agtcgccttc ccgttccgct atcggctgaa tttgattgcg agtgagatat ttatgccagc   6300
cagccagacg cagacgcgcc gagacagaac ttaatgggcc cgctaacagc gcgatttgct   6360
ggtgacccaa tgcgaccaga tgctccacgc ccagtcgcgt accgtcttca tgggagaaaa   6420
```

```
taatactgtt gatgggtgtc tggtcagaga catcaagaaa taacgccgga acattagtgc   6480

aggcagcttc cacagcaatg gcatcctggt catccagcgg atagttaatg atcagcccac   6540

tgacgcgttg cgcgagaaga ttgtgcaccg ccgctttaca ggcttcgacg ccgcttcgtt   6600

ctaccatcga caccaccacg ctggcaccca gttgatcggc gcgagattta atcgccgcga   6660

caatttgcga cggcgcgtgc agggccagac tggaggtggc aacgccaatc agcaacgact   6720

gtttgcccgc cagttgttgt gccacgcggt tgggaatgta attcagctcc gccatcgccg   6780

cttccacttt ttcccgcgtt ttcgcagaaa cgtggctggc ctggttcacc acgcgggaaa   6840

cggtctgata agagacaccg gcatactctg cgacatcgta taacgttact ggtttcacat   6900

tcaccaccct gaattgactc tcttccgggc gctatcatgc cataccgcga aaggttttgc   6960

gccattcgat ggtgtccggg atctcgacgc tctcccttat gcgactcctg cattaggaag   7020

cagcccagta gtaggttgag gccgttgagc accgccgccg caaggaatgg tgcatgcaag   7080

gagatggcgc ccaacagtcc cccggccacg gggcctgcca ccatacccac gccgaaacaa   7140

gcgctcatga gcccgaagtg gcgagcccga tcttccccat cggtgatgtc ggcgatatag   7200

gcgccagcaa ccgcacctgt ggcgccggtg atgccggcca cgatgcgtcc ggcgtagagg   7260

atcgagatct cgatcccgcg aaat                                          7284
```

```
<210> SEQ ID NO 14
<211> LENGTH: 7227
<212> TYPE: DNA
<213> ORGANISM: Artificial Sequence
<220> FEATURE:
<223> OTHER INFORMATION: pVTSD2 Vector

<400> SEQUENCE: 14

taatacgact cactataggg gaattgtgag cggataacaa ttcccctcta gaaataattt     60

tgtttaactt taagaaggag atataaccat ggagaccgac gtccacatat acctgccgtt    120

cactattatt tagtgaaatg agatattatg atattttctg aattgtgatt aaaaaggcaa    180

ctttatgccc atgcaacaga aactataaaa aatacagaga atgaaaagaa acagatagat    240

tttttagttc tttaggcccg tagtctgcaa atccttttat gattttctat caaacaaaag    300

aggaaaatag accagttgca atccaaacga gagtctaata gaatgaggtc gaaaagtaaa    360

tcgcgcgggt ttgttactga taaagcaggc aagacctaaa atgtgtaaag ggcaaagtgt    420

atactttggc gtcacccctt acatatttta ggtctttttt tattgtgcgt aactaacttg    480

ccatcttcaa acaggagggc tggaagaagc agaccgctaa cacagtacat aaaaaaggag    540

acatgaacga tgaacatcaa aaagtttgca aaacaagcaa cagtattaac ctttactacc    600

gcactgctgg caggaggcgc aactcaagcg tttgcgaaag aaacgaacca aaagccatat    660

aaggaaacat acggcatttc ccatattaca cgccatgata tgctgcaaat ccctgaacag    720

caaaaaaatg aaaaatataa agttcctgag ttcgattcgt ccacaattaa aaatatctct    780

tctgcaaaag gcctggacgt ttgggacagc tggccattac aaaacactga cggcactgtc    840

gcaaactatc acggctacca catcgtcttt gcattagccg gagatcctaa aaatgcggat    900

gacacatcga tttacatgtt ctatcaaaaa gtcggcgaaa cttctattga cagctggaaa    960

aacgctggcc gcgtctttaa agacagcgac aaattcgatg caaatgattc tatcctaaaa   1020

gaccaaacac aagaatggtc aggttcagcc acatttacat ctgacggaaa aatccgttta   1080

ttctacactg atttctccgg taaacattac ggcaaacaaa cactgacaac tgcacaagtt   1140

aacgtatcag catcagacag ctctttgaac atcaacggtg tagaggatta taaatcaatc   1200
```

-continued

```
tttgacggtg acggaaaaac gtatcaaaat gtacagcagt tcatcgatga aggcaactac   1260
agctcaggcg acaaccatac gctgagagat cctcactacg tagaagataa aggccacaaa   1320
tacttagtat ttgaagcaaa cactggaact gaagatggct accaaggcga agaatcttta   1380
tttaacaaag catactatgg caaaagcaca tcattcttcc gtcaagaaag tcaaaaactt   1440
ctgcaaagcg ataaaaaacg cacggctgag ttagcaaacg gcgctctcgg tatgattgag   1500
ctaaacgatg attacacact gaaaaaagtg atgaaaccgc tgattgcatc taacacagta   1560
acagatgaaa ttgaacgcgc gaacgtcttt aaaatgaacg gcaaatggta cctgttcact   1620
gactcccgcg gatcaaaaat gacgattgac ggcattacgt ctaacgatat ttacatgctt   1680
ggttatgttt ctaattcttt aactggccca tacaagccgc tgaacaaaac tggccttgtg   1740
ttaaaaatgg atcttgatcc taacgatgta acctttactt actcacactt cgctgtacct   1800
caagcgaaag gaaacaatgt cgtgattaca agctatatga caaacagagg attctacgca   1860
gacaaacaat caacgtttgc gcctagcttc ctgctgaaca tcaaaggcaa gaaaacatct   1920
gttgtcaaag acagcatcct tgaacaagga caattaacag ttaacaaata aaaacgcaaa   1980
agaaaatgcc gatatcctat tggcattgac ggtctccagt aaggatccta taggtggata   2040
cggatccgaa ttcgagctcc gtcgacaagc ttgcggccgc actcgagcac caccaccacc   2100
accactgaga tccggctgct aacaaagccc gaaaggaagc tgagttggct gctgccaccg   2160
ctgagcaata actagcataa ccccttgggg cctctaaacg ggtcttgagg ggttttttgc   2220
tgaaaggagg aactatatcc ggattggcga atgggacgcg ccctgtagcg gcgcattaag   2280
cgcggcgggt gtggtggtta cgcgcagcgt gaccgctaca cttgccagcg ccctagcgcc   2340
cgctcctttc gctttcttcc cttcctttct cgccacgttc gccggctttc cccgtcaagc   2400
tctaaatcgg gggctccctt tagggttccg atttagtgct ttacggcacc tcgaccccaa   2460
aaaacttgat tagggtgatg gttcacgtag tgggccatcg ccctgataga cggtttttcg   2520
ccctttgacg ttggagtcca cgttctttaa tagtggactc ttgttccaaa ctggaacaac   2580
actcaaccct atctcggtct attcttttga tttataaggg attttgccga tttcggccta   2640
ttggttaaaa aatgagctga tttaacaaaa atttaacgcg aattttaaca aaatattaac   2700
gtttacaatt tcaggtggca cttttcgggg aaatgtgcgc ggaaccccta tttgtttatt   2760
tttctaaata cattcaaata tgtatccgct catgaattaa ttcttagaaa aactcatcga   2820
gcatcaaatg aaactgcaat ttattcatat caggattatc aataccatat ttttgaaaaa   2880
gccgtttctg taatgaagga gaaaactcac cgaggcagtt ccataggatg gcaagatcct   2940
ggtatcggtc tgcgattccg actcgtccaa catcaataca acctattaat ttcccctcgt   3000
caaaaataag gttatcaagt gagaaatcac catgagtgac gactgaatcc ggtgagaatg   3060
gcaaaagttt atgcatttct ttccagactt gttcaacagg ccagccatta cgctcgtcat   3120
caaaatcact cgcatcaacc aaaccgttat tcattcgtga ttgcgcctga gcgagacgaa   3180
atacgcgatc gctgttaaaa ggacaattac aaacaggaat cgaatgcaac cggcgcagga   3240
acactgccag cgcatcaaca atattttcac ctgaatcagg atattcttct aatacctgga   3300
atgctgtttt cccggggatc gcagtggtga gtaaccatgc atcatcagga gtacggataa   3360
aatgcttgat ggtcggaaga ggcataaatt ccgtcagcca gtttagtctg accatctcat   3420
ctgtaacatc attggcaacg ctacctttgc catgtttcag aaacaactct ggcgcatcgg   3480
gcttcccata caatcgatag attgtcgcac ctgattgccc gacattatcg cgagcccatt   3540
```

-continued

```
tatacccata taaatcagca tccatgttgg aatttaatcg cggcctagag caagacgttt   3600
cccgttgaat atggctcata acaccccttg tattactgtt tatgtaagca gacagtttta   3660
ttgttcatga ccaaaatccc ttaacgtgag ttttcgttcc actgagcgtc agaccccgta   3720
gaaaagatca aaggatcttc ttgagatcct ttttttctgc gcgtaatctg ctgcttgcaa   3780
acaaaaaaac caccgctacc agcggtggtt tgtttgccgg atcaagagct accaactctt   3840
tttccgaagg taactggctt cagcagagcg cagataccaa atactgtcct tctagtgtag   3900
ccgtagttag gccaccactt caagaactct gtagcaccgc ctacatacct cgctctgcta   3960
atcctgttac cagtggctgc tgccagtggc gataagtcgt gtcttaccgg gttggactca   4020
agacgatagt taccggataa ggcgcagcgg tcgggctgaa cggggggttc gtgcacacag   4080
cccagcttgg agcgaacgac ctacaccgaa ctgagatacc tacagcgtga gctatgagaa   4140
agcgccacgc ttcccgaagg gagaaaggcg gacaggtatc cggtaagcgg cagggtcgga   4200
acaggagagc gcacgaggga gcttccaggg ggaaacgcct ggtatcttta tagtcctgtc   4260
gggtttcgcc acctctgact tgagcgtcga tttttgtgat gctcgtcagg ggggcggagc   4320
ctatggaaaa acgccagcaa cgcggccttt ttacggttcc tggccttttg ctggcctttt   4380
gctcacatgt tctttcctgc gttatcccct gattctgtgg ataaccgtat taccgccttt   4440
gagtgagctg ataccgctcg ccgcagccga acgaccgagc gcagcgagtc agtgagcgag   4500
gaagcggaag agcgcctgat gcggtatttt ctccttacgc atctgtgcgg tatttcacac   4560
cgcatatatg gtgcactctc agtacaatct gctctgatgc cgcatagtta agccagtata   4620
cactccgcta tcgctacgtg actgggtcat ggctgcgccc cgacacccgc caacacccgc   4680
tgacgcgccc tgacgggctt gtctgctccc ggcatccgct tacagacaag ctgtgaccgt   4740
ctccgggagc tgcatgtgtc agaggttttc accgtcatca ccgaaacgcg cgaggcagct   4800
gcggtaaagc tcatcagcgt ggtcgtgaag cgattcacag atgtctgcct gttcatccgc   4860
gtccagctcg ttgagtttct ccagaagcgt taatgtctgg cttctgataa agcgggccat   4920
gttaagggcg gttttttcct gtttggtcac tgatgcctcc gtgtaagggg gatttctgtt   4980
catgggggta atgataccga tgaaacgaga gaggatgctc acgatacggg ttactgatga   5040
tgaacatgcc cggttactgg aacgttgtga gggtaaacaa ctggcggtat ggatgcggcg   5100
ggaccagaga aaaatcactc agggtcaatg ccagcgcttc gttaatacag atgtaggtgt   5160
tccacagggt agccagcagc atcctgcgat gcagatccgg aacataatgg tgcagggcgc   5220
tgacttccgc gtttccagac tttacgaaac acggaaaccg aagaccattc atgttgttgc   5280
tcaggtcgca gacgttttgc agcagcagtc gcttcacgtt cgctcgcgta tcggtgattc   5340
attctgctaa ccagtaaggc aaccccgcca gcctagccgg gtcctcaacg acaggagcac   5400
gatcatgcgc acccgtgggg ccgccatgcc ggcgataatg gcctgcttct cgccgaaacg   5460
tttggtggcg ggaccagtga cgaaggcttg agcgagggcg tgcaagattc cgaataccgc   5520
aagcgacagg ccgatcatcg tcgcgctcca gcgaaagcgg tcctcgccga aaatgaccca   5580
gagcgctgcc ggcacctgtc ctacgagttg catgataaag aagacagtca taagtgcggc   5640
gacgatagtc atgccccgcg cccaccggaa ggagctgact gggttgaagg ctctcaaggg   5700
catcggtcga gatcccggtg cctaatgagt gagctaactt acattaattg cgttgcgctc   5760
actgcccgct ttccagtcgg gaaacctgtc gtgccagctg cattaatgaa tcggccaacg   5820
cgcggggaga ggcggtttgc gtattgggcg ccagggtggt ttttcttttc accagtgaga   5880
cgggcaacag ctgattgccc ttcaccgcct ggccctgaga gagttgcagc aagcggtcca   5940
```

```
cgctggtttg ccccagcagg cgaaaatcct gtttgatggt ggttaacggc gggatataac   6000

atgagctgtc ttcggtatcg tcgtatccca ctaccgagat atccgcacca acgcgcagcc   6060

cggactcggt aatggcgcgc attgcgccca gcgccatctg atcgttggca accagcatcg   6120

cagtgggaac gatgccctca ttcagcattt gcatggtttg ttgaaaaccg gacatggcac   6180

tccagtcgcc ttcccgttcc gctatcggct gaatttgatt gcgagtgaga tatttatgcc   6240

agccagccag acgcagacgc gccgagacag aacttaatgg gcccgctaac agcgcgattt   6300

gctggtgacc caatgcgacc agatgctcca cgcccagtcg cgtaccgtct tcatgggaga   6360

aaataatact gttgatgggt gtctggtcag agacatcaag aaataacgcc ggaacattag   6420

tgcaggcagc ttccacagca atggcatcct ggtcatccag cggatagtta atgatcagcc   6480

cactgacgcg ttgcgcgaga agattgtgca ccgccgcttt acaggcttcg acgccgcttc   6540

gttctaccat cgacaccacc acgctggcac ccagttgatc ggcgcgagat ttaatcgccg   6600

cgacaatttg cgacggcgcg tgcagggcca gactggaggt ggcaacgcca atcagcaacg   6660

actgtttgcc cgccagttgt tgtgccacgc ggttgggaat gtaattcagc tccgccatcg   6720

ccgcttccac tttttcccgc gttttcgcag aaacgtggct ggcctggttc accacgcggg   6780

aaacggtctg ataagagaca ccggcatact ctgcgacatc gtataacgtt actggtttca   6840

cattcaccac cctgaattga ctctcttccg ggcgctatca tgccataccg cgaaaggttt   6900

tgcgccattc gatggtgtcc gggatctcga cgctctccct tatgcgactc ctgcattagg   6960

aagcagccca gtagtaggtt gaggccgttg agcaccgccg ccgcaaggaa tggtgcatgc   7020

aaggagatgg cgcccaacag tcccccggcc acggggcctg ccaccatacc cacgccgaaa   7080

caagcgctca tgagcccgaa gtggcgagcc cgatcttccc catcggtgat gtcggcgata   7140

taggcgccag caaccgcacc tgtggcgccg gtgatgccgg ccacgatgcg tccggcgtag   7200

aggatcgaga tctcgatccc gcgaaat                                       7227
```

<210> SEQ ID NO 15
<211> LENGTH: 7202
<212> TYPE: DNA
<213> ORGANISM: Artificial Sequence
<220> FEATURE:
<223> OTHER INFORMATION: pVTSD3 Vector

<400> SEQUENCE: 15

```
taatacgact cactataggg gaattgtgag cggataacaa ttcccctcta gaaataattt     60

tgtttaactt taagaaggag atataaccat ggagaccgac gtccacatat acctgccgtt    120

cactattatt tagtgaaatg agatattatg atattttctg aattgtgatt aaaaaggcaa    180

ctttatgccc atgcaacaga aactataaaa aatacagaga atgaaaagaa acagatagat    240

tttttagttc tttaggcccg tagtctgcaa atccttttat gattttctat caaacaaaag    300

aggaaaatag accagttgca atccaaacga gagtctaata gaatgaggtc gaaaagtaaa    360

tcgcgcgggt ttgttactga taaagcaggc aagacctaaa atgtgtaaag ggcaaagtgt    420

atactttggc gtcacccctt acatatttta ggtctttttt tattgtgcgt aactaacttg    480

ccatcttcaa acaggagggc tggaagaagc agaccgctaa cacagtacat aaaaaaggag    540

acatgaacga tgaacatcaa aaagtttgca aaacaagcaa cagtattaac ctttactacc    600

gcactgctgg caggaggcgc aactcaagcg tttgcgaaag aaacgaacca aaagccatat    660

aaggaaacat acggcatttc ccatattaca cgccatgata tgctgcaaat ccctgaacag    720
```

-continued

```
caaaaaaatg aaaaatataa agttcctgag ttcgattcgt ccacaattaa aaatatctct    780
tctgcaaaag gcctggacgt ttgggacagc tggccattac aaaacactga cggcactgtc    840
gcaaactatc acggctacca catcgtcttt gcattagccg gagatcctaa aaatgcggat    900
gacacatcga tttacatgtt ctatcaaaaa gtcggcgaaa cttctattga cagctggaaa    960
aacgctggcc gcgtctttaa agacagcgac aaattcgatg caaatgattc tatcctaaaa   1020
gaccaaacac aagaatggtc aggttcagcc acatttacat ctgacggaaa aatccgttta   1080
ttctacactg atttctccgg taaacattac ggcaaacaaa cactgacaac tgcacaagtt   1140
aacgtatcag catcagacag ctctttgaac atcaacggtg tagaggatta taaatcaatc   1200
tttgacggtg acggaaaaac gtatcaaaat gtacagcagt tcatcgatga aggcaactac   1260
agctcaggcg acaaccatac gctgagagat cctcactacg tagaagataa aggccacaaa   1320
tacttagtat ttgaagcaaa cactggaact gaagatggct accaaggcga agaatcttta   1380
tttaacaaag catactatgg caaaagcaca tcattcttcc gtcaagaaag tcaaaaactt   1440
ctgcaaagcg ataaaaaacg cacggctgag ttagcaaacg gcgctctcgg tatgattgag   1500
ctaaacgatg attacacact gaaaaaagtg atgaaaccgc tgattgcatc taacacagta   1560
acagatgaaa ttgaacgcgc gaacgtcttt aaaatgaacg gcaaatggta cctgttcact   1620
gactcccgcg gatcaaaaat gacgattgac ggcattacgt ctaacgatat ttacatgctt   1680
ggttatgttt ctaattcttt aactggccca tacaagccgc tgaacaaaac tggccttgtg   1740
ttaaaaatgg atcttgatcc taacgatgta acctttactt actcacactt cgctgtacct   1800
caagcgaaag gaaacaatgt cgtgattaca agctatatga caaacagagg attctacgca   1860
gacaaacaat caacgtttgc gcctagcttc ctgctgaaca tcaaaggcaa gaaaacatct   1920
gttgtcaaag acagcatcct tgaacaagga caattaacag ttaacaaata aaaacgcaaa   1980
agaaaatgcc gatatcctat tggcattgac ggtctccagt accaccatca tcatcatcat   2040
taagtcagcg gccgcactcg agcaccacca ccaccaccac tgagatccgg ctgctaacaa   2100
agcccgaaag gaagctgagt tggctgctgc caccgctgag caataactag cataacccct   2160
tggggcctct aaacgggtct tgaggggttt tttgctgaaa ggaggaacta tatccggatt   2220
ggcgaatggg acgcgccctg tagcggcgca ttaagcgcgg cgggtgtggt ggttacgcgc   2280
agcgtgaccg ctacacttgc cagcgcccta gcgcccgctc ctttcgcttt cttcccttcc   2340
tttctcgcca cgttcgccgg ctttccccgt caagctctaa atcgggggct ccctttaggg   2400
ttccgattta gtgctttacg gcacctcgac cccaaaaaac ttgattaggg tgatggttca   2460
cgtagtgggc catcgccctg atagacggtt tttcgccctt tgacgttgga gtccacgttc   2520
tttaatagtg gactcttgtt ccaaactgga acaacactca accctatctc ggtctattct   2580
tttgatttat aagggatttt gccgatttcg gcctattggt taaaaaatga gctgatttaa   2640
caaaaattta acgcgaattt taacaaaata ttaacgttta caatttcagg tggcactttt   2700
cggggaaatg tgcgcggaac ccctatttgt ttatttttct aaatacattc aaatatgtat   2760
ccgctcatga attaattctt agaaaaactc atcgagcatc aaatgaaact gcaatttatt   2820
catatcagga ttatcaatac catatttttg aaaaagccgt ttctgtaatg aaggagaaaa   2880
ctcaccgagg cagttccata ggatggcaag atcctggtat cggtctgcga ttccgactcg   2940
tccaacatca atacaaccta ttaatttccc ctcgtcaaaa ataaggttat caagtgagaa   3000
atcaccatga gtgacgactg aatccggtga gaatggcaaa agtttatgca tttctttcca   3060
gacttgttca acaggccagc cattacgctc gtcatcaaaa tcactcgcat caaccaaacc   3120
```

-continued

```
gttattcatt cgtgattgcg cctgagcgag acgaaatacg cgatcgctgt taaaaggaca   3180
attacaaaca ggaatcgaat gcaaccggcg caggaacact gccagcgcat caacaatatt   3240
ttcacctgaa tcaggatatt cttctaatac ctggaatgct gttttcccgg ggatcgcagt   3300
ggtgagtaac catgcatcat caggagtacg gataaaatgc ttgatggtcg gaagaggcat   3360
aaattccgtc agccagttta gtctgaccat ctcatctgta acatcattgg caacgctacc   3420
tttgccatgt ttcagaaaca actctggcgc atcgggcttc ccatacaatc gatagattgt   3480
cgcacctgat tgcccgacat tatcgcgagc ccatttatac ccatataaat cagcatccat   3540
gttggaattt aatcgcggcc tagagcaaga cgtttcccgt tgaatatggc tcataacacc   3600
ccttgtatta ctgtttatgt aagcagacag ttttattgtt catgaccaaa atcccttaac   3660
gtgagttttc gttccactga gcgtcagacc ccgtagaaaa gatcaaagga tcttcttgag   3720
atcctttttt tctgcgcgta atctgctgct tgcaaacaaa aaaaccaccg ctaccagcgg   3780
tggtttgttt gccggatcaa gagctaccaa ctctttttcc gaaggtaact ggcttcagca   3840
gagcgcagat accaaatact gtccttctag tgtagccgta gttaggccac cacttcaaga   3900
actctgtagc accgcctaca tacctcgctc tgctaatcct gttaccagtg gctgctgcca   3960
gtggcgataa gtcgtgtctt accgggttgg actcaagacg atagttaccg gataaggcgc   4020
agcggtcggg ctgaacgggg ggttcgtgca cacagcccag cttggagcga acgacctaca   4080
ccgaactgag atacctacag cgtgagctat gagaaagcgc cacgcttccc gaagggagaa   4140
aggcggacag gtatccggta agcggcaggg tcggaacagg agagcgcacg agggagcttc   4200
cagggggaaa cgcctggtat ctttatagtc ctgtcgggtt tcgccacctc tgacttgagc   4260
gtcgattttt gtgatgctcg tcaggggggc ggagcctatg gaaaaacgcc agcaacgcgg   4320
cctttttacg gttcctggcc ttttgctggc cttttgctca catgttcttt cctgcgttat   4380
cccctgattc tgtggataac cgtattaccg cctttgagtg agctgatacc gctcgccgca   4440
gccgaacgac cgagcgcagc gagtcagtga gcgaggaagc ggaagagcgc ctgatgcggt   4500
attttctcct tacgcatctg tgcggtattt cacaccgcat atatggtgca ctctcagtac   4560
aatctgctct gatgccgcat agttaagcca gtatacactc cgctatcgct acgtgactgg   4620
gtcatggctg cgccccgaca cccgccaaca cccgctgacg cgccctgacg ggcttgtctg   4680
ctcccggcat ccgcttacag acaagctgtg accgtctccg ggagctgcat gtgtcagagg   4740
ttttcaccgt catcaccgaa acgcgcgagg cagctgcggt aaagctcatc agcgtggtcg   4800
tgaagcgatt cacagatgtc tgcctgttca tccgcgtcca gctcgttgag tttctccaga   4860
agcgttaatg tctggcttct gataaagcgg gccatgttaa gggcggtttt ttcctgtttg   4920
gtcactgatg cctccgtgta agggggattt ctgttcatgg gggtaatgat accgatgaaa   4980
cgagagagga tgctcacgat acgggttact gatgatgaac atgcccggtt actggaacgt   5040
tgtgagggta aacaactggc ggtatggatg cggcgggacc agagaaaaat cactcagggt   5100
caatgccagc gcttcgttaa tacagatgta ggtgttccac agggtagcca gcagcatcct   5160
gcgatgcaga tccggaacat aatggtgcag ggcgctgact tccgcgtttc cagactttac   5220
gaaacacgga aaccgaagac cattcatgtt gttgctcagg tcgcagacgt tttgcagcag   5280
cagtcgcttc acgttcgctc gcgtatcggt gattcattct gctaaccagt aaggcaaccc   5340
cgccagccta gccgggtcct caacgacagg agcacgatca tgcgcacccg tggggccgcc   5400
atgccggcga taatggcctg cttctcgccg aaacgtttgg tggcgggacc agtgacgaag   5460
```

-continued gcttgagcga gggcgtgcaa gattccgaat accgcaagcg acaggccgat catcgtcgcg 5520
ctccagcgaa agcggtcctc gccgaaaatg acccagagcg ctgccggcac ctgtcctacg 5580
agttgcatga taaagaagac agtcataagt gcggcgacga tagtcatgcc ccgcgcccac 5640
cggaaggagc tgactgggtt gaaggctctc aagggcatcg gtcgagatcc cggtgcctaa 5700
tgagtgagct aacttacatt aattgcgttg cgctcactgc ccgctttcca gtcgggaaac 5760
ctgtcgtgcc agctgcatta atgaatcggc caacgcgcgg ggagaggcgg tttgcgtatt 5820
gggcgccagg gtggtttttc ttttcaccag tgagacgggc aacagctgat tgcccttcac 5880
cgcctggccc tgagagagtt gcagcaagcg gtccacgctg gtttgcccca gcaggcgaaa 5940
atcctgtttg atggtggtta acggcgggat ataacatgag ctgtcttcgg tatcgtcgta 6000
tcccactacc gagatatccg caccaacgcg cagcccggac tcggtaatgg cgcgcattgc 6060
gcccagcgcc atctgatcgt tggcaaccag catcgcagtg ggaacgatgc cctcattcag 6120
catttgcatg gtttgttgaa aaccggacat ggcactccag tcgccttccc gttccgctat 6180
cggctgaatt tgattgcgag tgagatattt atgccagcca gccagacgca gacgcgccga 6240
gacagaactt aatgggcccg ctaacagcgc gatttgctgg tgacccaatg cgaccagatg 6300
ctccacgccc agtcgcgtac cgtcttcatg ggagaaaata atactgttga tgggtgtctg 6360
gtcagagaca tcaagaaata acgccggaac attagtgcag gcagcttcca cagcaatggc 6420
atcctggtca tccagcggat agttaatgat cagcccactg acgcgttgcg cgagaagatt 6480
gtgcaccgcc gctttacagg cttcgacgcc gcttcgttct accatcgaca ccaccacgct 6540
ggcacccagt tgatcggcgc gagatttaat cgccgcgaca atttgcgacg gcgcgtgcag 6600
ggccagactg gaggtggcaa cgccaatcag caacgactgt ttgcccgcca gttgttgtgc 6660
cacgcggttg ggaatgtaat tcagctccgc catcgccgct tccacttttt cccgcgtttt 6720
cgcagaaacg tggctggcct ggttcaccac gcgggaaacg gtctgataag agacaccggc 6780
atactctgcg acatcgtata acgttactgg tttcacattc accaccctga attgactctc 6840
ttccgggcgc tatcatgcca taccgcgaaa ggttttgcgc cattcgatgg tgtccgggat 6900
ctcgacgctc tcccttatgc gactcctgca ttaggaagca gcccagtagt aggttgaggc 6960
cgttgagcac cgccgccgca aggaatggtg catgcaagga gatggcgccc aacagtcccc 7020
cggccacggg gcctgccacc atacccacgc cgaaacaagc gctcatgagc ccgaagtggc 7080
gagcccgatc ttccccatcg gtgatgtcgg cgatataggc gccagcaacc gcacctgtgg 7140
cgccggtgat gccggccacg atgcgtccgg cgtagaggat cgagatctcg atcccgcgaa 7200
at 7202

<210> SEQ ID NO 16
<211> LENGTH: 5075
<212> TYPE: DNA
<213> ORGANISM: Artificial Sequence
<220> FEATURE:
<223> OTHER INFORMATION: pVTSD4 Vector

<400> SEQUENCE: 16
cgagggcaaa ccatggctca ccatcatcat catcattctt ctggtgtaga tctgggtacc 60
gagaacctgt acttccaatc catggagacc gacgtccaca tatacctgcc gttcactatt 120
atttagtgaa atgagatatt atgatatttt ctgaattgtg attaaaaagg caactttatg 180
cccatgcaac agaaactata aaaaatacag agaatgaaaa gaaacagata gattttttag 240
ttctttaggc ccgtagtctg caaatccttt tatgattttc tatcaaacaa aagaggaaaa 300

```
tagaccagtt gcaatccaaa cgagagtcta atagaatgag gtcgaaaagt aaatcgcgcg    360
ggtttgttac tgataaagca ggcaagacct aaaatgtgta aagggcaaag tgtatacttt    420
ggcgtcaccc cttacatatt ttaggtcttt ttttattgtg cgtaactaac ttgccatctt    480
caaacaggag ggctggaaga agcagaccgc taacacagta cataaaaaag gagacatgaa    540
cgatgaacat caaaaagttt gcaaaacaag caacagtatt aacctttact accgcactgc    600
tggcaggagg cgcaactcaa gcgtttgcga aagaaacgaa ccaaaagcca tataaggaaa    660
catacggcat ttcccatatt acacgccatg atatgctgca aatccctgaa cagcaaaaaa    720
atgaaaaata taaagttcct gagttcgatt cgtccacaat taaaaatatc tcttctgcaa    780
aaggcctgga cgtttgggac agctggccat tacaaaacac tgacggcact gtcgcaaact    840
atcacggcta ccacatcgtc tttgcattag ccggagatcc taaaaatgcg gatgacacat    900
cgatttacat gttctatcaa aaagtcggcg aaacttctat tgacagctgg aaaaacgctg    960
gccgcgtctt taaagacagc gacaaattcg atgcaaatga ttctatccta aaagaccaaa   1020
cacaagaatg gtcaggttca gccacattta catctgacgg aaaaatccgt ttattctaca   1080
ctgatttctc cggtaaacat tacggcaaac aaacactgac aactgcacaa gttaacgtat   1140
cagcatcaga cagctctttg aacatcaacg gtgtagagga ttataaatca atctttgacg   1200
gtgacggaaa aacgtatcaa aatgtacagc agttcatcga tgaaggcaac tacagctcag   1260
gcgacaacca tacgctgaga gatcctcact acgtagaaga taaaggccac aaatacttag   1320
tatttgaagc aaacactgga actgaagatg gctaccaagg cgaagaatct ttatttaaca   1380
aagcatacta tggcaaaagc acatcattct tccgtcaaga aagtcaaaaa cttctgcaaa   1440
gcgataaaaa acgcacggct gagttagcaa acggcgctct cggtatgatt gagctaaacg   1500
atgattacac actgaaaaaa gtgatgaaac cgctgattgc atctaacaca gtaacagatg   1560
aaattgaacg cgcgaacgtc tttaaaatga acggcaaatg gtacctgttc actgactccc   1620
gcggatcaaa aatgacgatt gacggcatta cgtctaacga tatttacatg cttggttatg   1680
tttctaattc tttaactggc ccatacaagc cgctgaacaa aactggcctt gtgttaaaaa   1740
tggatcttga tcctaacgat gtaaccttta cttactcaca cttcgctgta cctcaagcga   1800
aaggaaacaa tgtcgtgatt acaagctata tgacaaacag aggattctac gcagacaaac   1860
aatcaacgtt tgcgcctagc ttcctgctga acatcaaagg caagaaaaca tctgttgtca   1920
aagacagcat ccttgaacaa ggacaattaa cagttaacaa ataaaaacgc aaaagaaaat   1980
gccgatatcc tattggcatt gacggtctca agtaataagg atccgacctg tgaagtgaaa   2040
aatggcgcac attgtgcgac attttttttg tctgccgttt accgctactg cgtcacggat   2100
ctccacgcgc cctgtagcgg cgcattaagc gcggcgggtg tggtggttac gcgcagcgtg   2160
accgctacac ttgccagcgc cctagcgccc gctcctttcg ctttcttccc ttcctttctc   2220
gccacgttcg ccggctttcc ccgtcaagct ctaaatcggg ggctcccttt agggttccga   2280
tttagtgctt tacggcacct cgaccccaaa aaacttgatt agggtgatgg ttcacgtagt   2340
gggccatcgc cctgatagac ggtttttcgc cctttgacgt tggagtccac gttctttaat   2400
agtggactct tgttccaaac tggaacaaca ctcaacccta tctcggtcta ttcttttgat   2460
ttataaggga ttttgccgat ttcggcctat tggttaaaaa atgagctgat ttaacaaaaa   2520
tttaacgcga attttaacaa aatattaacg cttacaattt caggtggcac ttttcgggga   2580
aatgtgcgcg gaacccctat ttgtttattt ttctaaatac attcaaatat gtatccgctc   2640
```

```
atgagacaat aaccctgata aatgcttcaa taatattgaa aaaggaagag tatgagccat   2700
attcaacggg aaacgtcttg ctctaggccg cgattaaatt ccaacatgga tgctgattta   2760
tatgggtata aatgggctcg cgataatgtc gggcaatcag gtgcgacaat ctatcgattg   2820
tatgggaagc ccgatgcgcc agagttgttt ctgaaacatg gcaaaggtag cgttgccaat   2880
gatgttacag atgagatggt cagactaaac tggctgacgg aatttatgcc tcttccgacc   2940
atcaagcatt ttatccgtac tcctgatgat gcatggttac tcaccactgc gatccccggg   3000
aaaacagcat tccaggtatt agaagaatat cctgattcag gtgaaaatat tgttgatgcg   3060
ctggcagtgt tcctgcgccg gttgcattcg attcctgttt gtaattgtcc ttttaacagc   3120
gatcgcgtat ttcgtctcgc tcaggcgcaa tcacgaatga ataacggttt ggttgatgcg   3180
agtgattttg atgacgagcg taatggctgg cctgttgaac aagtctggaa agaaatgcat   3240
aaacttttgc cattctcacc ggattcagtc gtcactcatg gtgatttctc acttgataac   3300
cttatttttg acgaggggaa attaataggt tgtattgatg ttggacgagt cggaatcgca   3360
gaccgatacc aggatcttgc catcctatgg aactgcctcg gtgagttttc tccttcatta   3420
cagaaacggc tttttcaaaa atatggtatt gataatcctg atatgaataa attgcagttt   3480
catttgatgc tcgatgagtt tttctaagaa ttaatgatgt ctcgtttaga taaaagtaaa   3540
gtgattaaca gcgcattaga gctgcttaat gaggtcggaa tcgaaggttt aacaacccgt   3600
aaactcgccc agaagctagg tgtagagcag cctacattgt attggcatgt aaaaaataag   3660
cgggctttgc tcgacgcctt agccattgag atgttagata ggcaccatac tcacttttgc   3720
cctttagaag gggaaagctg gcaagatttt ttacgtaata acgctaaaag ttttagatgt   3780
gctttactaa gtcatcgcga tggagcaaaa gtacatttag gtacacggcc tacagaaaaa   3840
cagtatgaaa ctctcgaaaa tcaattagcc tttttatgcc aacaaggttt ttcactagag   3900
aatgcattat atgcactcag cgcagtgggg cattttactt taggttgcgt attggaagat   3960
caagagcatc aagtcgctaa agaagaaagg gaaacaccta ctactgatag tatgccgcca   4020
ttattacgac aagctatcga attatttgat caccaaggtg cagagccagc cttcttattc   4080
ggccttgaat tgatcatatg cggattagaa aaacaactta aatgtgaaag tgggtcttaa   4140
aagcagcata accttttttcc gtgatggtaa cttcactagt ttaaaaggat ctaggtgaag   4200
atcctttttg ataatctcat gaccaaaatc ccttaacgtg agttttcgtt ccactgagcg   4260
tcagaccccg tagaaaagat caaaggatct tcttgagatc cttttttttct gcgcgtaatc   4320
tgctgcttgc aaacaaaaaa accaccgcta ccagcggtgg tttgtttgcc ggatcaagag   4380
ctaccaactc tttttccgaa ggtaactggc ttcagcagag cgcagatacc aaatactgtc   4440
cttctagtgt agccgtagtt aggccaccac ttcaagaact ctgtagcacc gcctacatac   4500
ctcgctctgc taatcctgtt accagtggct gctgccagtg gcgataagtc gtgtcttacc   4560
gggttggact caagacgata gttaccggat aaggcgcagc ggtcgggctg aacggggggt   4620
tcgtgcacac agcccagctt ggagcgaacg acctacaccg aactgagata cctacagcgt   4680
gagctatgag aaagcgccac gcttcccgaa gggagaaagg cggacaggta tccggtaagc   4740
ggcagggtcg gaacaggaga gcgcacgagg gagcttccag ggggaaacgc ctggtatctt   4800
tatagtcctg tcgggtttcg ccacctctga cttgagcgtc gatttttgtg atgctcgtca   4860
gggggggcgga gcctatggaa aaacgccagc aacgcggcct ttttacggtt cctggccttt   4920
tgctggcctt ttgctcacat gacccgacac catcgaatgg ccagatgatt aattcctaat   4980
ttttgttgac actctatcat tgatagagtt attttaccac tccctatcag tgatagagaa   5040
```

-continued aagtgaaatg aatagttcga caaaaatcta gataa 5075

<210> SEQ ID NO 17
<211> LENGTH: 7208
<212> TYPE: DNA
<213> ORGANISM: Artificial Sequence
<220> FEATURE:
<223> OTHER INFORMATION: pVTSD5 Vector

<400> SEQUENCE: 17
taatacgact cactataggg gaattgtgag cggataacaa ttcccctcta gaaataattt 60
tgtttaactt taagaaggag atatatccat ggagaccgac gtccacatat acctgccgtt 120
cactattatt tagtgaaatg agatattatg atattttctg aattgtgatt aaaaaggcaa 180
ctttatgccc atgcaacaga aactataaaa aatacagaga atgaaaagaa acagatagat 240
tttttagttc tttaggcccg tagtctgcaa atccttttat gattttctat caaacaaaag 300
aggaaaatag accagttgca atccaaacga gagtctaata gaatgaggtc gaaaagtaaa 360
tcgcgcgggt ttgttactga taaagcaggc aagacctaaa atgtgtaaag ggcaaagtgt 420
atactttggc gtcacccctt acatatttta ggtctttttt tattgtgcgt aactaacttg 480
ccatcttcaa acaggagggc tggaagaagc agaccgctaa cacagtacat aaaaaaggag 540
acatgaacga tgaacatcaa aaagtttgca aaacaagcaa cagtattaac ctttactacc 600
gcactgctgg caggaggcgc aactcaagcg tttgcgaaag aaacgaacca aaagccatat 660
aaggaaacat acggcatttc ccatattaca cgccatgata tgctgcaaat ccctgaacag 720
caaaaaaatg aaaaatataa agttcctgag ttcgattcgt ccacaattaa aaatatctct 780
tctgcaaaag gcctggacgt ttgggacagc tggccattac aaaacactga cggcactgtc 840
gcaaactatc acggctacca catcgtcttt gcattagccg gagatcctaa aaatgcggat 900
gacacatcga tttacatgtt ctatcaaaaa gtcggcgaaa cttctattga cagctggaaa 960
aacgctggcc gcgtctttaa agacagcgac aaattcgatg caaatgattc tatcctaaaa 1020
gaccaaacac aagaatggtc aggttcagcc acatttacat ctgacggaaa aatccgttta 1080
ttctacactg atttctccgg taaacattac ggcaaacaaa cactgacaac tgcacaagtt 1140
aacgtatcag catcagacag ctctttgaac atcaacggtg tagaggatta taaatcaatc 1200
tttgacggtg acggaaaaac gtatcaaaat gtacagcagt tcatcgatga aggcaactac 1260
agctcaggcg acaaccatac gctgagagat cctcactacg tagaagataa aggccacaaa 1320
tacttagtat ttgaagcaaa cactggaact gaagatggct accaaggcga agaatcttta 1380
tttaacaaag catactatgg caaaagcaca tcattcttcc gtcaagaaag tcaaaaactt 1440
ctgcaaagcg ataaaaaacg cacggctgag ttagcaaacg gcgctctcgg tatgattgag 1500
ctaaacgatg attacacact gaaaaaagtg atgaaaccgc tgattgcatc taacacagta 1560
acagatgaaa ttgaacgcgc gaacgtcttt aaaatgaacg gcaaatggta cctgttcact 1620
gactcccgcg gatcaaaaat gacgattgac ggcattacgt ctaacgatat ttacatgctt 1680
ggttatgttt ctaattcttt aactggccca tacaagccgc tgaacaaaac tggccttgtg 1740
ttaaaaatgg atcttgatcc taacgatgta acctttactt actcacactt cgctgtacct 1800
caagcgaaag gaaacaatgt cgtgattaca agctatatga caaacagagg attctacgca 1860
gacaaacaat caacgtttgc gcctagcttc ctgctgaaca tcaaaggcaa gaaaacatct 1920
gttgtcaaag acagcatcct tgaacaagga caattaacag ttaacaaata aaaacgcaaa 1980

-continued

```
agaaaatgcc gatatcctat tggcattgac ggtctccagt actggagcca cccgcagttc   2040
gaaaaataag tcagcggccg cactcgagca ccaccaccac caccactgag atccggctgc   2100
taacaaagcc cgaaaggaag ctgagttggc tgctgccacc gctgagcaat aactagcata   2160
accccttggg gcctctaaac gggtcttgag gggttttttg ctgaaaggag gaactatatc   2220
cggattggcg aatgggacgc gccctgtagc ggcgcattaa gcgcggcggg tgtggtggtt   2280
acgcgcagcg tgaccgctac acttgccagc gccctagcgc ccgctccttt cgctttcttc   2340
ccttcctttc tcgccacgtt cgccggcttt ccccgtcaag ctctaaatcg ggggctccct   2400
ttagggttcc gatttagtgc tttacggcac ctcgacccca aaaaacttga ttagggtgat   2460
ggttcacgta gtgggccatc gccctgatag acggtttttc gccctttgac gttggagtcc   2520
acgttcttta atagtggact cttgttccaa actggaacaa cactcaaccc tatctcggtc   2580
tattcttttg atttataagg gattttgccg atttcggcct attggttaaa aaatgagctg   2640
atttaacaaa aatttaacgc gaattttaac aaaatattaa cgtttacaat ttcaggtggc   2700
acttttcggg gaaatgtgcg cggaacccct atttgtttat ttttctaaat acattcaaat   2760
atgtatccgc tcatgaatta attcttagaa aaactcatcg agcatcaaat gaaactgcaa   2820
tttattcata tcaggattat caataccata tttttgaaaa agccgtttct gtaatgaagg   2880
agaaaactca ccgaggcagt tccataggat ggcaagatcc tggtatcggt ctgcgattcc   2940
gactcgtcca acatcaatac aacctattaa tttcccctcg tcaaaaataa ggttatcaag   3000
tgagaaatca ccatgagtga cgactgaatc cggtgagaat ggcaaaagtt tatgcatttc   3060
tttccagact tgttcaacag gccagccatt acgctcgtca tcaaaatcac tcgcatcaac   3120
caaaccgtta ttcattcgtg attgcgcctg agcgagacga aatacgcgat cgctgttaaa   3180
aggacaatta caaacaggaa tcgaatgcaa ccggcgcagg aacactgcca gcgcatcaac   3240
aatattttca cctgaatcag gatattcttc taatacctgg aatgctgttt tcccggggat   3300
cgcagtggtg agtaaccatg catcatcagg agtacggata aaatgcttga tggtcggaag   3360
aggcataaat tccgtcagcc agtttagtct gaccatctca tctgtaacat cattggcaac   3420
gctacctttg ccatgtttca gaaacaactc tggcgcatcg ggcttcccat acaatcgata   3480
gattgtcgca cctgattgcc cgacattatc gcgagcccat ttatacccat ataaatcagc   3540
atccatgttg gaatttaatc gcggcctaga gcaagacgtt tcccgttgaa tatggctcat   3600
aacacccctt gtattactgt ttatgtaagc agacagtttt attgttcatg accaaaatcc   3660
cttaacgtga gttttcgttc cactgagcgt cagaccccgt agaaaagatc aaaggatctt   3720
cttgagatcc tttttttctg cgcgtaatct gctgcttgca aacaaaaaaa ccaccgctac   3780
cagcggtggt ttgtttgccg gatcaagagc taccaactct ttttccgaag gtaactggct   3840
tcagcagagc gcagatacca aatactgtcc ttctagtgta gccgtagtta ggccaccact   3900
tcaagaactc tgtagcaccg cctacatacc tcgctctgct aatcctgtta ccagtggctg   3960
ctgccagtgg cgataagtcg tgtcttaccg ggttggactc aagacgatag ttaccggata   4020
aggcgcagcg gtcgggctga acggggggtt cgtgcacaca gcccagcttg gagcgaacga   4080
cctacaccga actgagatac ctacagcgtg agctatgaga aagcgccacg cttcccgaag   4140
ggagaaaggc ggacaggtat ccggtaagcg gcagggtcgg aacaggagag cgcacgaggg   4200
agcttccagg gggaaacgcc tggtatcttt atagtcctgt cgggtttcgc cacctctgac   4260
ttgagcgtcg atttttgtga tgctcgtcag gggggcggag cctatggaaa aacgccagca   4320
acgcggcctt tttacggttc ctggcctttt gctggccttt tgctcacatg ttctttcctg   4380
```

-continued

```
cgttatcccc tgattctgtg gataaccgta ttaccgcctt tgagtgagct gataccgctc   4440
gccgcagccg aacgaccgag cgcagcgagt cagtgagcga ggaagcggaa gagcgcctga   4500
tgcggtattt tctccttacg catctgtgcg gtatttcaca ccgcatatat ggtgcactct   4560
cagtacaatc tgctctgatg ccgcatagtt aagccagtat acactccgct atcgctacgt   4620
gactgggtca tggctgcgcc ccgacacccg ccaacacccg ctgacgcgcc ctgacgggct   4680
tgtctgctcc cggcatccgc ttacagacaa gctgtgaccg tctccgggag ctgcatgtgt   4740
cagaggtttt caccgtcatc accgaaacgc gcgaggcagc tgcggtaaag ctcatcagcg   4800
tggtcgtgaa gcgattcaca gatgtctgcc tgttcatccg cgtccagctc gttgagtttc   4860
tccagaagcg ttaatgtctg gcttctgata aagcgggcca tgttaagggc ggtttttttcc   4920
tgtttggtca ctgatgcctc cgtgtaaggg ggatttctgt tcatgggggt aatgataccg   4980
atgaaacgag agaggatgct cacgatacgg gttactgatg atgaacatgc ccggttactg   5040
gaacgttgtg agggtaaaca actggcggta tggatgcggc gggaccagag aaaaatcact   5100
cagggtcaat gccagcgctt cgttaataca gatgtaggtg ttccacaggg tagccagcag   5160
catcctgcga tgcagatccg gaacataatg gtgcagggcg ctgacttccg cgtttccaga   5220
ctttacgaaa cacggaaacc gaagaccatt catgttgttg ctcaggtcgc agacgttttg   5280
cagcagcagt cgcttcacgt tcgctcgcgt atcggtgatt cattctgcta accagtaagg   5340
caaccccgcc agcctagccg ggtcctcaac gacaggagca cgatcatgcg cacccgtggg   5400
gccgccatgc cggcgataat ggcctgcttc tcgccgaaac gtttggtggc gggaccagtg   5460
acgaaggctt gagcgagggc gtgcaagatt ccgaataccg caagcgacag gccgatcatc   5520
gtcgcgctcc agcgaaagcg gtcctcgccg aaaatgaccc agagcgctgc cggcacctgt   5580
cctacgagtt gcatgataaa gaagacagtc ataagtgcgg cgacgatagt catgccccgc   5640
gcccaccgga aggagctgac tgggttgaag gctctcaagg gcatcggtcg agatcccggt   5700
gcctaatgag tgagctaact tacattaatt gcgttgcgct cactgcccgc tttccagtcg   5760
ggaaacctgt cgtgccagct gcattaatga atcggccaac gcgcggggag aggcggtttg   5820
cgtattgggc gccagggtgg tttttctttt caccagtgag acgggcaaca gctgattgcc   5880
cttcaccgcc tggccctgag agagttgcag caagcggtcc acgctggttt gccccagcag   5940
gcgaaaatcc tgtttgatgg tggttaacgg cgggatataa catgagctgt cttcggtatc   6000
gtcgtatccc actaccgaga tatccgcacc aacgcgcagc ccggactcgg taatggcgcg   6060
cattgcgccc agcgccatct gatcgttggc aaccagcatc gcagtgggaa cgatgccctc   6120
attcagcatt tgcatggttt gttgaaaacc ggacatggca ctccagtcgc cttcccgttc   6180
cgctatcggc tgaatttgat tgcgagtgag atatttatgc cagccagcca gacgcagacg   6240
cgccgagaca gaacttaatg ggcccgctaa cagcgcgatt tgctggtgac ccaatgcgac   6300
cagatgctcc acgcccagtc gcgtaccgtc ttcatgggag aaaataatac tgttgatggg   6360
tgtctggtca gagacatcaa gaaataacgc cggaacatta gtgcaggcag cttccacagc   6420
aatggcatcc tggtcatcca gcggatagtt aatgatcagc ccactgacgc gttgcgcgag   6480
aagattgtgc accgccgctt tacaggcttc gacgccgctt cgttctacca tcgacaccac   6540
cacgctggca cccagttgat cggcgcgaga tttaatcgcc gcgacaattt gcgacggcgc   6600
gtgcagggcc agactggagg tggcaacgcc aatcagcaac gactgtttgc ccgccagttg   6660
ttgtgccacg cggttgggaa tgtaattcag ctccgccatc gccgcttcca ctttttcccg   6720
```

```
cgttttcgca gaaacgtggc tggcctggtt caccacgcgg gaaacggtct gataagagac   6780

accggcatac tctgcgacat cgtataacgt tactggtttc acattcacca ccctgaattg   6840

actctcttcc gggcgctatc atgccatacc gcgaaaggtt ttgcgccatt cgatggtgtc   6900

cgggatctcg acgctctccc ttatgcgact cctgcattag gaagcagccc agtagtaggt   6960

tgaggccgtt gagcaccgcc gccgcaagga atggtgcatg caaggagatg gcgcccaaca   7020

gtcccccggc cacggggcct gccaccatac ccacgccgaa acaagcgctc atgagcccga   7080

agtggcgagc ccgatcttcc ccatcggtga tgtcggcgat ataggcgcca gcaaccgcac   7140

ctgtggcgcc ggtgatgccg gccacgatgc gtccggcgta gaggatcgag atctcgatcc   7200

cgcgaaat                                                            7208
```

```
<210> SEQ ID NO 18
<211> LENGTH: 7057
<212> TYPE: DNA
<213> ORGANISM: Artificial Sequence
<220> FEATURE:
<223> OTHER INFORMATION: pVTSD6 Vector

<400> SEQUENCE: 18
```

```
gcgcgaggca gcagatcaat tcgcgcgcga aggcgaagcg gcatgcataa tgtgcctgtc     60

aaatggacga agcagggatt ctgcaaaccc tatgctactc cgtcaagccg tcaattgtct    120

gattcgttac caattatgac aacttgacgg ctacatcatt cactttttct tcacaaccgg    180

cacggaactc gctcgggctg gccccggtgc atttttaaa tacccgcgag aaatagagtt    240

gatcgtcaaa accaacattg cgaccgacgg tggcgatagg catccgggtg gtgctcaaaa    300

gcagcttcgc ctggctgata cgttggtcct cgcgccagct taagacgcta atccctaact    360

gctggcggaa aagatgtgac agacgcgacg gcgacaagca aacatgctgt gcgacgctgg    420

cgatatcaaa attgctgtct gccaggtgat cgctgatgta ctgacaagcc tcgcgtaccc    480

gattatccat cggtggatgg agcgactcgt taatcgcttc catgcgccgc agtaacaatt    540

gctcaagcag atttatcgcc agcagctccg aatagcgccc ttccccttgc ccggcgttaa    600

tgatttgccc aaacaggtcg ctgaaatgcg gctggtgcgc ttcatccggg cgaaagaacc    660

ccgtattggc aaatattgac ggccagttaa gccattcatg ccagtaggcg cgcggacgaa    720

agtaaaccca ctggtgatac cattcgcgag cctccggatg acgaccgtag tgatgaatct    780

ctcctggcgg gaacagcaaa atatcacccg gtcggcaaac aaattctcgt ccctgatttt    840

tcaccacccc ctgaccgcga atggtgagat tgagaatata acctttcatt cccagcggtc    900

ggtcgataaa aaaatcgaga taaccgttgg cctcaatcgg cgttaaaccc gccaccagat    960

gggcattaaa cgagtatccc ggcagcaggg gatcattttg cgcttcagcc atacttttca   1020

tactcccgcc attcagagaa gaaaccaatt gtccatattg catcagacat tgccgtcact   1080

gcgtctttta ctggctcttc tcgctaacca aaccggtaac cccgcttatt aaaagcattc   1140

tgtaacaaag cgggaccaaa gccatgacaa aaacgcgtaa caaaagtgtc tataatcacg   1200

gcagaaaagt ccacattgat tatttgcacg gcgtcacact ttgctatgcc atagcatttt   1260

tatccataag attagcggat cctacctgac gctttttatc gcaactctct actgtttctc   1320

catacccgtt tttttgggct agaaataatt ttgtttaact ttaagaagga gatatacata   1380

cccggatctg ataaaattat tcatctgact gatgattctt ttgatactga tgtacttaag   1440

gcagatggtg caatcctggt tgatttctgg gcacactggt gcggtccgtg caaaatgatc   1500

gctccgattc tggatgaaat cgctgacgaa tatcagggca aactgaccgt tgcaaaactg   1560
```

-continued

```
aacatcgatc acaacccggg cactgcgccg aaatatggca tccgtggtat cccgactctg   1620
ctgctgttca aaaacggtga agtggcggca accaaagtgg gtgcactgtc taaaggtcag   1680
ttgaaagagt tcctcgacgc taacctggcc ggctctggat ccggtgatga cgatgacaag   1740
gccatggaga ccgacgtcca catatacctg ccgttcacta ttatttagtg aaatgagata   1800
ttatgatatt ttctgaattg tgattaaaaa ggcaacttta tgcccatgca acagaaacta   1860
taaaaaatac agagaatgaa aagaaacaga tagatttttt agttctttag gcccgtagtc   1920
tgcaaatcct tttatgattt tctatcaaac aaaagaggaa aatagaccag ttgcaatcca   1980
aacgagagtc taatagaatg aggtcgaaaa gtaaatcgcg cgggtttgtt actgataaag   2040
caggcaagac ctaaaatgtg taaagggcaa agtgtatact ttggcgtcac cccttacata   2100
ttttaggtct ttttttattg tgcgtaacta acttgccatc ttcaaacagg agggctggaa   2160
gaagcagacc gctaacacag tacataaaaa aggagacatg aacgatgaac atcaaaaagt   2220
ttgcaaaaca agcaacagta ttaaccttta ctaccgcact gctggcagga ggcgcaactc   2280
aagcgtttgc gaaagaaacg aaccaaaagc catataagga aacatacggc atttcccata   2340
ttacacgcca tgatatgctg caaatccctg aacagcaaaa aatgaaaaaa tataaagttc   2400
ctgagttcga ttcgtccaca attaaaaata tctcttctgc aaaaggcctg gacgtttggg   2460
acagctggcc attacaaaac actgacggca ctgtcgcaaa ctatcacggc taccacatcg   2520
tctttgcatt agccggagat cctaaaaatg cggatgacac atcgatttac atgttctatc   2580
aaaaagtcgg cgaaacttct attgacagct ggaaaaacgc tggccgcgtc tttaaagaca   2640
gcgacaaatt cgatgcaaat gattctatcc taaaagacca aacacaagaa tggtcaggtt   2700
cagccacatt tacatctgac ggaaaaatcc gtttattcta cactgatttc tccggtaaac   2760
attacggcaa acaaacactg acaactgcac aagttaacgt atcagcatca gacagctctt   2820
tgaacatcaa cggtgtagag gattataaat caatctttga cggtgacgga aaaacgtatc   2880
aaaatgtaca gcagttcatc gatgaaggca actacagctc aggcgacaac catacgctga   2940
gagatcctca ctacgtagaa gataaaggcc acaaatactt agtatttgaa gcaaacactg   3000
gaactgaaga tggctaccaa ggcgaagaat ctttatttaa caaagcatac tatggcaaaa   3060
gcacatcatt cttccgtcaa gaaagtcaaa aacttctgca aagcgataaa aaacgcacgg   3120
ctgagttagc aaacggcgct ctcggtatga ttgagctaaa cgatgattac acactgaaaa   3180
aagtgatgaa accgctgatt gcatctaaca cagtaacaga tgaaattgaa cgcgcgaacg   3240
tctttaaaat gaacggcaaa tggtacctgt tcactgactc ccgcggatca aaaatgacga   3300
ttgacggcat tacgtctaac gatatttaca tgcttggtta tgtttctaat tctttaactg   3360
gcccatacaa gccgctgaac aaaactggcc ttgtgttaaa aatggatctt gatcctaacg   3420
atgtaacctt tacttactca cacttcgctg tacctcaagc gaaaggaaac aatgtcgtga   3480
ttacaagcta tatgacaaac agaggattct acgcagacaa acaatcaacg tttgcgccta   3540
gcttcctgct gaacatcaaa ggcaagaaaa catctgttgt caaagacagc atccttgaac   3600
aaggacaatt aacagttaac aaataaaaac gcaaaagaaa atgccgatat cctattggca   3660
ttgacggtct ccagtactgg agccacccgc agttcgaaaa ataagtcagc ggccgcactc   3720
gagcaccacc accaccacca ctgagatccg gctgctaaca aagcccgaaa ggaagctgag   3780
ttggctgctg ccaccgctga gcaataacta gcataacccc ttggggcctc taaacgggtc   3840
ttgaggggtt ttttgctgaa aggaggaact atatccggat tggcgaatgg gacgcgccct   3900
```

```
gtagcggcgc attaagcgcg gcgggtgtgg tggttacgcg cagcgtgacc gctacacttg   3960
ccagcgccct agcgcccgct cctttcgctt tcttcccttc ctttctcgcc acgttcgccg   4020
gctttccccg tcaagctcta aatcgggggc tccctttagg gttccgattt agtgctttac   4080
ggcacctcga ccccaaaaaa cttgattagg gtgatggttc acgtagtggg ccatcgccct   4140
gatagacggt ttttcgccct ttgacgttgg agtccacgtt ctttaatagt ggactcttgt   4200
tccaaactgg aacaacactc aaccctatct cggtctattc ttttgattta taagggattt   4260
tgccgatttc ggcctattgg ttaaaaaatg agctgattta acaaaaattt aacgcgaatt   4320
ttaacaaaat attaacgttt acaatttcag gtggcacttt tcggggaaat gtgcgcggaa   4380
cccctatttg tttatttttc taaatacatt caaatatgta tccgctcatg aattaattct   4440
tagaaaaact catcgagcat caaatgaaac tgcaatttat tcatatcagg attatcaata   4500
ccatattttt gaaaaagccg tttctgtaat gaaggagaaa actcaccgag gcagttccat   4560
aggatggcaa gatcctggta tcggtctgcg attccgactc gtccaacatc aatacaacct   4620
attaatttcc cctcgtcaaa aataaggtta tcaagtgaga aatcaccatg agtgacgact   4680
gaatccggtg agaatggcaa aagtttatgc atttctttcc agacttgttc aacaggccag   4740
ccattacgct cgtcatcaaa atcactcgca tcaaccaaac cgttattcat tcgtgattgc   4800
gcctgagcga gacgaaatac gcgatcgctg ttaaaaggac aattacaaac aggaatcgaa   4860
tgcaaccggc gcaggaacac tgccagcgca tcaacaatat tttcacctga atcaggatat   4920
tcttctaata cctggaatgc tgttttcccg gggatcgcag tggtgagtaa ccatgcatca   4980
tcaggagtac ggataaaatg cttgatggtc ggaagaggca taaattccgt cagccagttt   5040
agtctgacca tctcatctgt aacatcattg gcaacgctac ctttgccatg tttcagaaac   5100
aactctggcg catcgggctt cccatacaat cgatagattg tcgcacctga ttgcccgaca   5160
ttatcgcgag cccatttata cccatataaa tcagcatcca tgttggaatt taatcgcggc   5220
ctagagcaag acgtttcccg ttgaatatgg ctcataacac cccttgtatt actgtttatg   5280
taagcagaca gttttattgt tcatgaccaa aatcccttaa cgtgagtttt cgttccactg   5340
agcgtcagac cccgtagaaa agatcaaagg atcttcttga gatccttttt ttctgcgcgt   5400
aatctgctgc ttgcaaacaa aaaaaccacc gctaccagcg gtggtttgtt tgccggatca   5460
agagctacca actctttttc cgaaggtaac tggcttcagc agagcgcaga taccaaatac   5520
tgtccttcta gtgtagccgt agttaggcca ccacttcaag aactctgtag caccgcctac   5580
atacctcgct ctgctaatcc tgttaccagt ggctgctgcc agtggcgata agtcgtgtct   5640
taccgggttg gactcaagac gatagttacc ggataaggcg cagcggtcgg gctgaacggg   5700
gggttcgtgc acacagccca gcttggagcg aacgacctac accgaactga gatacctaca   5760
gcgtgagcta tgagaaagcg ccacgcttcc cgaagggaga aaggcggaca ggtatccggt   5820
aagcggcagg gtcggaacag gagagcgcac gagggagctt ccagggggaa acgcctggta   5880
tctttatagt cctgtcgggt ttcgccacct ctgacttgag cgtcgatttt tgtgatgctc   5940
gtcagggggg cggagcctat ggaaaaacgc cagcaacgcg gcctttttac ggttcctggc   6000
cttttgctgg ccttttgctc acatgttctt tcctgcgtta tcccctgatt ctgtggataa   6060
ccgtattacc gcctttgagt gagctgatac cgctcgccgc agccgaacga ccgagcgcag   6120
cgagtcagtg agcgaggaag cggaagagcg cctgatgcgg tattttctcc ttacgcatct   6180
gtgcggtatt tcacaccgca tatatggtgc actctcagta caatctgctc tgatgccgca   6240
tagttaagcc agtatacact ccgctatcgc tacgtgactg ggtcatggct gcgccccgac   6300
```

acccgccaac acccgctgac gcgccctgac gggcttgtct gctcccggca tccgcttaca 6360
gacaagctgt gaccgtctcc gggagctgca tgtgtcagag gttttcaccg tcatcaccga 6420
aacgcgcgag gcagctgcgg taaagctcat cagcgtggtc gtgaagcgat tcacagatgt 6480
ctgcctgttc atccgcgtcc agctcgttga gtttctccag aagcgttaat gtctggcttc 6540
tgataaagcg ggccatgtta agggcggttt tttcctgttt ggtcactgat gcctccgtgt 6600
aagggggatt tctgttcatg ggggtaatga taccgatgaa acgagagagg atgctcacga 6660
tacgggttac tgatgatgaa catgcccggt tactggaacg ttgtgagggt aaacaactgg 6720
cggtatggat gcggcgggac cagagaaaaa tcactcaggg tcaatgccag cgcttcgtta 6780
atacagatgt aggtgttcca cagggtagcc agcagcatcc tgcgatgcag atccggaaca 6840
taatggtgca gggcgctgac ttccgcgttt ccagacttta cgaaacacgg aaaccgaaga 6900
ccattcatgt tgttgctcag gtcgcagacg ttttgcagca gcagtcgctt cacgttcgct 6960
cgcgtatcgg tgattcattc tgctaaccag taaggcaacc ccgccagcct agccgggtcc 7020
tcaacgacag gagcacgatc atgcgcaccc gtgaaac 7057

<210> SEQ ID NO 19
<211> LENGTH: 6701
<212> TYPE: DNA
<213> ORGANISM: Artificial Sequence
<220> FEATURE:
<223> OTHER INFORMATION: pVTSD7 Vector

<400> SEQUENCE: 19
gcgcgaggca gcagatcaat tcgcgcgcga aggcgaagcg gcatgcataa tgtgcctgtc 60
aaatggacga agcagggatt ctgcaaaccc tatgctactc cgtcaagccg tcaattgtct 120
gattcgttac caattatgac aacttgacgg ctacatcatt cactttttct tcacaaccgg 180
cacggaactc gctcgggctg gccccggtgc attttttaaa tacccgcgag aaatagagtt 240
gatcgtcaaa accaacattg cgaccgacgg tggcgatagg catccgggtg gtgctcaaaa 300
gcagcttcgc ctggctgata cgttggtcct cgcgccagct taagacgcta atccctaact 360
gctggcggaa aagatgtgac agacgcgacg gcgacaagca aacatgctgt gcgacgctgg 420
cgatatcaaa attgctgtct gccaggtgat cgctgatgta ctgacaagcc tcgcgtaccc 480
gattatccat cggtggatgg agcgactcgt taatcgcttc catgcgccgc agtaacaatt 540
gctcaagcag atttatcgcc agcagctccg aatagcgccc ttccccttgc ccggcgttaa 600
tgatttgccc aaacaggtcg ctgaaatgcg gctggtgcgc ttcatccggg cgaaagaacc 660
ccgtattggc aaatattgac ggccagttaa gccattcatg ccagtaggcg cgcggacgaa 720
agtaaaccca ctggtgatac cattcgcgag cctccggatg acgaccgtag tgatgaatct 780
ctcctggcgg gaacagcaaa atatcacccg gtcggcaaac aaattctcgt ccctgatttt 840
tcaccacccc ctgaccgcga atggtgagat tgagaatata acctttcatt cccagcggtc 900
ggtcgataaa aaaatcgaga taaccgttgg cctcaatcgg cgttaaaccc gccaccagat 960
gggcattaaa cgagtatccc ggcagcaggg gatcattttg cgcttcagcc atacttttca 1020
tactcccgcc attcagagaa gaaaccaatt gtccatattg catcagacat tgccgtcact 1080
gcgtctttta ctggctcttc tcgctaacca aaccggtaac cccgcttatt aaaagcattc 1140
tgtaacaaag cgggaccaaa gccatgacaa aaacgcgtaa caaaagtgtc tataatcacg 1200
gcagaaaagt ccacattgat tatttgcacg gcgtcacact ttgctatgcc atagcatttt 1260

-continued

```
tatccataag attagcggat cctacctgac gctttttatc gcaactctct actgtttctc   1320
catacccgtt tttttgggct agaaataatt ttgtttaact ttaagaagga gatatacata   1380
cccatccatg gagaccgacg tccacatata cctgccgttc actattattt agtgaaatga   1440
gatattatga tattttctga attgtgatta aaaaggcaac tttatgccca tgcaacagaa   1500
actataaaaa atacagagaa tgaaaagaaa cagatagatt ttttagttct ttaggcccgt   1560
agtctgcaaa tccttttatg attttctatc aaacaaaaga ggaaaataga ccagttgcaa   1620
tccaaacgag agtctaatag aatgaggtcg aaaagtaaat cgcgcgggtt tgttactgat   1680
aaagcaggca agacctaaaa tgtgtaaagg gcaaagtgta tactttggcg tcacccctta   1740
catattttag gtcttttttt attgtgcgta actaacttgc catcttcaaa caggagggct   1800
ggaagaagca gaccgctaac acagtacata aaaaaggaga catgaacgat gaacatcaaa   1860
aagtttgcaa aacaagcaac agtattaacc tttactaccg cactgctggc aggaggcgca   1920
actcaagcgt ttgcgaaaga aacgaaccaa aagccatata aggaaacata cggcatttcc   1980
catattacac gccatgatat gctgcaaatc cctgaacagc aaaaaaatga aaaatataaa   2040
gttcctgagt tcgattcgtc cacaattaaa aatatctctt ctgcaaaagg cctggacgtt   2100
tgggacagct ggccattaca aaacactgac ggcactgtcg caaactatca cggctaccac   2160
atcgtctttg cattagccgg agatcctaaa aatgcggatg acacatcgat ttacatgttc   2220
tatcaaaaag tcggcgaaac ttctattgac agctggaaaa acgctggccg cgtctttaaa   2280
gacagcgaca aattcgatgc aaatgattct atcctaaaag accaaacaca agaatggtca   2340
ggttcagcca catttacatc tgacggaaaa atccgtttat tctacactga tttctccggt   2400
aaacattacg gcaaacaaac actgacaact gcacaagtta acgtatcagc atcagacagc   2460
tctttgaaca tcaacggtgt agaggattat aaatcaatct ttgacggtga cggaaaaacg   2520
tatcaaaatg tacagcagtt catcgatgaa ggcaactaca gctcaggcga caaccatacg   2580
ctgagagatc ctcactacgt agaagataaa ggccacaaat acttagtatt tgaagcaaac   2640
actggaactg aagatggcta ccaaggcgaa gaatctttat ttaacaaagc atactatggc   2700
aaaagcacat cattcttccg tcaagaaagt caaaaacttc tgcaaagcga taaaaaacgc   2760
acggctgagt tagcaaacgg cgctctcggt atgattgagc taaacgatga ttacacactg   2820
aaaaaagtga tgaaaccgct gattgcatct aacacagtaa cagatgaaat tgaacgcgcg   2880
aacgtcttta aaatgaacgg caaatggtac ctgttcactg actcccgcgg atcaaaaatg   2940
acgattgacg gcattacgtc taacgatatt tacatgcttg gttatgtttc taattcttta   3000
actggcccat acaagccgct gaacaaaact ggccttgtgt taaaaatgga tcttgatcct   3060
aacgatgtaa cctttactta ctcacacttc gctgtacctc aagcgaaagg aaacaatgtc   3120
gtgattacaa gctatatgac aaacagagga ttctacgcag acaaacaatc aacgtttgcg   3180
cctagcttcc tgctgaacat caaaggcaag aaaacatctg ttgtcaaaga cagcatcctt   3240
gaacaaggac aattaacagt taacaaataa aaacgcaaaa gaaaatgccg atatcctatt   3300
ggcattgacg gtctccagta ctggagccac ccgcagttcg aaaaataagt cagcggccgc   3360
actcgagcac caccaccacc accactgaga tccggctgct aacaaagccc gaaaggaagc   3420
tgagttggct gctgccaccg ctgagcaata actagcataa ccccttgggg cctctaaacg   3480
ggtcttgagg ggttttttgc tgaaaggagg aactatatcc ggattggcga atgggacgcg   3540
ccctgtagcg gcgcattaag cgcggcgggt gtggtggtta cgcgcagcgt gaccgctaca   3600
cttgccagcg ccctagcgcc cgctcctttc gctttcttcc cttcctttct cgccacgttc   3660
```

```
gccggctttc cccgtcaagc tctaaatcgg gggctccctt tagggttccg atttagtgct   3720
ttacggcacc tcgaccccaa aaaacttgat tagggtgatg gttcacgtag tgggccatcg   3780
ccctgataga cggtttttcg ccctttgacg ttggagtcca cgttctttaa tagtggactc   3840
ttgttccaaa ctggaacaac actcaaccct atctcggtct attcttttga tttataaggg   3900
attttgccga tttcggccta ttggttaaaa aatgagctga tttaacaaaa atttaacgcg   3960
aattttaaca aaatattaac gtttacaatt tcaggtggca cttttcgggg aaatgtgcgc   4020
ggaaccccta tttgtttatt tttctaaata cattcaaata tgtatccgct catgaattaa   4080
ttcttagaaa aactcatcga gcatcaaatg aaactgcaat ttattcatat caggattatc   4140
aataccatat ttttgaaaaa gccgtttctg taatgaagga gaaaactcac cgaggcagtt   4200
ccataggatg gcaagatcct ggtatcggtc tgcgattccg actcgtccaa catcaataca   4260
acctattaat ttcccctcgt caaaaataag gttatcaagt gagaaatcac catgagtgac   4320
gactgaatcc ggtgagaatg gcaaaagttt atgcatttct ttccagactt gttcaacagg   4380
ccagccatta cgctcgtcat caaaatcact cgcatcaacc aaaccgttat tcattcgtga   4440
ttgcgcctga gcgagacgaa atacgcgatc gctgttaaaa ggacaattac aaacaggaat   4500
cgaatgcaac cggcgcagga acactgccag cgcatcaaca atattttcac ctgaatcagg   4560
atattcttct aatacctgga atgctgtttt cccggggatc gcagtggtga gtaaccatgc   4620
atcatcagga gtacggataa aatgcttgat ggtcggaaga ggcataaatt ccgtcagcca   4680
gtttagtctg accatctcat ctgtaacatc attggcaacg ctacctttgc catgtttcag   4740
aaacaactct ggcgcatcgg gcttcccata caatcgatag attgtcgcac ctgattgccc   4800
gacattatcg cgagcccatt tatacccata taaatcagca tccatgttgg aatttaatcg   4860
cggcctagag caagacgttt cccgttgaat atggctcata acaccccttg tattactgtt   4920
tatgtaagca gacagtttta ttgttcatga ccaaaatccc ttaacgtgag ttttcgttcc   4980
actgagcgtc agaccccgta gaaaagatca aaggatcttc ttgagatcct ttttttctgc   5040
gcgtaatctg ctgcttgcaa acaaaaaaac caccgctacc agcggtggtt tgtttgccgg   5100
atcaagagct accaactctt tttccgaagg taactggctt cagcagagcg cagataccaa   5160
atactgtcct tctagtgtag ccgtagttag gccaccactt caagaactct gtagcaccgc   5220
ctacatacct cgctctgcta atcctgttac cagtggctgc tgccagtggc gataagtcgt   5280
gtcttaccgg gttggactca agacgatagt taccggataa ggcgcagcgg tcgggctgaa   5340
cggggggttc gtgcacacag cccagcttgg agcgaacgac ctacaccgaa ctgagatacc   5400
tacagcgtga gctatgagaa agcgccacgc ttcccgaagg gagaaaggcg gacaggtatc   5460
cggtaagcgg cagggtcgga acaggagagc gcacgaggga gcttccaggg ggaaacgcct   5520
ggtatcttta tagtcctgtc gggtttcgcc acctctgact tgagcgtcga tttttgtgat   5580
gctcgtcagg ggggcggagc ctatggaaaa acgccagcaa cgcggccttt ttacggttcc   5640
tggccttttg ctggcctttt gctcacatgt tctttcctgc gttatcccct gattctgtgg   5700
ataaccgtat taccgccttt gagtgagctg ataccgctcg ccgcagccga acgaccgagc   5760
gcagcgagtc agtgagcgag gaagcggaag agcgcctgat gcggtatttt ctccttacgc   5820
atctgtgcgg tatttcacac cgcatatatg gtgcactctc agtacaatct gctctgatgc   5880
cgcatagtta agccagtata cactccgcta tcgctacgtg actgggtcat ggctgcgccc   5940
cgacacccgc caacacccgc tgacgcgccc tgacgggctt gtctgctccc ggcatccgct   6000
```

```
tacagacaag ctgtgaccgt ctccgggagc tgcatgtgtc agaggttttc accgtcatca   6060

ccgaaacgcg cgaggcagct gcggtaaagc tcatcagcgt ggtcgtgaag cgattcacag   6120

atgtctgcct gttcatccgc gtccagctcg ttgagtttct ccagaagcgt taatgtctgg   6180

cttctgataa agcgggccat gttaagggcg gttttttcct gtttggtcac tgatgcctcc   6240

gtgtaagggg gatttctgtt catgggggta atgataccga tgaaacgaga gaggatgctc   6300

acgatacggg ttactgatga tgaacatgcc cggttactgg aacgttgtga gggtaaacaa   6360

ctggcggtat ggatgcggcg ggaccagaga aaaatcactc agggtcaatg ccagcgcttc   6420

gttaatacag atgtaggtgt tccacagggt agccagcagc atcctgcgat gcagatccgg   6480

aacataatgg tgcagggcgc tgacttccgc gtttccagac tttacgaaac acggaaaccg   6540

aagaccattc atgttgttgc tcaggtcgca gacgttttgc agcagcagtc gcttcacgtt   6600

cgctcgcgta tcggtgattc attctgctaa ccagtaaggc aaccccgcca gcctagccgg   6660

gtcctcaacg acaggagcac gatcatgcgc acccgtgaaa c                       6701
```

<210> SEQ ID NO 20
<211> LENGTH: 7051
<212> TYPE: DNA
<213> ORGANISM: Artificial Sequence
<220> FEATURE:
<223> OTHER INFORMATION: pVTSD8 Vector

<400> SEQUENCE: 20

```
gcgcgaggca gcagatcaat tcgcgcgcga aggcgaagcg gcatgcataa tgtgcctgtc     60

aaatggacga agcagggatt ctgcaaaccc tatgctactc cgtcaagccg tcaattgtct    120

gattcgttac caattatgac aacttgacgg ctacatcatt cactttttct tcacaaccgg    180

cacggaactc gctcgggctg gccccggtgc atttttttaaa tacccgcgag aaatagagtt    240

gatcgtcaaa accaacattg cgaccgacgg tggcgatagg catccgggtg gtgctcaaaa    300

gcagcttcgc ctggctgata cgttggtcct cgcgccagct taagacgcta atccctaact    360

gctggcggaa aagatgtgac agacgcgacg gcgacaagca aacatgctgt gcgacgctgg    420

cgatatcaaa attgctgtct gccaggtgat cgctgatgta ctgacaagcc tcgcgtaccc    480

gattatccat cggtggatgg agcgactcgt taatcgcttc catgcgccgc agtaacaatt    540

gctcaagcag atttatcgcc agcagctccg aatagcgccc ttccccttgc ccggcgttaa    600

tgatttgccc aaacaggtcg ctgaaatgcg gctggtgcgc ttcatccggg cgaaagaacc    660

ccgtattggc aaatattgac ggccagttaa gccattcatg ccagtaggcg cgcggacgaa    720

agtaaaccca ctggtgatac cattcgcgag cctccggatg acgaccgtag tgatgaatct    780

ctcctggcgg gaacagcaaa atatcacccg gtcggcaaac aaattctcgt ccctgatttt    840

tcaccacccc ctgaccgcga atggtgagat tgagaatata acctttcatt cccagcggtc    900

ggtcgataaa aaaatcgaga taaccgttgg cctcaatcgg cgttaaaccc gccaccagat    960

gggcattaaa cgagtatccc ggcagcaggg gatcattttg cgcttcagcc atacttttca   1020

tactcccgcc attcagagaa gaaaccaatt gtccatattg catcagacat tgccgtcact   1080

gcgtctttta ctggctcttc tcgctaacca aaccggtaac cccgcttatt aaaagcattc   1140

tgtaacaaag cgggaccaaa gccatgacaa aaacgcgtaa caaaagtgtc tataatcacg   1200

gcagaaaagt ccacattgat tatttgcacg gcgtcacact ttgctatgcc atagcatttt   1260

tatccataag attagcggat cctacctgac gctttttatc gcaactctct actgtttctc   1320

catacccgtt tttttgggct agaaataatt ttgtttaact ttaagaagga gatatacata   1380
```

```
cccggatctg ataaaattat tcatctgact gatgattctt ttgatactga tgtacttaag   1440
gcagatggtg caatcctggt tgatttctgg gcacactggt gcggtccgtg caaaatgatc   1500
gctccgattc tggatgaaat cgctgacgaa tatcagggca aactgaccgt tgcaaaactg   1560
aacatcgatc acaacccggg cactgcgccg aaatatggca tccgtggtat cccgactctg   1620
ctgctgttca aaaacggtga agtggcggca accaaagtgg gtgcactgtc taaaggtcag   1680
ttgaaagagt tcctcgacgc taacctggcc ggctctggat ccggtgatga cgatgacaag   1740
gccatggaga ccgacgtcca catatacctg ccgttcacta ttatttagtg aaatgagata   1800
ttatgatatt ttctgaattg tgattaaaaa ggcaacttta tgcccatgca acagaaacta   1860
taaaaaatac agagaatgaa aagaaacaga tagatttttt agttctttag gcccgtagtc   1920
tgcaaatcct tttatgattt tctatcaaac aaaagaggaa aatagaccag ttgcaatcca   1980
aacgagagtc taatagaatg aggtcgaaaa gtaaatcgcg cgggtttgtt actgataaag   2040
caggcaagac ctaaaatgtg taaagggcaa agtgtatact ttggcgtcac cccttacata   2100
ttttaggtct ttttttattg tgcgtaacta acttgccatc ttcaaacagg agggctggaa   2160
gaagcagacc gctaacacag tacataaaaa aggagacatg aacgatgaac atcaaaaagt   2220
ttgcaaaaca agcaacagta ttaaccttta ctaccgcact gctggcagga ggcgcaactc   2280
aagcgtttgc gaaagaaacg aaccaaaagc catataagga aacatacggc atttcccata   2340
ttacacgcca tgatatgctg caaatccctg aacagcaaaa aaatgaaaaa tataaagttc   2400
ctgagttcga ttcgtccaca attaaaaata tctcttctgc aaaaggcctg gacgtttggg   2460
acagctggcc attacaaaac actgacggca ctgtcgcaaa ctatcacggc taccacatcg   2520
tctttgcatt agccggagat cctaaaaatg cggatgacac atcgatttac atgttctatc   2580
aaaaagtcgg cgaaacttct attgacagct ggaaaaacgc tggccgcgtc tttaaagaca   2640
gcgacaaatt cgatgcaaat gattctatcc taaaagacca aacacaagaa tggtcaggtt   2700
cagccacatt tacatctgac ggaaaaatcc gtttattcta cactgatttc tccggtaaac   2760
attacggcaa acaaacactg acaactgcac aagttaacgt atcagcatca gacagctctt   2820
tgaacatcaa cggtgtagag gattataaat caatctttga cggtgacgga aaaacgtatc   2880
aaaatgtaca gcagttcatc gatgaaggca actacagctc aggcgacaac catacgctga   2940
gagatcctca ctacgtagaa gataaaggcc acaaatactt agtatttgaa gcaaacactg   3000
gaactgaaga tggctaccaa ggcgaagaat ctttatttaa caaagcatac tatggcaaaa   3060
gcacatcatt cttccgtcaa gaaagtcaaa aacttctgca aagcgataaa aaacgcacgg   3120
ctgagttagc aaacggcgct ctcggtatga ttgagctaaa cgatgattac acactgaaaa   3180
aagtgatgaa accgctgatt gcatctaaca cagtaacaga tgaaattgaa cgcgcgaacg   3240
tctttaaaat gaacggcaaa tggtacctgt tcactgactc ccgcggatca aaaatgacga   3300
ttgacggcat tacgtctaac gatatttaca tgcttggtta tgtttctaat tctttaactg   3360
gcccatacaa gccgctgaac aaaactggcc ttgtgttaaa aatggatctt gatcctaacg   3420
atgtaacctt tacttactca cacttcgctg tacctcaagc gaaaggaaac aatgtcgtga   3480
ttacaagcta tatgacaaac agaggattct acgcagacaa acaatcaacg tttgcgccta   3540
gcttcctgct gaacatcaaa ggcaagaaaa catctgttgt caaagacagc atccttgaac   3600
aaggacaatt aacagttaac aaataaaaac gcaaaagaaa atgccgatat cctattggca   3660
ttgacggtct ccagtaccac catcatcatc atcattaagt cagcggccgc actcgagcac   3720
```

-continued

```
caccaccacc accactgaga tccggctgct aacaaagccc gaaaggaagc tgagttggct   3780
gctgccaccg ctgagcaata actagcataa ccccttgggg cctctaaacg ggtcttgagg   3840
ggttttttgc tgaaaggagg aactatatcc ggattggcga atgggacgcg ccctgtagcg   3900
gcgcattaag cgcggcgggt gtggtggtta cgcgcagcgt gaccgctaca cttgccagcg   3960
ccctagcgcc cgctcctttc gctttcttcc cttcctttct cgccacgttc gccggctttc   4020
cccgtcaagc tctaaatcgg gggctccctt tagggttccg atttagtgct ttacggcacc   4080
tcgaccccaa aaaacttgat tagggtgatg gttcacgtag tgggccatcg ccctgataga   4140
cggtttttcg ccctttgacg ttggagtcca cgttctttaa tagtggactc ttgttccaaa   4200
ctggaacaac actcaaccct atctcggtct attcttttga tttataaggg attttgccga   4260
tttcggccta ttggttaaaa aatgagctga tttaacaaaa atttaacgcg aattttaaca   4320
aaatattaac gtttacaatt tcaggtggca cttttcgggg aaatgtgcgc ggaaccccta   4380
tttgtttatt tttctaaata cattcaaata tgtatccgct catgaattaa ttcttagaaa   4440
aactcatcga gcatcaaatg aaactgcaat ttattcatat caggattatc aataccatat   4500
ttttgaaaaa gccgtttctg taatgaagga gaaaactcac cgaggcagtt ccataggatg   4560
gcaagatcct ggtatcggtc tgcgattccg actcgtccaa catcaataca acctattaat   4620
ttcccctcgt caaaaataag gttatcaagt gagaaatcac catgagtgac gactgaatcc   4680
ggtgagaatg gcaaaagttt atgcatttct ttccagactt gttcaacagg ccagccatta   4740
cgctcgtcat caaaatcact cgcatcaacc aaaccgttat tcattcgtga ttgcgcctga   4800
gcgagacgaa atacgcgatc gctgttaaaa ggacaattac aaacaggaat cgaatgcaac   4860
cggcgcagga acactgccag cgcatcaaca atattttcac ctgaatcagg atattcttct   4920
aatacctgga atgctgtttt cccggggatc gcagtggtga gtaaccatgc atcatcagga   4980
gtacggataa aatgcttgat ggtcggaaga ggcataaatt ccgtcagcca gtttagtctg   5040
accatctcat ctgtaacatc attggcaacg ctacctttgc catgtttcag aaacaactct   5100
ggcgcatcgg gcttcccata caatcgatag attgtcgcac ctgattgccc gacattatcg   5160
cgagcccatt tatacccata taaatcagca tccatgttgg aatttaatcg cggcctagag   5220
caagacgttt cccgttgaat atggctcata acaccccttg tattactgtt tatgtaagca   5280
gacagtttta ttgttcatga ccaaaatccc ttaacgtgag ttttcgttcc actgagcgtc   5340
agaccccgta gaaaagatca aaggatcttc ttgagatcct ttttttctgc gcgtaatctg   5400
ctgcttgcaa acaaaaaaac caccgctacc agcggtggtt tgtttgccgg atcaagagct   5460
accaactctt tttccgaagg taactggctt cagcagagcg cagataccaa atactgtcct   5520
tctagtgtag ccgtagttag gccaccactt caagaactct gtagcaccgc ctacatacct   5580
cgctctgcta atcctgttac cagtggctgc tgccagtggc gataagtcgt gtcttaccgg   5640
gttggactca agacgatagt taccggataa ggcgcagcgg tcgggctgaa cggggggttc   5700
gtgcacacag cccagcttgg agcgaacgac ctacaccgaa ctgagatacc tacagcgtga   5760
gctatgagaa agcgccacgc ttcccgaagg gagaaaggcg gacaggtatc cggtaagcgg   5820
cagggtcgga acaggagagc gcacgaggga gcttccaggg ggaaacgcct ggtatcttta   5880
tagtcctgtc gggtttcgcc acctctgact tgagcgtcga tttttgtgat gctcgtcagg   5940
ggggcggagc ctatggaaaa acgccagcaa cgcggccttt ttacggttcc tggccttttg   6000
ctggcctttt gctcacatgt tctttcctgc gttatcccct gattctgtgg ataaccgtat   6060
taccgccttt gagtgagctg ataccgctcg ccgcagccga acgaccgagc gcagcgagtc   6120
```

-continued

```
agtgagcgag gaagcggaag agcgcctgat gcggtatttt ctccttacgc atctgtgcgg   6180

tatttcacac cgcatatatg gtgcactctc agtacaatct gctctgatgc cgcatagtta   6240

agccagtata cactccgcta tcgctacgtg actgggtcat ggctgcgccc cgacacccgc   6300

caacacccgc tgacgcgccc tgacgggctt gtctgctccc ggcatccgct tacagacaag   6360

ctgtgaccgt ctccgggagc tgcatgtgtc agaggttttc accgtcatca ccgaaacgcg   6420

cgaggcagct gcggtaaagc tcatcagcgt ggtcgtgaag cgattcacag atgtctgcct   6480

gttcatccgc gtccagctcg ttgagtttct ccagaagcgt taatgtctgg cttctgataa   6540

agcgggccat gttaagggcg gtttttttcct gtttggtcac tgatgcctcc gtgtaagggg   6600

gatttctgtt catgggggta atgataccga tgaaacgaga gaggatgctc acgatacggg   6660

ttactgatga tgaacatgcc cggttactgg aacgttgtga gggtaaacaa ctggcggtat   6720

ggatgcggcg ggaccagaga aaaatcactc agggtcaatg ccagcgcttc gttaatacag   6780

atgtaggtgt tccacagggt agccagcagc atcctgcgat gcagatccgg aacataatgg   6840

tgcagggcgc tgacttccgc gtttccagac tttacgaaac acggaaaccg aagaccattc   6900

atgttgttgc tcaggtcgca gacgttttgc agcagcagtc gcttcacgtt cgctcgcgta   6960

tcggtgattc attctgctaa ccagtaaggc aaccccgcca gcctagccgg gtcctcaacg   7020

acaggagcac gatcatgcgc acccgtgaaa c                                  7051
```

```
<210> SEQ ID NO 21
<211> LENGTH: 6695
<212> TYPE: DNA
<213> ORGANISM: Artificial Sequence
<220> FEATURE:
<223> OTHER INFORMATION: pVTSD9 Vector

<400> SEQUENCE: 21
```

```
gcgcgaggca gcagatcaat tcgcgcgcga aggcgaagcg gcatgcataa tgtgcctgtc     60

aaatggacga agcagggatt ctgcaaaccc tatgctactc cgtcaagccg tcaattgtct    120

gattcgttac caattatgac aacttgacgg ctacatcatt cactttttct tcacaaccgg    180

cacggaactc gctcgggctg gccccggtgc atttttttaaa tacccgcgag aaatagagtt    240

gatcgtcaaa accaacattg cgaccgacgg tggcgatagg catccgggtg gtgctcaaaa    300

gcagcttcgc ctggctgata cgttggtcct cgcgccagct taagacgcta atccctaact    360

gctggcggaa aagatgtgac agacgcgacg gcgacaagca aacatgctgt gcgacgctgg    420

cgatatcaaa attgctgtct gccaggtgat cgctgatgta ctgacaagcc tcgcgtaccc    480

gattatccat cggtggatgg agcgactcgt taatcgcttc catgcgccgc agtaacaatt    540

gctcaagcag atttatcgcc agcagctccg aatagcgccc ttccccttgc ccggcgttaa    600

tgatttgccc aaacaggtcg ctgaaatgcg gctggtgcgc ttcatccggg cgaaagaacc    660

ccgtattggc aaatattgac ggccagttaa gccattcatg ccagtaggcg cgcggacgaa    720

agtaaaccca ctggtgatac cattcgcgag cctccggatg acgaccgtag tgatgaatct    780

ctcctggcgg gaacagcaaa atatcacccg gtcggcaaac aaattctcgt ccctgatttt    840

tcaccacccc ctgaccgcga atggtgagat tgagaatata acctttcatt cccagcggtc    900

ggtcgataaa aaaatcgaga taaccgttgg cctcaatcgg cgttaaaccc gccaccagat    960

gggcattaaa cgagtatccc ggcagcaggg gatcattttg cgcttcagcc atacttttca   1020

tactcccgcc attcagagaa gaaaccaatt gtccatattg catcagacat tgccgtcact   1080
```

-continued

```
gcgtctttta ctggctcttc tcgctaacca aaccggtaac cccgcttatt aaaagcattc   1140
tgtaacaaag cgggaccaaa gccatgacaa aaacgcgtaa caaaagtgtc tataatcacg   1200
gcagaaaagt ccacattgat tatttgcacg gcgtcacact ttgctatgcc atagcatttt   1260
tatccataag attagcggat cctacctgac gctttttatc gcaactctct actgtttctc   1320
catacccgtt tttttgggct agaaataatt ttgtttaact ttaagaagga gatatacata   1380
cccatccatg gagaccgacg tccacatata cctgccgttc actattattt agtgaaatga   1440
gatattatga tattttctga attgtgatta aaaaggcaac tttatgccca tgcaacagaa   1500
actataaaaa atacagagaa tgaaaagaaa cagatagatt ttttagttct ttaggcccgt   1560
agtctgcaaa tccttttatg attttctatc aaacaaaaga ggaaaataga ccagttgcaa   1620
tccaaacgag agtctaatag aatgaggtcg aaaagtaaat cgcgcgggtt tgttactgat   1680
aaagcaggca agacctaaaa tgtgtaaagg gcaaagtgta tactttggcg tcacccctta   1740
catattttag gtcttttttt attgtgcgta actaacttgc catcttcaaa caggagggct   1800
ggaagaagca gaccgctaac acagtacata aaaaaggaga catgaacgat gaacatcaaa   1860
aagtttgcaa aacaagcaac agtattaacc tttactaccg cactgctggc aggaggcgca   1920
actcaagcgt ttgcgaaaga aacgaaccaa aagccatata aggaaacata cggcatttcc   1980
catattacac gccatgatat gctgcaaatc cctgaacagc aaaaaaatga aaaatataaa   2040
gttcctgagt tcgattcgtc cacaattaaa aatatctctt ctgcaaaagg cctggacgtt   2100
tgggacagct ggccattaca aaacactgac ggcactgtcg caaactatca cggctaccac   2160
atcgtctttg cattagccgg agatcctaaa aatgcggatg acacatcgat ttacatgttc   2220
tatcaaaaag tcggcgaaac ttctattgac agctggaaaa acgctggccg cgtctttaaa   2280
gacagcgaca aattcgatgc aaatgattct atcctaaaag accaaacaca agaatggtca   2340
ggttcagcca catttacatc tgacggaaaa atccgtttat tctacactga tttctccggt   2400
aaacattacg gcaaacaaac actgacaact gcacaagtta acgtatcagc atcagacagc   2460
tctttgaaca tcaacggtgt agaggattat aaatcaatct ttgacggtga cggaaaaacg   2520
tatcaaaatg tacagcagtt catcgatgaa ggcaactaca gctcaggcga caaccatacg   2580
ctgagagatc ctcactacgt agaagataaa ggccacaaat acttagtatt tgaagcaaac   2640
actggaactg aagatggcta ccaaggcgaa gaatctttat ttaacaaagc atactatggc   2700
aaaagcacat cattcttccg tcaagaaagt caaaaacttc tgcaaagcga taaaaaacgc   2760
acggctgagt tagcaaacgg cgctctcggt atgattgagc taaacgatga ttacacactg   2820
aaaaaagtga tgaaaccgct gattgcatct aacacagtaa cagatgaaat tgaacgcgcg   2880
aacgtcttta aaatgaacgg caaatggtac ctgttcactg actcccgcgg atcaaaaatg   2940
acgattgacg gcattacgtc taacgatatt tacatgcttg gttatgtttc taattcttta   3000
actggcccat acaagccgct gaacaaaact ggccttgtgt taaaaatgga tcttgatcct   3060
aacgatgtaa cctttactta ctcacacttc gctgtacctc aagcgaaagg aaacaatgtc   3120
gtgattacaa gctatatgac aaacagagga ttctacgcag acaaacaatc aacgtttgcg   3180
cctagcttcc tgctgaacat caaaggcaag aaaacatctg ttgtcaaaga cagcatcctt   3240
gaacaaggac aattaacagt taacaaataa aaacgcaaaa gaaaatgccg atatcctatt   3300
ggcattgacg gtctccagta ccaccatcat catcatcatt aagtcagcgg ccgcactcga   3360
gcaccaccac caccaccact gagatccggc tgctaacaaa gcccgaaagg aagctgagtt   3420
ggctgctgcc accgctgagc aataactagc ataacccctt ggggcctcta aacgggtctt   3480
```

```
gaggggtttt ttgctgaaag gaggaactat atccggattg gcgaatggga cgcgccctgt   3540
agcggcgcat taagcgcggc gggtgtggtg gttacgcgca gcgtgaccgc tacacttgcc   3600
agcgccctag cgcccgctcc tttcgctttc ttcccttcct ttctcgccac gttcgccggc   3660
tttccccgtc aagctctaaa tcgggggctc cctttagggt tccgatttag tgctttacgg   3720
cacctcgacc ccaaaaaact tgattagggt gatggttcac gtagtgggcc atcgccctga   3780
tagacggttt ttcgcccttt gacgttggag tccacgttct ttaatagtgg actcttgttc   3840
caaactggaa caacactcaa ccctatctcg gtctattctt ttgatttata agggattttg   3900
ccgatttcgg cctattggtt aaaaaatgag ctgatttaac aaaaatttaa cgcgaatttt   3960
aacaaaatat taacgtttac aatttcaggt ggcacttttc ggggaaatgt gcgcggaacc   4020
cctatttgtt tatttttcta aatacattca aatatgtatc cgctcatgaa ttaattctta   4080
gaaaaactca tcgagcatca aatgaaactg caatttattc atatcaggat tatcaatacc   4140
atatttttga aaaagccgtt tctgtaatga aggagaaaac tcaccgaggc agttccatag   4200
gatggcaaga tcctggtatc ggtctgcgat tccgactcgt ccaacatcaa tacaacctat   4260
taatttcccc tcgtcaaaaa taaggttatc aagtgagaaa tcaccatgag tgacgactga   4320
atccggtgag aatggcaaaa gtttatgcat ttctttccag acttgttcaa caggccagcc   4380
attacgctcg tcatcaaaat cactcgcatc aaccaaaccg ttattcattc gtgattgcgc   4440
ctgagcgaga cgaaatacgc gatcgctgtt aaaaggacaa ttacaaacag gaatcgaatg   4500
caaccggcgc aggaacactg ccagcgcatc aacaatattt tcacctgaat caggatattc   4560
ttctaatacc tggaatgctg ttttcccggg gatcgcagtg gtgagtaacc atgcatcatc   4620
aggagtacgg ataaaatgct tgatggtcgg aagaggcata aattccgtca gccagtttag   4680
tctgaccatc tcatctgtaa catcattggc aacgctacct ttgccatgtt tcagaaacaa   4740
ctctggcgca tcgggcttcc catacaatcg atagattgtc gcacctgatt gcccgacatt   4800
atcgcgagcc catttatacc catataaatc agcatccatg ttggaattta atcgcggcct   4860
agagcaagac gtttcccgtt gaatatggct cataacaccc cttgtattac tgtttatgta   4920
agcagacagt tttattgttc atgaccaaaa tcccttaacg tgagttttcg ttccactgag   4980
cgtcagaccc cgtagaaaag atcaaaggat cttcttgaga tccttttttt ctgcgcgtaa   5040
tctgctgctt gcaaacaaaa aaaccaccgc taccagcggt ggtttgtttg ccggatcaag   5100
agctaccaac tctttttccg aaggtaactg gcttcagcag agcgcagata ccaaatactg   5160
tccttctagt gtagccgtag ttaggccacc acttcaagaa ctctgtagca ccgcctacat   5220
acctcgctct gctaatcctg ttaccagtgg ctgctgccag tggcgataag tcgtgtctta   5280
ccgggttgga ctcaagacga tagttaccgg ataaggcgca gcggtcgggc tgaacggggg   5340
gttcgtgcac acagcccagc ttggagcgaa cgacctacac cgaactgaga tacctacagc   5400
gtgagctatg agaaagcgcc acgcttcccg aagggagaaa ggcggacagg tatccggtaa   5460
gcggcagggt cggaacagga gagcgcacga gggagcttcc agggggaaac gcctggtatc   5520
tttatagtcc tgtcgggttt cgccacctct gacttgagcg tcgatttttg tgatgctcgt   5580
caggggggcg gagcctatgg aaaaacgcca gcaacgcggc ctttttacgg ttcctggcct   5640
tttgctggcc ttttgctcac atgttctttc ctgcgttatc ccctgattct gtggataacc   5700
gtattaccgc ctttgagtga gctgataccg ctcgccgcag ccgaacgacc gagcgcagcg   5760
agtcagtgag cgaggaagcg gaagagcgcc tgatgcggta ttttctcctt acgcatctgt   5820
```

-continued

```
gcggtatttc acaccgcata tatggtgcac tctcagtaca atctgctctg atgccgcata   5880

gttaagccag tatacactcc gctatcgcta cgtgactggg tcatggctgc gccccgacac   5940

ccgccaacac ccgctgacgc gccctgacgg gcttgtctgc tcccggcatc cgcttacaga   6000

caagctgtga ccgtctccgg gagctgcatg tgtcagaggt tttcaccgtc atcaccgaaa   6060

cgcgcgaggc agctgcggta aagctcatca gcgtggtcgt gaagcgattc acagatgtct   6120

gcctgttcat ccgcgtccag ctcgttgagt ttctccagaa gcgttaatgt ctggcttctg   6180

ataaagcggg ccatgttaag ggcggttttt tcctgtttgg tcactgatgc ctccgtgtaa   6240

gggggatttc tgttcatggg ggtaatgata ccgatgaaac gagagaggat gctcacgata   6300

cgggttactg atgatgaaca tgcccggtta ctggaacgtt gtgagggtaa acaactggcg   6360

gtatggatgc ggcgggacca gagaaaaatc actcagggtc aatgccagcg cttcgttaat   6420

acagatgtag gtgttccaca gggtagccag cagcatcctg cgatgcagat ccggaacata   6480

atggtgcagg gcgctgactt ccgcgtttcc agactttacg aaacacggaa accgaagacc   6540

attcatgttg ttgctcaggt cgcagacgtt ttgcagcagc agtcgcttca cgttcgctcg   6600

cgtatcggtg attcattctg ctaaccagta aggcaacccc gccagcctag ccgggtcctc   6660

aacgacagga gcacgatcat gcgcacccgt gaaac                              6695
```

```
<210> SEQ ID NO 22
<211> LENGTH: 20
<212> TYPE: DNA
<213> ORGANISM: Artificial Sequence
<220> FEATURE:
<223> OTHER INFORMATION: RE BpiI - upstream
<220> FEATURE:
<221> NAME/KEY: unsure
<222> LOCATION: 7..20
<223> OTHER INFORMATION: /note="a or g or c or t"

<400> SEQUENCE: 22

gaagacnnct tctgnnnnnn                                                 20


<210> SEQ ID NO 23
<211> LENGTH: 20
<212> TYPE: DNA
<213> ORGANISM: Artificial Sequence
<220> FEATURE:
<223> OTHER INFORMATION: RE BpiI downstream
<220> FEATURE:
<221> NAME/KEY: unsure
<222> LOCATION: 1..14
<223> OTHER INFORMATION: /note="a or g or c or t"

<400> SEQUENCE: 23

nnnnnngtct tcnncagaag                                                 20


<210> SEQ ID NO 24
<211> LENGTH: 24
<212> TYPE: DNA
<213> ORGANISM: Artificial Sequence
<220> FEATURE:
<223> OTHER INFORMATION: RE BfuAI Upstream
<220> FEATURE:
<221> NAME/KEY: unsure
<222> LOCATION: 7..24
<223> OTHER INFORMATION: /note="a or g or c or t"

<400> SEQUENCE: 24

acctgcnnnn tggacgnnnn nnnn                                            24
```

<210> SEQ ID NO 25
<211> LENGTH: 24
<212> TYPE: DNA
<213> ORGANISM: Artificial Sequence
<220> FEATURE:
<223> OTHER INFORMATION: RE BfuAI downstream
<220> FEATURE:
<221> NAME/KEY: unsure
<222> LOCATION: 1..18
<223> OTHER INFORMATION: /note="a or g or c or t"

<400> SEQUENCE: 25
nnnnnnnngc aggtnnnncg tcca 24

<210> SEQ ID NO 26
<211> LENGTH: 19
<212> TYPE: DNA
<213> ORGANISM: Artificial Sequence
<220> FEATURE:
<223> OTHER INFORMATION: RE SapI upstream
<220> FEATURE:
<221> NAME/KEY: unsure
<222> LOCATION: 8..19
<223> OTHER INFORMATION: /note="a or g or c or t"

<400> SEQUENCE: 26
gctcttcncg agaagnnnn 19

<210> SEQ ID NO 27
<211> LENGTH: 19
<212> TYPE: DNA
<213> ORGANISM: Artificial Sequence
<220> FEATURE:
<223> OTHER INFORMATION: RE SapI downstream
<220> FEATURE:
<221> NAME/KEY: unsure
<222> LOCATION: 1..12
<223> OTHER INFORMATION: /note="a or g or c or t"

<400> SEQUENCE: 27
nnnngaagag cncttctcg 19

<210> SEQ ID NO 28
<211> LENGTH: 36
<212> TYPE: DNA
<213> ORGANISM: Artificial Sequence
<220> FEATURE:
<223> OTHER INFORMATION: RE BtgZl upstream
<220> FEATURE:
<221> NAME/KEY: unsure
<222> LOCATION: 7..36
<223> OTHER INFORMATION: /note="a or g or c or t"

<400> SEQUENCE: 28
gcgatgnnnn nnnnnncgct acnnnnnnnn nnnnnn 36

<210> SEQ ID NO 29
<211> LENGTH: 37
<212> TYPE: DNA
<213> ORGANISM: Artificial Sequence
<220> FEATURE:
<223> OTHER INFORMATION: RE BtgZl downstream
<220> FEATURE:
<221> NAME/KEY: unsure
<222> LOCATION: 1..31
<223> OTHER INFORMATION: /note="a or g or c or t"

<400> SEQUENCE: 29
nnnnnnnnnn nnnnncatcg cnnnnnnnnn ngtagcg 37

<210> SEQ ID NO 30
<211> LENGTH: 18
<212> TYPE: DNA
<213> ORGANISM: Artificial Sequence
<220> FEATURE:
<223> OTHER INFORMATION: RE Bsmbl upstream
<220> FEATURE:
<221> NAME/KEY: unsure
<222> LOCATION: 7..18
<223> OTHER INFORMATION: /note="a or g or c or t"

<400> SEQUENCE: 30
cgtctcngca gagnnnnn 18

<210> SEQ ID NO 31
<211> LENGTH: 18
<212> TYPE: DNA
<213> ORGANISM: Artificial Sequence
<220> FEATURE:
<223> OTHER INFORMATION: RE Bsmbl downstream
<220> FEATURE:
<221> NAME/KEY: unsure
<222> LOCATION: 1..12
<223> OTHER INFORMATION: /note="a or g or c or t"

<400> SEQUENCE: 31
nnnnngagac gnctctgc 18

<210> SEQ ID NO 32
<211> LENGTH: 30
<212> TYPE: DNA
<213> ORGANISM: Artificial Sequence
<220> FEATURE:
<223> OTHER INFORMATION: RE BseRl upstream
<220> FEATURE:
<221> NAME/KEY: unsure
<222> LOCATION: 7..30
<223> OTHER INFORMATION: /note="a or g or c or t"

<400> SEQUENCE: 32
gaggagnnnn nnnnnnctcc tcnnnnnnnn 30

<210> SEQ ID NO 33
<211> LENGTH: 30
<212> TYPE: DNA
<213> ORGANISM: Artificial Sequence
<220> FEATURE:
<223> OTHER INFORMATION: RE BseRl downstream
<220> FEATURE:
<221> NAME/KEY: unsure
<222> LOCATION: 1..24
<223> OTHER INFORMATION: /note="a or g or c or t"

<400> SEQUENCE: 33
nnnnnnnnct cctcnnnnnn nnnngaggag 30

<210> SEQ ID NO 34
<211> LENGTH: 17
<212> TYPE: DNA
<213> ORGANISM: Artificial Sequence
<220> FEATURE:
<223> OTHER INFORMATION: EAD 10 - primer a

<400> SEQUENCE: 34
tacgacattg cgtggag 17

<210> SEQ ID NO 35
<211> LENGTH: 35

<212> TYPE: DNA
<213> ORGANISM: Artificial Sequence
<220> FEATURE:
<223> OTHER INFORMATION: EAD 10 - primer b

<400> SEQUENCE: 35
ctgaatgtct ggccggtttc aaaagccata caggc 35

<210> SEQ ID NO 36
<211> LENGTH: 35
<212> TYPE: DNA
<213> ORGANISM: Artificial Sequence
<220> FEATURE:
<223> OTHER INFORMATION: EAD 10 - primer c

<400> SEQUENCE: 36
gcctgtatgg cttttgaaac cggccagaca ttcag 35

<210> SEQ ID NO 37
<211> LENGTH: 26
<212> TYPE: DNA
<213> ORGANISM: Artificial Sequence
<220> FEATURE:
<223> OTHER INFORMATION: EAD 10 - primer d

<400> SEQUENCE: 37
atacgaaata acgtgacgat tttcag 26

<210> SEQ ID NO 38
<211> LENGTH: 17
<212> TYPE: DNA
<213> ORGANISM: Artificial Sequence
<220> FEATURE:
<223> OTHER INFORMATION: EAD 16 - primer a

<400> SEQUENCE: 38
aaaagccccg cttatcc 17

<210> SEQ ID NO 39
<211> LENGTH: 36
<212> TYPE: DNA
<213> ORGANISM: Artificial Sequence
<220> FEATURE:
<223> OTHER INFORMATION: EAD 16 - primer b

<400> SEQUENCE: 39
cgctcgaaca ggatcgatac ctggccatcg tcctgg 36

<210> SEQ ID NO 40
<211> LENGTH: 36
<212> TYPE: DNA
<213> ORGANISM: Artificial Sequence
<220> FEATURE:
<223> OTHER INFORMATION: EAD 16 - primer c

<400> SEQUENCE: 40
ccaggacgat ggccaggtat cgatcctgtt cgagcg 36

<210> SEQ ID NO 41
<211> LENGTH: 16
<212> TYPE: DNA
<213> ORGANISM: Artificial Sequence -continued

```
<220> FEATURE:
<223> OTHER INFORMATION: EAD 16 - primer d

<400> SEQUENCE: 41

cgacccgccc ccgaac                                                       16
```

POLYNUCLEOTIDE SHUFFLING METHOD

SEQUENCE LISTING

The sequence listing provided in the file, entitled GHE0030PA_Sequence_Listing.txt, created Apr. 26, 2022 (107,000 bytes), is incorporated herein by reference in its entirety.

BACKGROUND OF THE INVENTION

A. Field of the Invention

Proteins are highly versatile biomolecules that perform a broad range of functions, ranging from natural catalysis (enzymes), epitope recognition (antibodies) to structural functions. The capacity of enzymes to perform very specific reactions at a high rate has made them increasingly useful for various fields, including technical use (paper and textile industry), food and feed industry (dairy, baking, brewing, juice production, starch processing), organic synthesis industry, cosmetics, medicine and biotechnology. As such, industrial enzymes have revolutionized our daily life. Antibodies bind specific epitopes and are developed as diagnostic tools and therapeutics. Structural proteins have an important function in the structure of cells or tissue. The best known example is collagen, which is abundantly present in our bones and skin.

Nature has configured proteins to perform their natural role, optimized by Darwinian evolution. However, there is mostly a great discrepancy between a protein's natural function and the applications envisioned by scientists and engineers. Therefore, natural proteins have to be engineered to introduce novel or desirable properties for diverse applications (Lutz, 2010). Robust and versatile techniques for protein engineering have thus a pivotal role in boosting the possibilities of proteins for the market.

B. Description of the Related Art

The field of protein engineering has undergone a dramatic technological metamorphosis in the last two decades. In fact, in vitro protein engineering mimics the natural protein evolutionary forces on a lab-scale. Vertical or adaptive evolution implies the accumulation of genetic mutations in protein-encoding sequences, giving rise to proteins with altered properties. This process can be performed in vitro by site-directed mutagenesis to modify selected amino acids to improve catalytic (e.g., reaction rate) or biophysical (e.g. stability) properties (rational design). However, site-directed mutagenesis makes only sense when the three-dimensional structure and/or the enzyme mechanism is known and this information is often not available. With the development of techniques for random mutagenesis for directed evolution, this requirement was bypassed. Interestingly, random mutagenesis proved to be complementary to site-directed mutagenesis as often mutants in unexpected amino acids at more distant sites from the catalytic amino acids were selected.

Another principal mechanism by which proteins evolve new functions is driven by the exchange of genetic fragments (shuffling/horizontal transfer) (Lutz and Benkovic, 2000). As such, radically changed proteins with novel functions are created. This evolutionary force can only be mimicked to a limited extent with in vitro protein engineering. Domain swapping by restriction/ligation allows to recombine protein-encoding fragments from different origins using traditional molecular cloning techniques in a rational way. A requirement is the absence of recognition sites of the restriction sites that are used in this cloning process. This requirement becomes particularly cumbersome when multiple fragments from different sources are randomly assembled and many different restriction enzymes are needed. DNA shuffling is a method that allows random shuffling of parental sequences but is only applicable for closely related genes (>70% sequence identity, family shuffling). However, unlimited shuffling of fragments of non-related genes with low sequence identity has the potential to design novel protein functions in the most disruptive way. Technological difficulties have hampered progress in this field. Traditional recombination is not possible due to the absence of homology between the gene fragments. Two methods (SHIPREC and ITCHY) have been reported to create hybrid proteins from distantly related sequences (Ostermeier et al., 1999; Sieber et al., 2001; Patrick and Gerth, 2014). However, both methods are limited to hybrids composed of two fragments derived of two parental genes. SCRATCHY, a more elaborated methodology based on ITCHY, and SCOPE allow the recombination of multiple fragments, but those fragments can still only be derived from two parental genes (Kawarasaki et al., 2003; O'Maille et al., 2002). Golden Gate shuffling is a method that allows to shuffle fragments from parental genes both in a rational and random way. The junctions between fragments of different parental genes are four conserved nucleotides present in all parental genes at each junction. In order to identify potential junction sites, a sufficiently high homology among these genes is required. Golden Gate shuffling relies on a unique feature of type IIs restriction enzymes, i.e., the cleavage outside the recognition site. This allows removal of the recognition site when it was located at the terminus of a fragment. This peculiarity allows simultaneous restriction/ligation in a one tube, one step reaction for assembly of multiple gene fragments in scar-less assemblies (Engler et al., 2009). Unlimited, large scale shuffling of a high number of non-related gene fragments from many different sources to create novel enzymes remained a void in the field of protein engineering. It is expected that random shuffling of non-related fragments will—similar to random mutagenesis—generally yield many unexpected novel, improved chimeric proteins that combine fragments that could not be rationally envisioned beforehand.

The present invention provides an efficient method for preparing vectors, referred to as Tile vectors, which are particularly suited as repository and/or donor vectors of polynucleotides encoding protein units for use in methods for generating product nucleotides wherein said product nucleotides comprise a combination of two or more of said polynucleotides encoding a protein unit. Preferably, said polynucleotides encoding a protein unit are combined within said product nucleotide such that their sequences are integrated within a single reading frame.

SUMMARY OF THE INVENTION

It is a first object of the present invention to provide a method for preparing a Tile vector, being a vector, which comprises a selectable marker and a coding polynucleotide, wherein said coding polynucleotide is immediately preceded and followed by a type IIs recognition sequence, wherein said preceding and following recognition sequences are recognized by a same type IIs restriction enzyme, but have an opposite orientation. More particularly, the position and orientation of said preceding and following type IIs recognition sequences provides for the cleavage of said Tile vector by a corresponding type IIs restriction enzyme resulting in the release of said coding polynucleotide sequence having at its respective ends overhang sequences with a known orientation and length, while lacking said preceding and following type IIs recognition sequences.

In a second object the present invention provides a method for using such Tile vectors obtained as previously described for joining two or more coding polynucleotides to form a product polynucleotide. Typically, said product polynucleotide is integrated in a vector. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The present invention can be further summarized in following statements.

1. A method for preparing a Tile vector (24) comprising a selectable marker (6) and a coding polynucleotide sequence (10) immediately preceded and followed by a type IIs recognition sequence (12), wherein said preceding and following recognition sequences are recognized by a same type IIs restriction enzyme, but have an opposite orientation,
   wherein said Tile vector (24) can be cleaved using a type IIs restriction enzyme recognizing said preceding and following recognition sites resulting in the release of said coding polynucleotide sequence (10) having at its respective ends known overhang sequences, said released coding polynucleotide sequence lacking said preceding and following type IIs recognition sequences;
   said method comprising following steps:
   a) providing an initial coding polynucleotide (8) and extending the respective ends of said polynucleotide with a first (16) and second (17) terminal sequence wherein each of said terminal sequences comprises following elements:
      i. a coding extension sequence (11) (3×n), which is added adjacent to the respective ends of and in frame with the open reading frame of said initial coding polynucleotides;
      ii. a first type IIs recognition sequence (12) adjacent to said coding extension sequence wherein said first recognition sequence is oriented such that a type IIs restriction enzyme recognizing said first recognition site can cleave within said coding extension sequence (11) generating an overhang and wherein said first type IIs recognition sequences (12) of the first and second terminal sequences are recognized by a same type IIs enzyme, but have an opposite orientation;
      iii. a spacer sequence (13) adjacent to or within said first type IIs recognition sequence;
      iv. a second type IIs recognition sequence (14) adjacent to said spacer sequence wherein said second recognition sequence is oriented such that a type IIs restriction enzyme recognizing said second recognition sequence can cleave said spacer sequence to generate a spacer overhang and wherein said second type IIs recognition sequence is not recognized by a type IIs enzyme recognizing said first type IIs recognition sequence;
      v. a tail sequence (15) of sufficient length in order to allow binding of a type IIs restriction enzyme to said second recognition sequence;
   b) providing a receiving vector (1) comprising a first nucleotide sequence comprising a selectable marker (6) positioned between a first (3) and a second (4) type IIs recognition sequence, such that said vector can be cleaved using type IIs recognition enzymes recognizing said first (3) and second (4) type IIs recognition sequences to form:
      a stuffer sequence (2) comprising said first (3) and second (4) type IIs recognition sequences; and
      a selectable vector fragment (7) comprising said selectable marker (6) but lacking said first (3) and second (4) type IIs recognition sequences and having non-complementary terminal overhangs, wherein one overhang is complementary to the spacer overhang obtained after cleaving said first terminal sequence (16) using a type IIs recognition enzyme recognizing said second type IIs recognition sequence (14) of said first terminal sequence (16), while the other overhang sequence is complementary to the spacer overhang obtained by cleaving said second terminal sequence (17) using a type IIs restriction enzyme recognizing said second type IIs recognition sequences (14) of said second terminal sequence;
   c) incubating a mixture, wherein the mixture comprises:
      i. an extended initial coding polynucleotide of step (a);
      ii. a receiving vector of step (b);
      iii. type IIs restriction enzymes recognizing said second type IIs recognition sequences (14) of the terminal sequences of said extended initial coding polynucleotide;
      iv. type IIs restriction enzymes recognizing said first (3) and second (4) type IIs recognition sequence of the receiving vector;
      v. a DNA ligase.
2. The method according to statement 1 wherein said stuffer fragment (2) of the receiving vector comprises a counter-selectable marker (5).
3. The method according to statements 1 or 2 wherein said second type IIs recognition sequences (14) of the first (16) and second (17) terminal sequence of the extended polynucleotide are recognized by a same type IIs enzyme.
4. The method according to statement 3 wherein said first (3) and second (4) type IIs recognition sequence of the receiving vector are recognized by a same type IIs enzyme, but have an opposite orientation.
5. The method according to statement 4 wherein said first (3) and second (4) type IIs recognition sequence of the receiving vector are recognized by the same type IIs enzyme as the second type IIs recognition sequence (14) of the first (16) and second (17) terminal sequences of said extended initial coding polynucleotides.
6. The method according to statement 5 wherein said receiving vector (1) comprises two multiple cloning sites, a first multiple cloning site comprising a succession of multiple different type IIs recognition sequences and a second multiple cloning site comprising oppositely oriented type IIs recognition sequences recognized by the same type IIs enzymes as those in the first multiple cloning site, wherein said multiple cloning sites comprise said first (3) and second (4) type IIs recognition sequences of the receiving vector (1), which are recognized by a same type IIs enzyme as the second type IIs recognition sequences (14) of the first (16) and second (17) terminal sequences of said extended initial coding polynucleotide.

7. The method according to any of the statements 1 to 6 wherein said initial coding polynucleotide (8) extended with said terminal sequences (16, 17) is prepared using a DNA synthesis method.
8. The method according to any of the statements 1 to 6 wherein said initial coding polynucleotide (8) is extended with said terminal sequences (16, 17) using a polymerase chain reaction (PCR), wherein said PCR involves the use of tailed forward and reverse primers annealing on the respective ends of said initial coding polynucleotide, wherein said tail of the forward primer adds the first terminal sequence (16) and the tail of the reverse primer adds the second terminal sequence (17).
9. The method according to statement 8 wherein said PCR is an error prone PCR thus generating a multitude of vectors, which vary from one another in that they comprise random mutants of said initial coding polynucleotide. Alternatively, said PCR of statement 8 involves site directed mutagenesis PCR allowing to introduce predefined mutations within the initial coding sequence.
10. The method according to any of the statements 1 to 9 wherein said method comprises an additional step of introducing a directed mutation in the sequence of the initial coding polynucleotide comprised in said Tile vector, said additional step comprising the use of the Kunkel method, PCR site-directed mutagenesis with mismatch primers or a whole plasmid mutagenesis method (e.g. Quickchange method).
11. A Tile vector (24) comprising a selectable marker (6) and a coding polynucleotide sequence (10) immediately preceded and followed by a first type IIs recognition sequence (12), wherein said preceding and following type IIs recognition sequences (12) are recognized by a same type IIs restriction enzyme but have an opposite orientation; said Tile vector (24) characterized in that the coding polynucleotide sequence (10) comprises an initial polynucleotide sequence (8) immediately preceded and followed by two coding extension sequences (11) (3×n) being in frame with the open reading frame of the initial coding sequence (8).
12. A polynucleotide sequence comprising an initial coding polynucleotide sequence (8) and a first and second terminal sequence (16, 17), wherein each of said first and second terminal sequence (16, 17) comprises the following elements:
    i. a coding extension sequence (11) (3×n), which immediately precedes and follows the initial coding polynucleotide sequence (8) and which is in frame with the open reading frame of said initial coding polynucleotide sequence (8);
    ii. a first type IIs recognition sequence (12) adjacent to said coding extension sequence (11) (3×n) wherein said first type IIs recognition sequence (12) is oriented such that a type IIs restriction enzyme recognizing said first type IIs recognition sequence can cleave within said coding extension sequence (11) (3×n) generating an overhang and wherein said first type IIs recognition sequences of the first and second terminal sequences (12) are recognized by a same type IIs enzyme, but have an opposite orientation;
    iii. a spacer sequence (13) adjacent to or within said first type IIs recognition sequence (12);
    iv. a second type IIs recognition sequence (14) adjacent to said spacer sequence (13) wherein said second type IIs recognition sequence (14) is oriented such that a type IIs restriction enzyme recognizing said second type IIs recognition sequence (14) can cleave said spacer sequence (13) to generate a spacer overhang and wherein said second type IIs recognition sequences (14) of the first and second terminal sequences are not recognized by a type IIs enzyme recognizing said first type IIs recognition sequences (12);
    v. a tail sequence (15) of sufficient length in order to allow binding of a type IIs restriction enzyme to said second recognition sequence (14).
13. A method of joining two or more coding polynucleotides to form a product polynucleotide being integrated in a vector, the method comprising incubating a mixture, which comprises:
    i. two or more Tile vectors, preferably said Tile vectors are obtained according to the method of any of the statements 1 to 10, each comprising a coding polynucleotide sequence (10) that comprises two coding extension sequences (11) (3×n), wherein said coding polynucleotide sequence (10) is immediately preceded and followed by said type IIs recognition sequences (12), wherein said preceding and following recognition sequences (12) of said vectors are recognized by a same type IIs restriction enzyme;
    ii. a type IIs restriction enzyme that recognizes said preceding and following types IIs recognition sequences (12) within said Tile vectors and cleaves from each of said vectors a coding polynucleotide sequence (10), wherein at least one overhang of each released coding polynucleotide is complementary to at least one overhang of one other released coding polynucleotide;
    iii. a destination vector (18) comprising a first nucleotide sequence comprising a selectable marker (23) positioned between two first type IIs recognition sequences (21), wherein said first type IIs recognition sequences (21) are recognized by a same type IIs restriction enzyme but have an opposite orientation, such that said vector can be cleaved using a type IIs restriction enzyme recognizing said first type IIs recognition sequences to form:
        a stuffer sequence (20) comprising said first type IIs recognition sequences (21); preferably said stiffer sequence further comprises a counter-selectable marker (5); and
        a selectable vector fragment (19) comprising said selectable marker (23) but lacking said first type IIs recognition sequences (21) and having non-complementary terminal overhangs, wherein one overhang is complementary to at least one overhang of any of said released coding polynucleotides, while the other overhang is complementary to at least one other overhang of any of said released coding polynucleotides;

iv. a type IIs restriction enzyme recognizing said first type IIs recognition sequences (21) of said destination vector;

v. a DNA ligase.

14. The method according to statement 13 wherein said coding polynucleotides are combined within said product polynucleotide in a single reading frame.

15. The method according to statements 13 or 14 wherein said first type IIs recognition sequences (21) of the destination vector are recognized by a same type IIs restriction enzyme recognizing said preceding and following recognition sequences (12) of said Tile vectors.

16. The method according to statements 13 to 15 wherein said tile vectors are designed to release coding nucleotides comprising overhang sequences inducing the formation of a product nucleotide comprising a predefined number of linked coding polynucleotides and wherein the overhang sequences of the released coding polynucleotides predetermine the position of said coding polynucleotide within the order of the coding polynucleotides in the product nucleotide.

17. The method according to statement 16 wherein said Tile vectors provide two or more released coding polynucleotides differing in nucleotide sequence but sharing the same overhang sequences wherein said method results in the formation of different product nucleotides varying in the nucleotide sequence at the position in the product nucleotide as defined by said shared overhang sequences of said differing released coding polynucleotides.

18. The method according to statement 17 wherein said released coding polynucleotides differing in nucleotide sequence but sharing the same overhang sequences comprise different variants or mutants of a polynucleotide encoding a given protein unit.

19. The method according to statement 17 wherein said released coding polynucleotides differing in nucleotide sequence but sharing the same overhang sequences comprise different polynucleotides encoding different protein units.

20. A destination vector (18) comprising a selectable marker (23), two first type IIs recognition sequences (21) and a counter-selectable marker, characterized in that the selectable marker (23) is positioned between two (3×n) sequences ($P_1$ and $P_{n+1}$) each of said (3×n) sequences followed by a first type IIs recognition sequence (21);

the two first type IIs recognition sequences (21) are recognized by a same type IIs restriction enzyme recognizing said two first type IIs recognition sequences (21).

21. A receiving vector (1) comprising a first nucleotide sequence comprising a selectable marker (6) positioned between two multiple cloning sites, a first multiple cloning site comprising a succession of multiple different type IIs recognition sequences and a second multiple cloning site comprising oppositely oriented type IIs recognition sequences recognized by the same type IIs enzymes as those in the first multiple cloning site, wherein said multiple cloning sites comprise first (3) and second (4) type IIs recognition sequences; such that said vector can be cleaved using type IIs recognition enzymes recognizing said first (3) and second (4) type IIs recognition sequences to form:

a stuffer sequence (2) comprising said first (3) and second (4) type IIs recognition sequences; and a selectable vector fragment (7) comprising said selectable marker (6) but lacking said first and second type IIs recognition sequences and having non-complementary terminal overhangs.

DETAILED DESCRIPTION

List of Figures

FIG. 1: VersaTile shuffling based on type IIs restriction enzymes. A. Non-palindromic type IIs recognitions sites (▲) are removed from the ends of the tiles creating a nucleotide overhang (coding extension sequence). When these fragments are ligated in the respective destination vector they cannot be redigested as the type IIs recognition site is removed, hereby allowing for a simultaneous restriction and ligation reaction. Proper design of the type IIs restriction sites and selection of the nucleotide overhangs results in a stable dead-end product, the desired construct. B. In VersaTile shuffling, the created overhang is chosen as such that it is embedded in at least 3 nucleotides coding for 1 to n amino acids, which link adjacent tiles in an oriented manner. The carefully selected nucleotide linkers function as coding extension sequences (square, diamond, sphere, polygon), defining the final order of Tile assembly.

FIG. 2: Splicing by overlap extension. A Overview SOE PCR: in the first PCR two fragments with complementary ends comprising the mutated internal BsaI recognition sequence are generated. The mutation is ideally a silent mutation in the coding sequence. In the second PCR these fragments will hybridize and with addition of the forward (a) and reverse (d) primer the original sequence lacking the internal recognition site is regenerated. B. Scheme of the temperature program used for the second PCR (Touch-down PCR). The decreasing annealing temperature allows to find the optimum temperature for hybridization of the overlaps of the two generated fragments. C. Table of the used SOE primers for both EAD10 and EAD16 (The BsaI recognition sequence is underlined and the point mutation indicated in bold).

FIG. 3: pVTSE receiving vector backbone and linearization with iPCR. Four different pVTSEs were generated through the insertion of four different insert cassettes, each with the respective coding extension sequences ($P_n$) and flanking BsaI recognition sites: pVTSE1: P1, P2; pVTSE2: P2, P3: pVTSE3: P3, P4; pVTSE4: P4, P5. The pVTSEs are linearized through iPCR in such a manner that the ends of the linearized vector consist of the coding extension sequences. This is done by using primers complementary to the respective coding extension sequences and the adjacent BsaI recognition sites as depicted in the figure. The tables below show the different coding extension sequences, non-palindromic BsaI recognition sites and their corresponding nucleotide and amino acid sequences.

Figure 4:
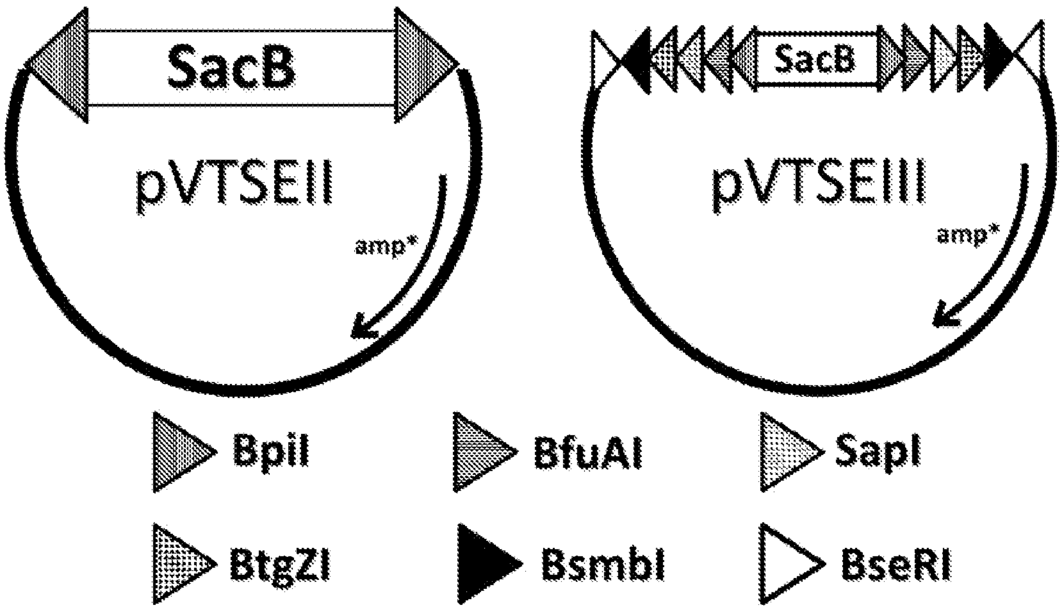

FIG. 4: Schematic representation of receiving vectors pVTSEII and pVTSEIII.

Figure 5:
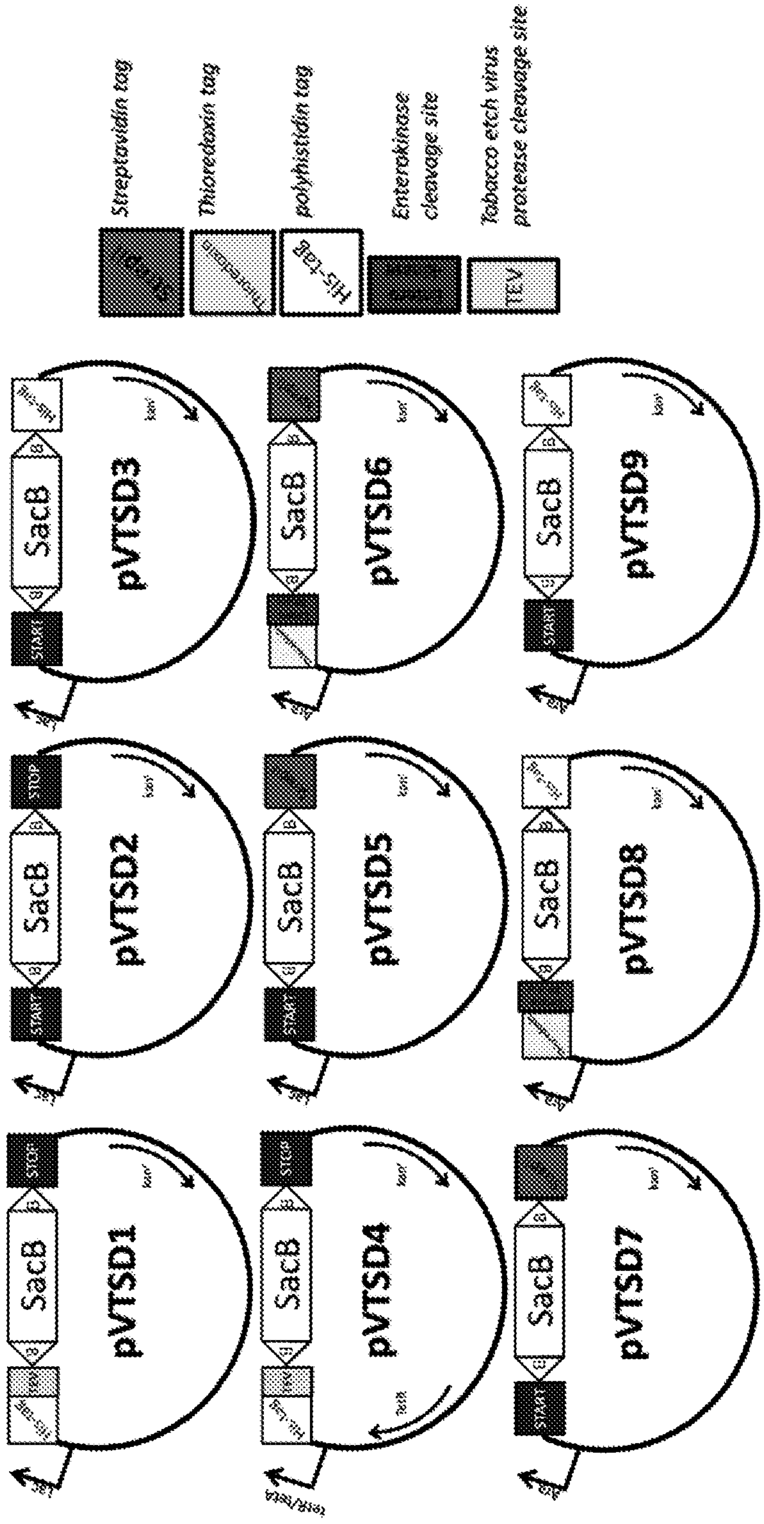

FIG. 5: Schematic overview of the different destination vectors compatible with VTS.

Figure 6:
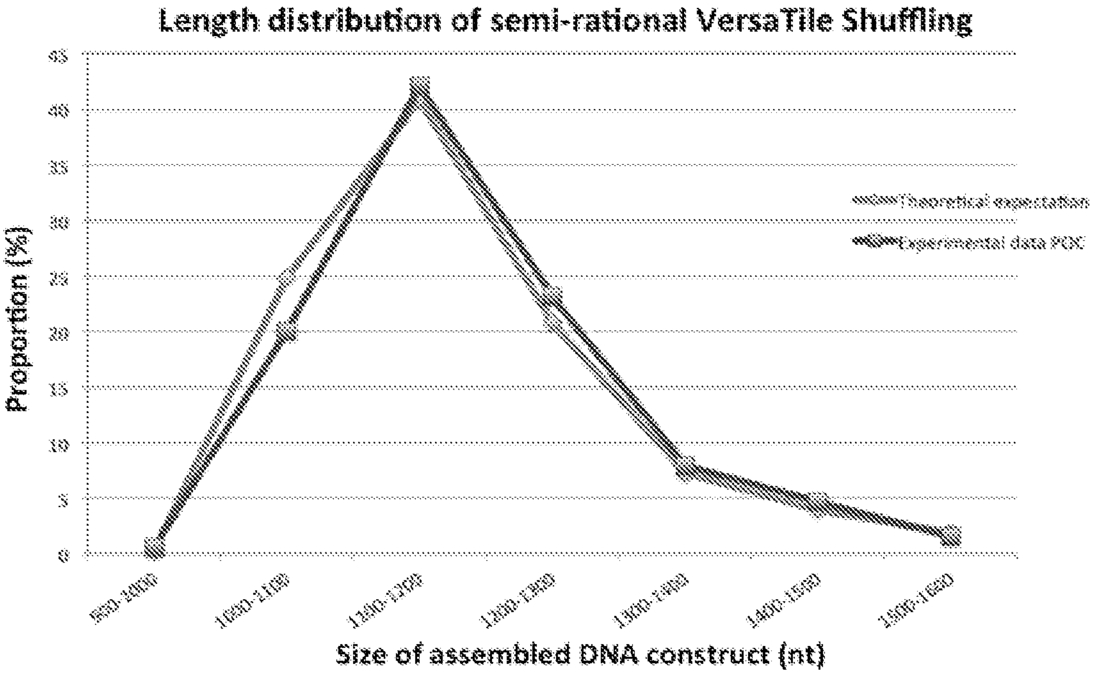

FIG. 6. Length distribution of semi-rational VersaTile shuffling. The theoretical expectation, calculated using a R script, is represented by the light grey curve. The experimental data of the proof-of-concept are represented in the dark grey curve. The curves are non-contentious.

Figure 7:
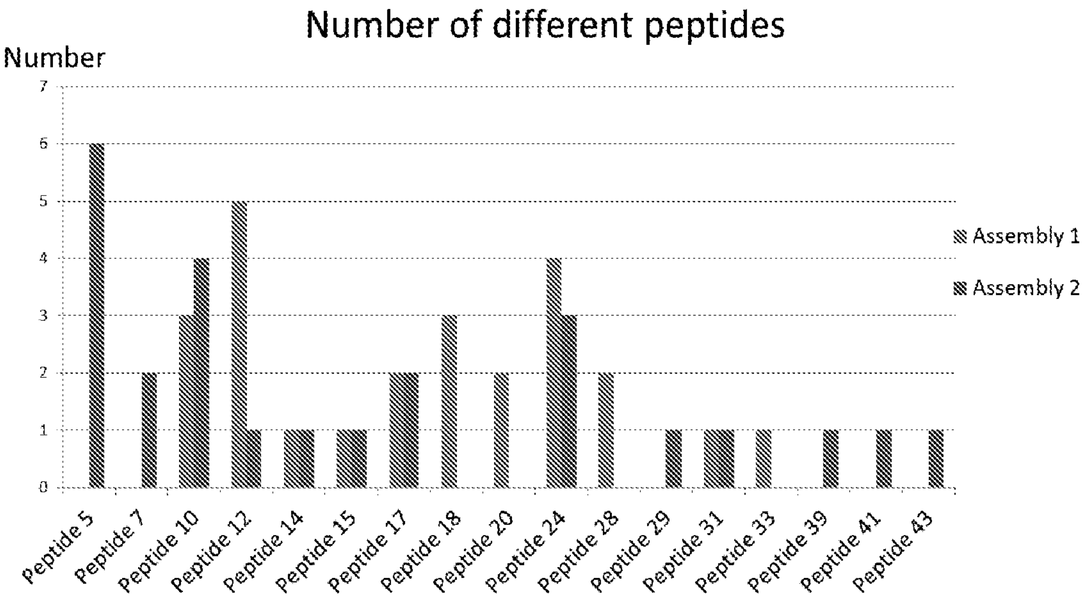

FIG. 7. Number of different peptides present at position one. The light grey bars represent the peptides that were found in the first assembly, the dark grey bars show the peptides of the second assembly.

Figure 8:
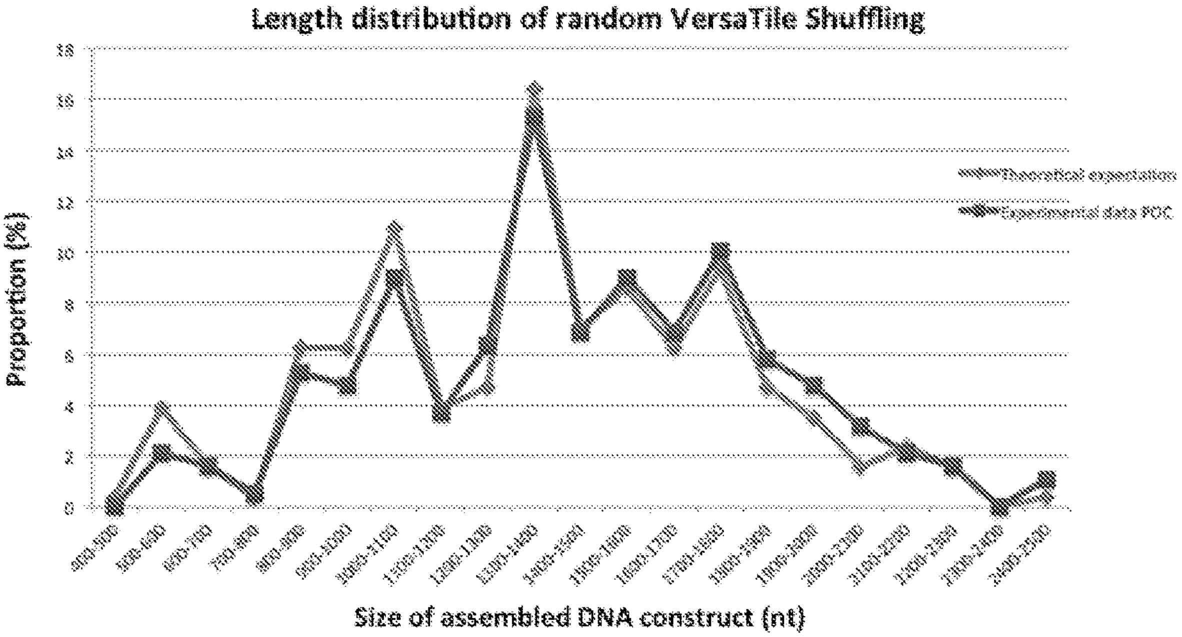

FIG. 8. Length distribution of random VersaTile shuffling. The light grey curve represents the theoretical expectation that was calculated using the R script. The experimental data of the proof-of-concept are represented in the dark grey curve. The curves are relatively similar.

Figure 9:
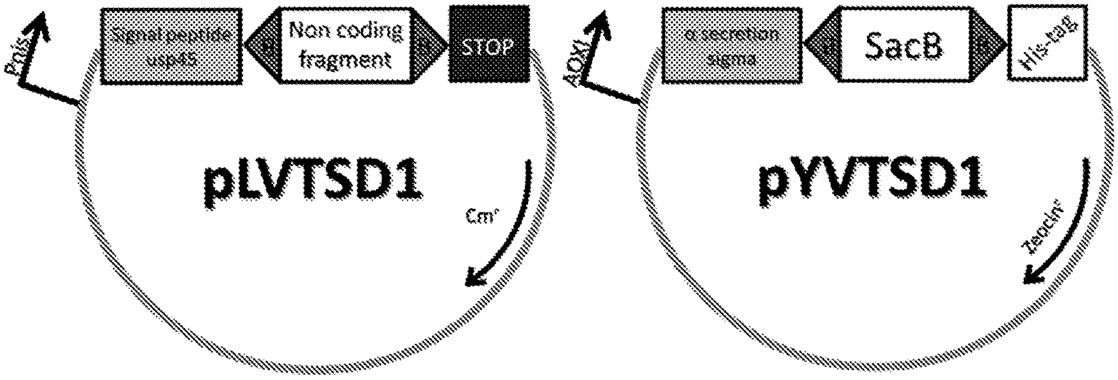

FIG. 9: Overview composition pLVTSD1 and pYVTSD1

Figure 10:
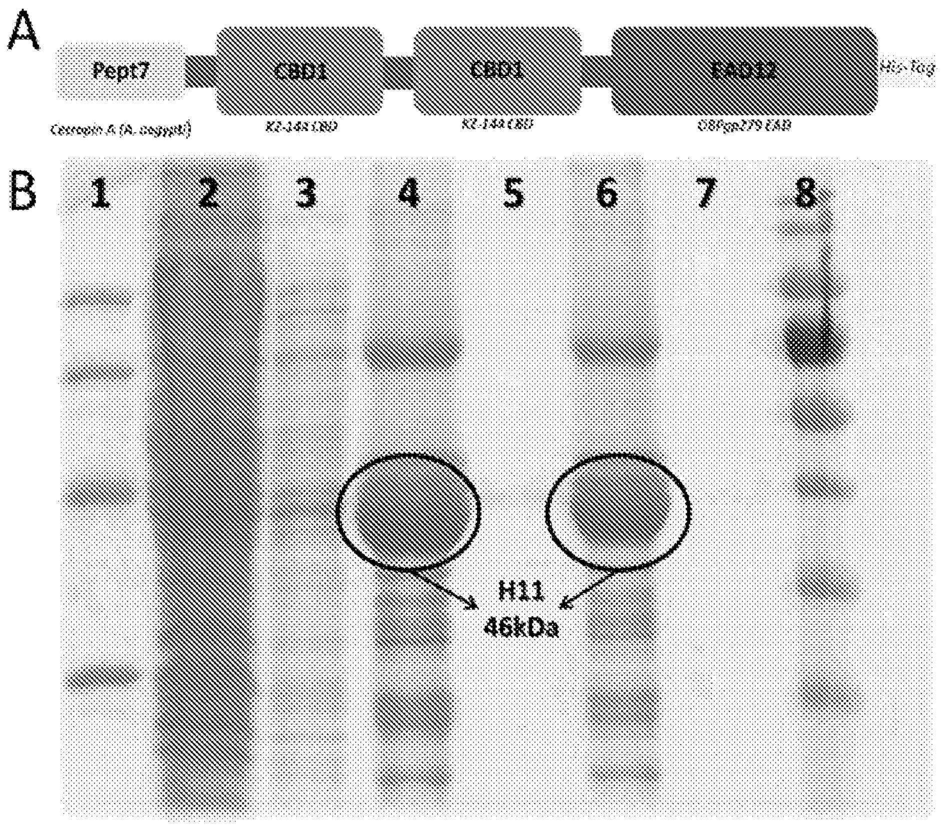

FIG. 10: A. Large scale expression of an engineered endolysin (H11-46 kDa) from which the coding sequence is generated by VersaTile shuffling. B. Lane 1: low molecular weight protein ladder, lane 2: flowthrough, lane 3: wash, lane 4: first elution, lane 5: second elution, lane 6: elution 1 dialyzed, lane 7: elution 2 dialyzed, lane 8: PageRuler prestained protein ladder.

Figure 11:
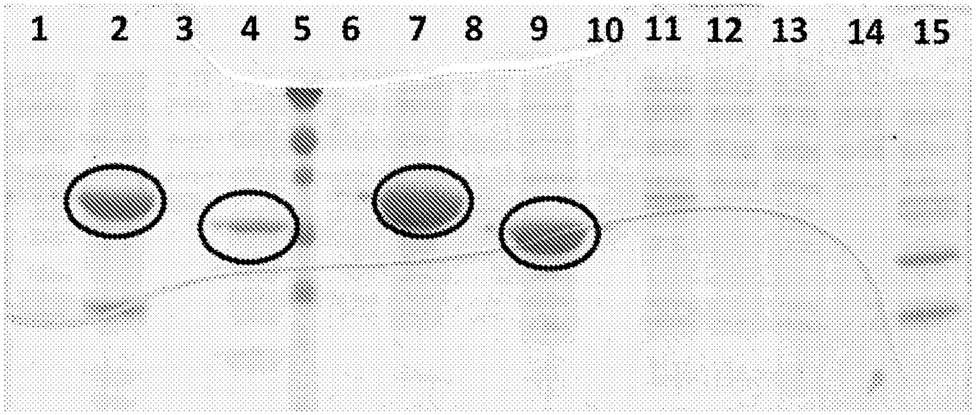

FIG. 11: SDS-page purified fractions (HisPur™ Ni-NTA spin plate from Thermo Scientific) of a small scale expression of 96-different VTS generated proteins in parallel. Lane 1: protein 1, lane 2: protein 2, lane 3: protein 3, lane 4: protein 4, lane 5: PageRuler prestained protein ladder, lane 6: protein 5, lane 7: protein 6, lane 8: protein 7, lane 9: protein 8, lane 10: protein 9, lane 11: protein 10, lane 12: protein 11, lane 13: protein 12, lane 14: protein 13, lane 15: protein 14.

Figure 12:
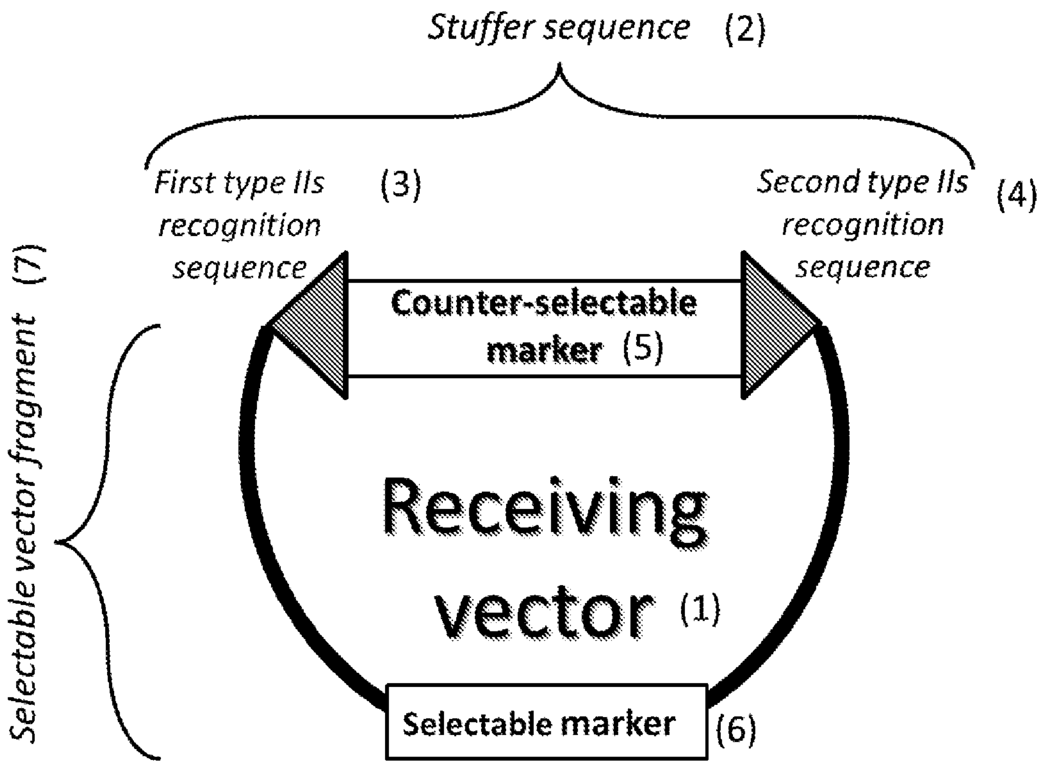

FIG. 12: A schematic representation of a receiving vector.

Figure 13:
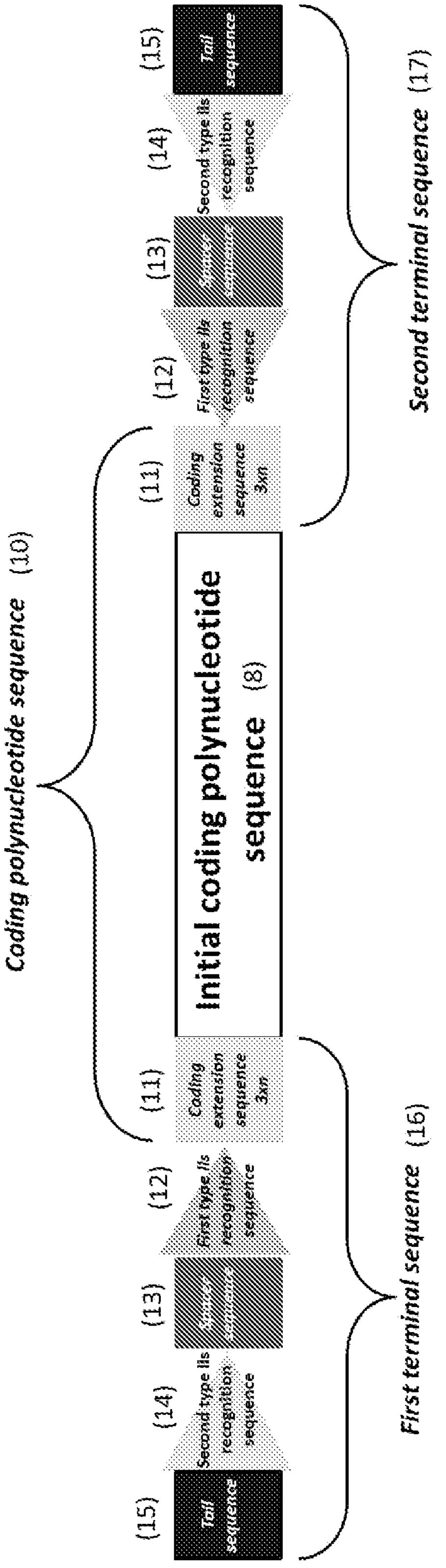

FIG. 13: A schematic representation of an initial coding sequence (8) extended with a first (16) and second (17) terminal sequence.

Figure 14:
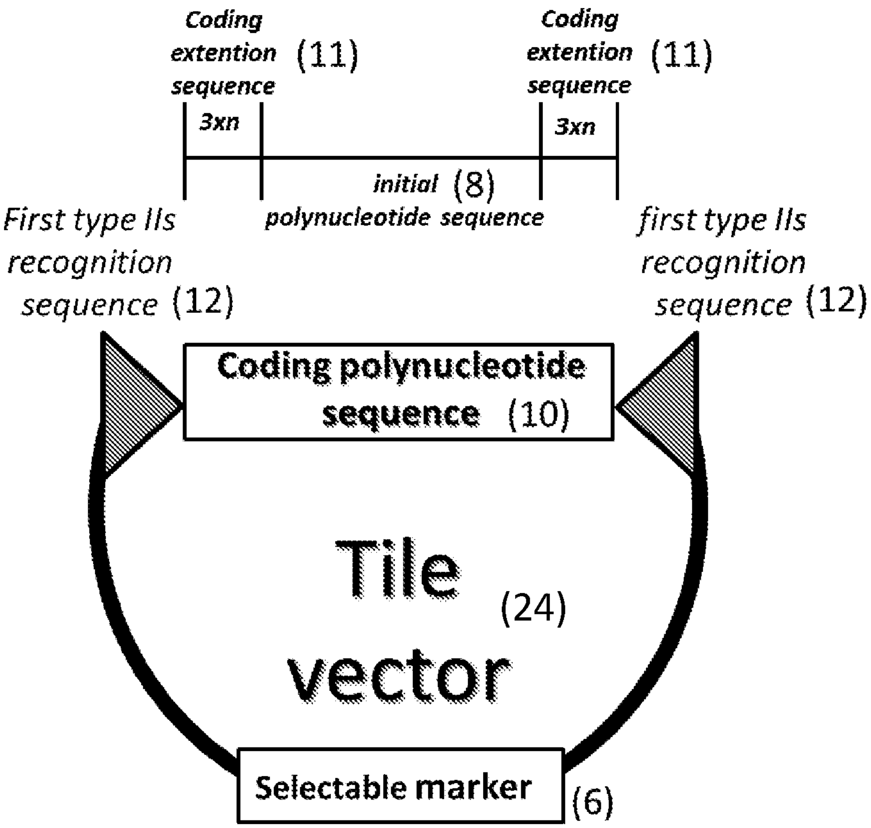

FIG. 14: A schematic representation of a Tile vector.

Figure 15:
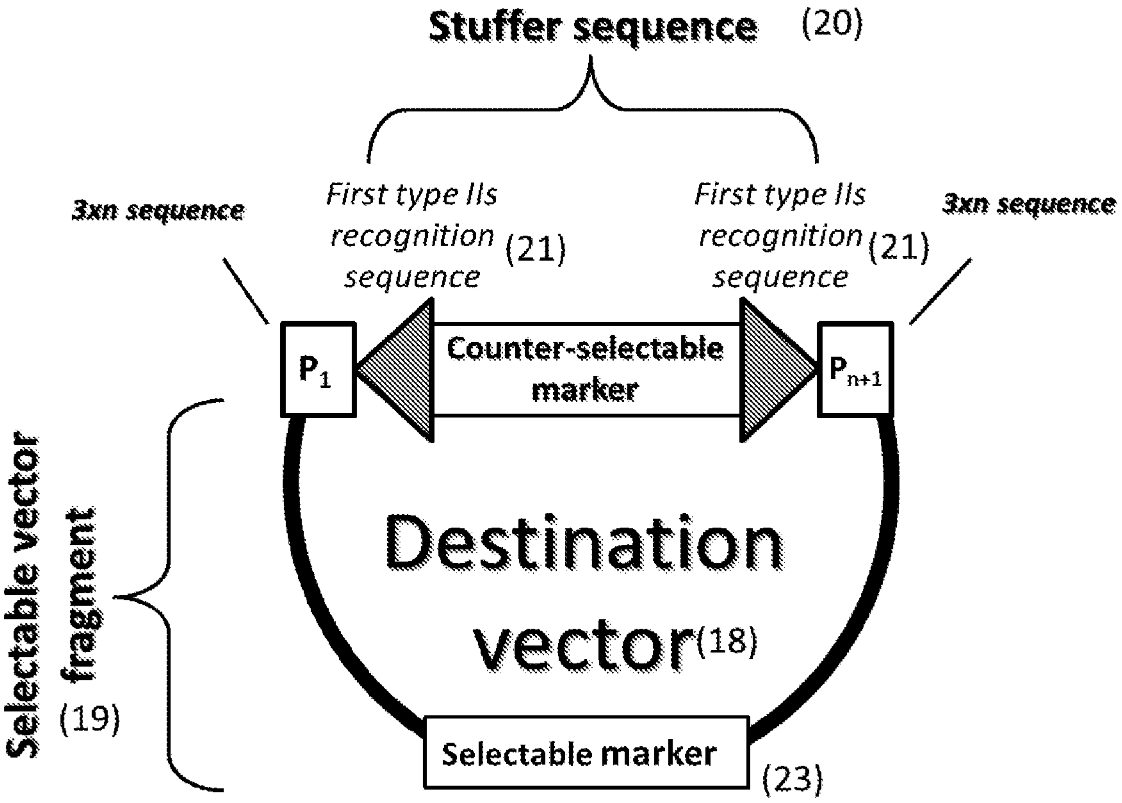

FIG. 15: A schematic representation of a Destination vector.

Figure 16:
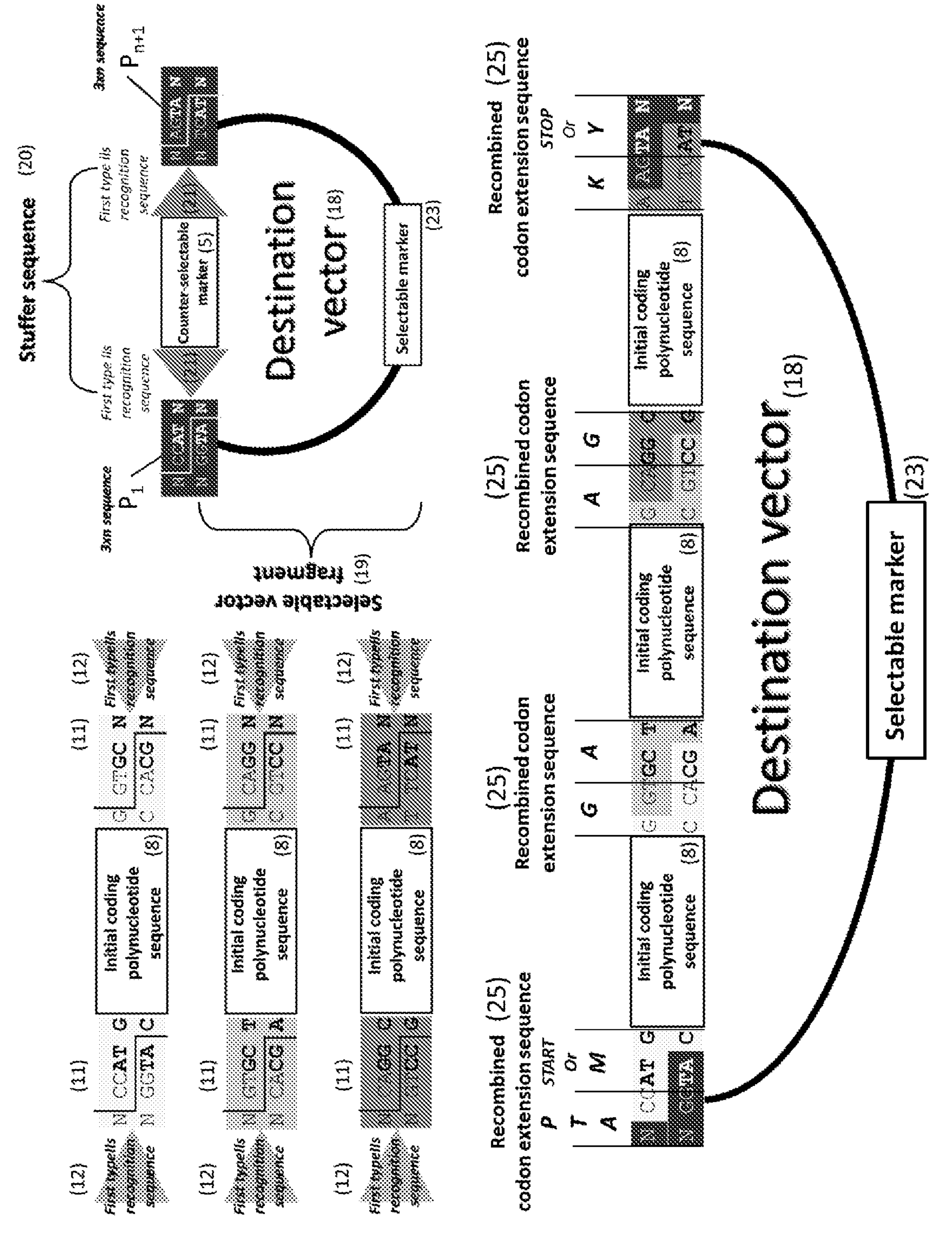

FIG. 16: A schematic representation of VersaTile Shuffling.

FIG. 17: Depicts Table 1, reciting coding extension sequences.

FIG. 18: Depicts Table 3, reciting a blunt end ligation reaction mix.

FIG. 19: Depicts Table 4, reciting a reaction mixture composition VTS reaction.

FIG. 20: Depicts Table 8, reciting a 2-step PCR protocol for Tile amplification with reduced primer dimer formation.

FIG. 21: Depicts Table 9, reciting Versa Tile Shuffling protocol for rational assembly.

FIG. 22: Depicts Table 10, reciting a protocol for semi-random and random assembly.

FIG. 23: Depicts Table 11, reciting a Versa Tile reaction mix.

FIG. 24: Depicts Table 12, reciting a temperature program for Versa Tile Shuffling.

FIG. 25: Depicts Table 13, reciting an error prone protocol.

DETAILED DESCRIPTION

As detailed herein above, the present invention provides a method for preparing a Tile vector, being a vector, which comprises a selectable marker and a coding polynucleotide, wherein said coding polynucleotide is immediately preceded and followed by a type IIs recognition sequence, wherein said preceding and following recognition sequences are recognized by a same type IIs restriction enzyme, but have an opposite orientation.

In that respect, the art, for instance US2014/0329233, provides methods for combining two or more coding polynucleotides into a combined coding polynucleotide, also referred to as product nucleotide. These methods take advantage of DNA digestion by a restriction enzyme, such as a type Us restriction enzyme, that recognizes a non-palindromic sequence, and that cleaves outside its recognition sequence. Following cleavage of DNA by a type IIs restriction enzyme, one of the ends produced by such cleavage lacks any part of the recognition sequence. It is thus possible to design a first polynucleotide sequence comprising a coding polynucleotide sequence flanked by a preceding and following type IIs recognition sequence, which are oriented such that cleavage of said first polynucleotide using type IIs enzymes recognizing said preceding and following recognition sequence results in the release of said coding polynucleotide, wherein said released coding polynucleotide fragment does not comprise any part of said preceding or following type IIs recognition sequences. Hereinafter, such first polynucleotide is referred to as Tile polynucleotide or Tile vector, in case such polynucleotide is a vector.

A further interesting feature of many type IIs restriction enzymes is that their cleavage of a polynucleotide is associated with the formation of an overhang having a known direction and length. In consequence, it is possible to design two or more Tile polynucleotides each comprising a coding polynucleotide flanked by a preceding and following type IIs recognition sequence, such that cleavage of said polynucleotides using the corresponding type IIs enzymes results in the release of a plurality of coding polynucleotides that can combine depending on the design of the overhangs of said released coding polynucleotides in a directed, random or semi-random manner.

With the present invention, the presently available technologies for generation of polynucleotides are further improved. In particular, the present invention provides methods and tools for large scale shuffling of a high number of non-related gene fragments from many different sources to create novel proteins. The present invention is particularly useful to produce a high number of hybrid or fusion proteins.

The present invention specifically focuses on the use of coding extension sequences (3×n) (11) as part of a coding polynucleotide sequence (10). In the text below, we refer to n=2 which we always used in our experimental setups.

In Table 1, set forth in FIG. 17, you can see these choices for three different experimental setups that were performed.

After digestion with a first type IIs recognition sequence, an overhang sequence will be created from each coding extension sequence (3×n) that will be complementary to another overhang sequence in the mixture. FIG. 16 illustrates this for the assembly of three initial coding polynucleotide sequences (8) that are flanked by different coding extension sequences (11) in a destination vector (18). Per Tile position, one can see which coding extension sequence precedes and follows the initial coding polynucleotide sequence. When the VersaTile Shuffling reaction is performed with different Tile vectors (or extended coding polynucleotide sequences), and a destination vector two complementary overhangs of digested coding extension sequences will be recombined into a recombined coding extension sequence (25).

1) The preceding coding extension sequence of the initial coding polynucleotide sequence that occupies the first position in the assembly will recombine with the 3×n sequence P1 of the destination vector. A destination vector is constructed as such that the second triplet of the recombined coding extension sequence is a start codon that is correctly positioned relative to a ribosome binding site, ensuring initiation of translation at this start codon. In case the destination vector encodes an N-terminal purification tag or any other N-terminal sequence, the first triplet of the recombined coding extension sequence will produce another amino acid (P, T, A) depending on the first nucleotide of the 3×n sequence P1 of the destination vector.

2) The following coding extension sequence of the initial coding polynucleotide sequence that occupies the first position in the assembly will recombine with the preceding coding extension sequence of the initial coding polynucleotide sequence that occupies the second position in the assembly. The following coding extension sequence of the initial coding polynucleotide sequence that occupies the second position in the assembly will recombine with the preceding coding extension sequence of the initial coding polynucleotide sequence that occupies the third position in the assembly. New recombined codon extension sequences (25) are created at every junction. Recombined codon extension sequences between two adjacent coding polynucleotide sequences encode for two amino acids. The overhang sequence comprises the last two nucleotides of the first triplet and the first two nucleotides of the second triplet. The exact two amino acids will be determined by the first nucleotide of the following coding extension sequence of the initial coding polynucleotide sequence at position x and the last nucleotide of the preceding coding sequence of the initial coding polynucleotide sequence at the position x+1.

3) The following coding extension sequence of the initial coding polynucleotide sequence that occupies the last position in the assembly will recombine with the 3×n sequence Pn+1 of the destination vector. A destination vector is constructed as such that the second triplet of the recombined coding extension sequence is a stop codon (TAA, TAG; the sixth nucleotide of Pn+1 is A or G). In case the destination vector encodes an C-terminal purification tag or any other C-terminal sequence, the second triplet of the recombined coding extension sequence will be TAC (the sixth nucleotide of Pn+1 is C) encoding an amino acid (Y) instead of a stop codon.

Sarrion-Perdigones et al., 2011 describes ‘Goldenbraid, a method to first assemble a transcriptional unit comprising a promoter, coding sequence and terminator and then a further second assembly of the different transcriptional units in a multigene assembly. For the assembly of the transcriptional units, it is not important that everything remains in frame, because the assembly occurs outside the reading frame. This is in contrast with the VersaTile Shuffling method of the present invention where all the junctions occur within the reading frame. In contrast, GoldenBraid uses a distinct 4 nt that overlaps between adjacent building blocks, resulting in a scarless cloning. The 4 nt are non-coding sequences. This contrasts with VersaTile Shuffling where coding extension sequences of 3×n nucleotides are added to create a scar (linker of two amino acids) between two adjacent Tiles. This is needed in order to stay within the reading frame and to allow combinatorial design.

Vad-Nielsen et al. 2016 makes use of the Golden Gate technology for the assembly of different building blocks with a type IIs restriction/ligation protocol, resulting in a CRISPR gRNA expression array. This array is again not one coding sequence, hence there is no need that all building blocks are assembled in frame. Also here, the authors used distinct 4 nt that are again non-coding sequences between the different gRNA’s.

In the Golden Gate Shuffling techniques as used by Engler et al., 2009, the resulting assembly is a coding sequence. The junctions are thus coding sequences in contrast to Sarrion-Perdigones et al., 2011 and Vad-Nielsen et al., 2016. However, the 4 nt are chosen as such that they are conserved among the different coding sequences that will be shuffled (parental genes). They can thus serve as junction points for a scarless assembly, no additional amino acids are added in between adjacent building blocks, in contrast to the VersaTile Shuffling technique of the present invention. VersaTile Shuffling is suitable for use with complete homology-independent sequences, for which it would be impossible to identify four conserved nucleotides among the parental genes, rendering it useful for many more applications compared to the techniques described in the prior art.

In US20140329233, building blocks are assembled by a type IIs restriction/ligation. However, the recombination sites are not specifically designed to create two specific amino acids as in the VersaTile Shuffling method of the present invention. In VersaTile Shuffling (see FIG. 16), the recombined coding extension sequence results from two coding extension sequences (3×n) with the first two nucleotides of the 4 nt overhang being the last two nucleotides of the first triplet and the last two nucleotides of the 4 nt overhang begin the first two nucleotides of the second triplet. The first nucleotide of the following coding extension sequence of Tile vector at position n and the sixth nucleotide of the preceding coding extension sequence of Tile vector at position n+1 determine finally the exact two amino acids. US20140329233 mentions that an overhang of three nucleotides can be a single codon like methionine/glycine/alanine, and the overhang thus fully encodes the intervening amino acid. An overhang of three nucleotides, however, is less efficient in the assembly process than an overhang of four nucleotides and a lower number of Tiles can be included in a single assembly.

In a first example (i.e. example 9) (directed combination) of the present invention, four Tile polynucleotides are designed to each release such coding polynucleotide of which a first released polynucleotide possesses an overhang having the same direction and length as a complementary overhang of a second released polynucleotide, while the other overhang of said second released polynucleotide possesses an overhang having the same direction and length as a complementary overhang of a third and wherein said first and third released polynucleotides do not have complementary overhangs. In this example the release of these coding polynucleotides using the appropriate type IIs enzymes in the presence of a DNA ligase results in the formation of a product polynucleotide wherein the sequence of the second coding polynucleotide is positioned in between the sequences of the first and third coding polynucleotides.

In a second example (i.e. example 11) (random combination) sixteen (4×4) such Tile polynucleotides are designed to release 4 sets of 4 coding polynucleotides, wherein the respective released coding polynucleotides of a given set either comprise a first, second, third or fourth nucleotide sequence flanked by the same overhang sequences and wherein said first, second, third and fourth nucleotide sequence are the same in each set. Furthermore, the released polynucleotides of said first set possess an overhang having the same direction and length as a complementary overhang of the released polynucleotides of the second set, while the other overhang of the released polynucleotides of said second set possess an overhang having the same direction and length as a complementary overhang of the released coding polynucleotides of the third set and wherein the released polynucleotides of said first and third set do not have complementary overhangs. Furthermore, the released polynucleotide of said fourth set possesses an overhang of the same direction and length as a complementary overhang of the released polynucleotides of the third set wherein the released polynucleotide of said, first, second and fourth set do not have complementary overhangs. Herein, the overhang of the first set is the same as a complementary overhang of the destination vector, and the same applies for the fourth set.

In this second example the release of these coding polynucleotides using the appropriate type IIs enzymes in the presence of a DNA ligase results in the formation of product nucleotides varying in the order of said first, second, third and fourth nucleotide sequences within said product nucleotides.

In a third example (example 10) (semi-random combination) four such Tile polynucleotides are designed to release four coding polynucleotides, of which the first and second released coding polynucleotide comprise a first and second nucleotide sequence, respectively, flanked by the same overhang sequences, while the third and fourth released coding polynucleotides respectively comprise a third and fourth nucleotide sequence each flanked by different overhangs. Further, the said first and second released coding polynucleotide comprise an overhang having the same direction and length as a complementary overhang of said third released polynucleotide, while the other overhang of said third released polynucleotide possesses an overhang having the same direction and length as a complementary overhang of the fourth and wherein said first and second released coding polynucleotides do not have overhangs complementary to an overhang of the fourth released coding polynucleotide. In this third example the release of these coding polynucleotides by the appropriate type IIs enzymes in the presence of a DNA ligase results in the formation of product nucleotides varying in that they either comprise said first or second nucleotide sequence at a first position followed by said third and fourth nucleotide sequence, respectively.

Such methods for combining polynucleotides may involve the integration of the obtained product nucleotide in a vector, preferably a circular vector. This can be achieved using a vector, hereinafter referred to as destination vector, which is designed to be cleaved, preferably using type IIs restriction enzymes, such that after cleavage a vector fragment is generated comprising at one end an overhang complementary with the first overhang of a product polynucleotide and at the other end an overhang complementary with the second overhang of said product polynucleotide, wherein said vector fragment preferably does not comprise any of the type IIs recognition sequences recognized by any of the type IIs enzymes used to either generate the vector fragment or to release said coding polynucleotides from the Tile polynucleotides. The release of said coding polynucleotides and said vector fragment by the appropriate type IIs enzymes in the presence of a DNA ligase results in the formation of such circular vectors comprising a same or varying product polynucleotides. Such vectors can be used to study the properties of the product nucleotides or expression products from said product nucleotides.

It is clear that such methods for combining polynucleotides are valuable tools in the study, design or engineering of proteins. In particular, these methods allow for the design of new proteins by the directed, random or semi-random assembly of multiple coding polynucleotides released from respective Tile polynucleotides into a same or a multitude of different product nucleotides. Subsequently, each of these product nucleotides can be expressed and the resulting proteins can be analyzed to determine their physicochemical, enzymatic, functional or other properties. The variety of proteins generated and thus the chances that any of these proteins has the desired properties can be increased when multiple variants are available for at least one of the released coding polynucleotides, wherein said variants differ in sequence at one or more positions of said coding polynucleotide, however excluding any sequence differences at the positions of the overhangs of the released coding polynucleotides. In this way product nucleotides can be created not only varying in the order of the respective coding polynucleotide sequences, but also in the sequence variants of the coding polynucleotides these product nucleotides comprise. In order to introduce this additional level of variation in routine protein design and engineering projects there is a need for an efficient method for preparing said Tile polynucleotides, in particular Tile vectors. Preferably, such method enables and facilitates the generation of a multitude of Tile polynucleotides or Tile vectors starting from a collection of variants for a given protein coding polynucleotide. Alternatively, such method allows for introducing sequence variations in coding polynucleotide during or after the generation of such Tile polynucleotide or Tile vector.

So in a first object the present invention provides a method for generating such Tile polynucleotides, preferably Tile vectors. Said method is particularly suited for the efficient generation of a library of such Tile polynucleotides, in particular Tile vectors, comprising a multitude of variants of a given coding polynucleotide. More in particular, the present invention provides a method for preparing a Tile vector (24) (FIG. 14), being a vector, which preferably comprises a selectable marker (6) and a coding polynucleotide (10), wherein said coding polynucleotide (10) is immediately preceded and followed by a type IIs recognition sequence (12), wherein said preceding and following recognition sequences are recognized by a same type IIs restriction enzyme, but have an opposite orientation. More particularly, the position and orientation of said preceding and following type IIs recognition sequences (12) provides for the cleavage of said Tile vector by a corresponding type IIs restriction enzyme resulting in the release of said coding polynucleotide having at its respective ends overhang sequences with a known orientation and length, while lacking said preceding and following type IIs recognition sequences. In a first step (a) the preparation of such Tile vector involves providing an initial coding polynucleotide (8), such as for instance a polynucleotide encoding a functional unit of an enzyme or antibody, and extending the respective ends of said polynucleotide with a first (16) and second (17) terminal sequence wherein each of said terminal sequences comprises following elements (FIG. 13):

i. a coding extension sequence (11) (3×n), which is added adjacent to the respective ends of and in frame with the open reading frame of said initial coding polynucleotides (8). Typically, said coding polynucleotide (10) of the Tile vector consists of the initial coding polynucleotide (8) extended with said coding extension sequences (11);

ii. a first type IIs recognition sequence (12) adjacent to said coding extension sequence wherein said first recognition sequence is oriented such that a type IIs restriction enzyme recognizing said first recognition site can cleave within said coding extension sequence generating an overhang of which the sequence is in frame with the open reading frame of said initial coding polynucleotide and wherein said first type IIs recognition sequences of the first and second terminal sequences are recognized by a same type IIs enzyme, but have an opposite orientation;

iii. a spacer sequence (13) adjacent to or within said first type IIs recognition sequence;

iv. a second type IIs recognition sequence (14) adjacent to said spacer sequence wherein said second recognition sequence is oriented such that a type IIs restriction enzyme recognizing said second recognition sequence can cleave said spacer sequence to generate a spacer overhang and wherein said second type IIs recognition sequence is not recognized by a type IIs enzyme recognizing said first type IIs recognition sequence. In particular embodiments said second type IIs recognition sequences of said first and second terminal sequence are selected to be recognized by a same type IIs enzyme;

v. a tail sequence (15) of sufficient length in order to allow binding of a type IIs restriction enzyme to said second recognition sequence.

Depending on the type of restriction enzyme used, the tail sequence (15) may also be absent, in as far as the selected restriction enzyme is capable of binding the second recognition sequence in the absence of such further tail sequence. Therefore, in the context of the invention, the tail sequence (15) is an optional element of the terminal sequences. Furthermore, where a further tail sequence is needed to allow binding of a type IIs restriction enzyme, said tail sequence preferably comprises from 0 to 28 nucleotides; more preferably, it comprises from 3 to 6 nucleotides.

In a second step (b) the preparation of such Tile vector involves providing a receiving vector (1), being a vector, which comprises a first nucleotide sequence comprising a selectable marker (6) positioned between a first (3) and a second (4) type IIs recognition sequence, such that said vector can be cleaved using type IIs recognition enzymes recognizing said first and second type IIs recognition sequences to form:

a stuffer sequence (2) comprising said first (3) and second (4) type IIs recognition sequences, preferably said stuffer sequence further comprises a counter-selectable marker (5); and a selectable vector fragment (7) comprising said selectable marker (6) but lacking said first (3) and second (4) type IIs recognition sequences and having non-complementary terminal overhangs, wherein one overhang is complementary to the spacer overhang obtained after cleaving said first terminal sequence using a type IIs recognition enzyme recognizing said second type IIs recognition sequence of said first terminal sequence, while the other overhang sequence is complementary to the spacer overhang obtained by cleaving said second terminal sequence using a type IIs restriction enzyme recognizing said second type IIs recognition sequences of said second terminal sequence.

Typically, said first (3) and second (4) type IIs recognition sequences of the receiving vector (1) are recognized by a same type IIs enzyme, but have an opposite orientation.

In a third step (c) the preparation of such Tile vector involves incubating a mixture, wherein the mixture comprises:

i. an extended initial coding polynucleotide of step (a);

ii. a receiving vector (1) of step (b);

iii. type IIs restriction enzymes recognizing said second type IIs recognition sequences of the terminal sequences of said extended initial coding polynucleotide;

iv. type IIs restriction enzymes recognizing said first and second type IIs recognition sequence of the receiving vector;

v. a DNA ligase.

In order to limit the number of restriction enzymes to be used in the method of the present invention it is preferred that said first (3) and second (4) type IIs recognition sequence of the receiving vector (1) are recognized by the same type IIs restriction enzyme as the both second type IIs recognition sequences (14) of the first (16) and second (17) terminal sequences of said extended initial coding polynucleotides. In this way a single restriction enzyme provides for the cleavage of the extended initial coding sequence and that of the receiving vector.

For the purpose of carrying out the method of the present invention in a flexible manner a receiving vector was designed, wherein said first and second type IIs recognition sequences are comprised within a first and second multiple cloning site. Said first multiple cloning site comprises a succession of multiple different type IIs recognition sequences, while said second multiple cloning site comprises oppositely oriented type IIs recognition sequences recognized by the same type IIs enzymes as those in the first multiple cloning site. Advantageously, such receiving vector comprising said multiple cloning sites can be used for carrying out the method of the present invention using a single type IIs restriction enzyme in step (c) with any extended initial coding polynucleotide as obtained in step (a), which comprises a first (16) and second (17) terminal sequence each comprising a second type IIs recognition sequence (14) that is recognized by a same type IIs recognition enzyme, which also recognizes a recognition sequence in said multiple cloning sites. Interestingly, such receiving vector comprising said multiple cloning sites may be useful in applications other than the combining or shuffling of protein coding sequences. Therefore, said particular receiving vector is an independent object of the present invention.

The present invention is typically characterized in that the coding polynucleotide sequence (10) comprises an initial coding polynucleotide sequence (8) that is immediately preceded and followed by a coding extension sequence (11) (3×n). Said coding extension sequence (11) typically consists of a set of a multiple of 3 nucleotides (3×n), wherein n can be any number starting from 1; preferably n is in the range between 1 and 10, more preferably n is in the range between 1 and 6, even more preferably n is 1, 2, 3, 4, 5 or 6; most preferably n is 2. Where n is selected to be 2, the 6 nucleotides (3×2) encodes two amino acids. Specifically, preferred coding polynucleotide sequences (10) are selected from the list comprising: ACCATG, GGTGCT, GCAGGC, GGAAGC, AAGTAA, AGCACA, CCAACG, ACGAGC, CCGTCT, TCTGGT, GGTTCA (see also Table 1 as set forth in FIG. 17 for the corresponding coding extension sequences).

The overhang created by digestion with the type IIs restriction enzyme (mostly 4 nucleotides) comprises the last two nucleotides of the first codon, and the first two nucleotides of the second codon. The coding extension sequences of two adjacent initial coding polynucleotide sequences must not be the same, as long as the generated overhang (mostly 4 nucleotides) is complementary. The first and sixth nucleotide of the coding extension sequence can thus be freely chosen, determining the two (or more) amino acids.

In a particular embodiment of the method of the present invention said initial coding polynucleotide (8) extended with said terminal sequences (16, 17) (see step (a)) is prepared using a DNA synthesis method.

In a particular embodiment of the method of the present invention the initial coding polynucleotide (8) is extended with said terminal sequences (16, 17) (see step (a)) using a polymerase chain reaction (PCR), involving the use of tailed forward and reverse primers annealing on the respective ends of said initial coding polynucleotide, wherein said tail of the forward primer adds the first terminal sequence (16) and the tail of the reverse primer adds the second terminal sequence (17). In a further particular embodiment the primers and reaction conditions used in said PCR are selected in order to promote the introduction of directed or random mutations within said initial coding sequence. For instance, said PCR reaction conditions can be error prone PCR conditions thus generating a multitude of vectors, which vary from one another in that they comprise random mutants of said initial coding polynucleotide.

In another particular embodiment the method of the present invention comprises an additional step of introducing one or more directed mutations in the sequence of the initial coding polynucleotide comprised in said Tile vector, said additional step comprising the use of the Kunkel method, PCR site-directed mutagenesis with mismatch primers or whole plasmid mutagenesis (e.g. Quickchange method).

In a second object, the present invention provides a Tile vector (24) comprising a selectable marker (6) and a coding polynucleotide sequence (10) immediately preceded and followed by a type IIs recognition sequence (12), wherein said preceding and following type IIs recognition sequences (12) are recognized by a same type IIs restriction enzyme but have an opposite orientation. Said Tile vector is further characterized in that the coding polynucleotide sequence (10) comprises an initial polynucleotide sequence (8) immediately preceded and followed by two coding extension sequences (11) (3×n), being in frame with the open reading frame of the initial coding sequence (8).

In a third object, the present invention provides a polynucleotide sequence comprising an initial coding polynucleotide sequence (8) and a first and second terminal sequence (16, 17), wherein each of said first and second terminal sequence (16, 17) comprises the following elements:

i. a coding extension sequence (11) (3×n), which immediately precedes and follows the initial coding polynucleotide sequence (8) and which is in frame with the open reading frame of said initial coding polynucleotide sequence (8);

ii. a first type IIs recognition sequence adjacent to said coding extension sequence (11) (3×n) wherein said first type recognition sequence is oriented such that a type IIs restriction enzyme recognizing said first recognition site can cleave within said coding extension sequence (11) (3×n) generating an overhang and wherein said first type IIs recognition sequences of the first and second terminal sequences are recognized by a same type IIs enzyme, but have an opposite orientation;

iii. a spacer sequence (13) adjacent to or within said first type IIs recognition sequence (12);

iv. a second type IIs recognition sequence (14) adjacent to said spacer sequence (13) wherein said second type IIs recognition sequence (14) is oriented such that a type IIs restriction enzyme recognizing said second type IIs recognition sequence (14) can cleave said spacer sequence (13) to generate a spacer overhang and wherein said second type IIs recognition sequence (14) of the first and second terminal sequences are not recognized by a type IIs enzyme recognizing said first type IIs recognition sequences (12);

v. a tail sequence (15) of sufficient length in order to allow binding of a type IIs restriction enzyme to said second recognition sequence (14).

In a further embodiment, said artificial polynucleotide sequence can be used in a method for preparing a Tile vector according to any of the embodiments of the invention as outlined herein above.

In a fourth object the present invention provides a method for using such Tile vectors for joining two or more coding polynucleotides to form a product polynucleotide. Typically, said product polynucleotide is integrated in a vector. The method according to this second object of the present invention involves the incubation of a mixture comprising:

i. two or more Tile vectors obtained according to the method according to the first object of the present invention, each such Tile vector comprising a coding polynucleotide sequence (10) that comprises two coding extension sequences (11) (3×n), wherein said coding polynucleotide sequence (10) is immediately preceded and followed by said type IIs recognition sequences (12), wherein said preceding and following recognition sequences (12) of said vectors are recognized by a same type IIs restriction enzyme;

ii. a type IIs restriction enzyme that recognizes said preceding and following types IIs recognition sequences (12) within said Tile vectors and cleaves from each of said vectors a coding polynucleotide sequence (10), wherein at least one overhang of each released coding polynucleotide is complementary to at least one overhang of one other released coding polynucleotide;

iii. a destination vector (18) (FIG. 15) comprising a first nucleotide sequence comprising a selectable marker positioned between two first type IIs recognition sequences (21), wherein said first type IIs recognition sequences (21) are recognized by a type IIs restriction enzyme, preferably a same type IIs restriction enzyme, but have an opposite orientation, such that said vector can be cleaved using a type IIs restriction enzyme recognizing said first type IIs recognition sequences (21) to form:

a stuffer sequence (20) comprising said first type IIs recognition sequences (21), preferably said stuffer sequence further comprises a counter-selectable marker; and a selectable vector fragment (19) comprising said selectable marker (23) but lacking said first type IIs recognition sequences (21) and having non-complementary terminal overhangs, wherein one overhang is complementary to at least one overhang of any of said released coding polynucleotides, while the other overhang is complementary to at least one other overhang of any of said released coding polynucleotides;

iv. a type IIs restriction enzyme recognizing said first type IIs recognition sequences (21) of said destination vector. In a particular embodiment of the method according to the fourth object of the present invention said first type IIs recognition sequences (21) of the destination vector (18) are recognized by a same type IIs restriction enzyme recognizing said preceding and following recognition sequences of said Tile vectors. In this way a same type IIs restriction enzyme can be used for cleaving said Tile vectors (24) and said destination vector (18).

v. a DNA ligase.

Preferably, the Tile vectors as used in the method according to this fourth object are prepared according to the method of the first object of the present invention.

Typically, the sequences of coding polynucleotides differ between said Tile vectors. This sequence variation can reside (i) in that Tile vectors comprise variants of a given coding polynucleotide, (ii) in that Tile vectors comprise coding polynucleotides encoding different functional or other units of a protein and/or (iii) in that Tile vectors are designed to release coding polynucleotides having different overhang sequences.

Typically, the order wherein the released coding polynucleotide combine in a product nucleotide is determined by the complementarity of the overhangs of the respective released coding polynucleotides, which is in turn determined by the design of the coding extension sequences as integrated in the respective coding polynucleotides. Preferably, in the method according to the fourth object of the present invention a selection of Tile vectors is designed to induce the formation of a product nucleotide comprising a predefined number of linked coding polynucleotides and wherein the overhang sequences of the released coding polynucleotides define the position of said coding polynucleotide within the order of the coding polynucleotides in the product nucleotide. Furthermore, the Tile vectors can be selected to provide two or more released coding polynucleotides differing in nucleotide sequence but sharing the same overhang sequences wherein said method results in the formation of different product nucleotides varying in the nucleotide sequence at the position in said product nucleotide as defined by said shared overhang sequences of said released coding polynucleotides. Such released coding polynucleotides differing in nucleotide sequence but sharing the same overhang sequences may comprise different variants or mutants of a polynucleotide encoding a given protein unit. Alternatively such released coding polynucleotides differing in nucleotide sequence but sharing the same overhang sequences comprise different polynucleotides encoding different protein units.

Typically, the method according to fourth object of the present invention is performed using a selection of Tile vectors designed to release coding nucleotides of which the complementarity of their respective overhangs favors, preferably restricts, the pairing of overhangs to overhangs that have a same direction. In this way the obtained product nucleotide combines said coding polynucleotides in a single reading frame.

The present invention further provides a destination vector (18) comprising a selectable marker (23), two first type IIs recognition sequences (21) and a counter-selectable marker, characterized in that

- the selectable marker (23) is positioned between two (3×n) sequences ($P_1$ and $P_{n+1}$) each of said sequences followed by a first type IIs recognition sequence (21);
- the two first type IIs recognition sequences (21) are recognized by a same type IIs restriction enzyme recognizing said two first type IIs recognition sequences (21).

In a specific embodiment, the destination vector (18) is selected from the list comprising pVTSD1-pVTSD9 (SEQ ID No 13-SEQ ID No 21); more specifically, the destination vector is selected from the list comprising: pVTSD2 (SEQ ID No 14), pVTSD3 (SEQ ID No 15), pVTSD4 (SEQ ID No 16), pVTSD5 (SEQ ID No 17), pVTSD6 (SEQ ID No 18), pVTSD7 (SEQ ID No 19), pVTSD8 (SEQ ID No 20), pVTSD9 (SEQ ID No 21).

The present invention also provides a receiving vector (1) comprising a first nucleotide sequence comprising a selectable marker (6) positioned between two multiple cloning sites, a first multiple cloning site comprising a succession of multiple different type IIs recognition sequences and a second multiple cloning site comprising oppositely oriented type IIs recognition sequences recognized by the same type IIs enzymes as those in the first multiple cloning site, wherein said multiple cloning sites comprise first (3) and second (4) type IIs recognition sequences; such that said vector can be cleaved using type IIs recognition enzymes recognizing said first (3) and second (4) type IIs recognition sequences to form:

- a stuffer sequence (2) comprising said first (3) and second (4) type IIs recognition sequences; and
- a selectable vector fragment (7) comprising said selectable marker (6) but lacking said first and second type IIs recognition sequences and having non-complementary terminal overhangs.

The receiving vector is featured by the presence of a multitude of type IIs restriction sites (multiple cloning site), which gives the experimenter more flexibility if one of the recognition sites would be present in the coding polynucleotide sequence that has to be converted to a Tile vector. Two type IIs multiple cloning sites, each with an opposite orientation, are present in the receiving vector, together flanking a sacB sequence which was inserted as a negative selection marker. To have functional multiple cloning sites, present recognition sites of those type IIs restriction enzymes were also removed from the backbone. Additionally, the whole plasmid was further reduced to serve merely as a Tile carrier, including removal of promotors, reporter genes and expression element.

EXAMPLES

Example 1: General Protocol for the Construction of Tile Vectors Using Blunt-End Ligation A Tile is the initial coding sequence of the respective module flanked by coding extension sequences (11) at each side and inwards oriented first type IIs recognition sites (12) at the ultimate ends. When the Tile is present in the receiving vector it will be referred to as Tile vector. Generally, the initial coding polynucleotide sequence of the respective module (>100 bp) was amplified with a proofreading PCR enzyme using standard PCR conditions and primers. If an internal type IIs recognition site was present in the initial coding polynucleotide sequence, this has been removed first using the splicing-by-overlap-extension (SOE) technique using overlapping primers including the mutated mismatch to modify the type IIs recognition site (FIG. 2). Different site-directed mutagenesis methods with a similar outcome can be used.

Specific PCR products were purified. In case of a-specific products, PCR conditions were optimized or a gel extraction protocol was used to obtain a pure, specific product. Small initial coding polynucleotide sequences (<100 bp) were generated by primer hybridization. The primers were designed in such a manner that they have at least 15 overlapping base pairs, which after hybridization results in the complete initial coding polynucleotide sequence. The primers were mixed in equimolar amounts (5 μM) and incubated in a heat block with a starting temperature of 95° C. (5 min), followed by a gradual cool down to room temperature (20° C.). For fragments smaller than 60 bp, primer hybridization resulted in the complete initial coding polynucleotide sequence, whereas for fragments with a length between 60 and 100 bp an additional fill-in step was necessary to fill in the overhanging single-stranded DNA.

The fill-in reaction was performed with Pfu DNA polymerase (10 minutes at 72° C.).

The four used receiving vectors, were constructed from a pUC19 vector backbone. Herein an internal BsaI recognition site located in the ampicillin (amp) resistance gene was previously removed (pUC19*) through site-directed mutagenesis to prevent digestion of the vector backbone during the VersaTile shuffling reaction (see FIG. 1). To create the four receiving vectors (pVTSE1, pVTSE2, pVTSE3, pVTSE4, or in general pVTSEx with x referring to the specific set of coding extension sequences corresponding to a specific position in the assembly) a cassette containing the coding extention sequences ($P_n$ and $P_{n+1}$ with n the position of the Tile in the assembly, FIG. 15) flanked by two BsaI recognition sites was previously inserted in the multiple cloning site between the Hind III and XbaI recognition sites (FIG. 3). The resulting four empty receiving vectors were linearized by inverse PCR (iPCR). For each pVTSEx a set of primers was designed complementary to the insert cassette and a part of the vector backbone (see Table 2).

TABLE 2

Overview of the used primers for iPCR.

| Receiving vector | Forward primer | Reverse primer |
|---|---|---|
| pVTSE1 | GGTGCT**GAGACC**TCTAGAGG (SEQ ID No 1) | CATGGT**GAGACC**AAGCTTGG (SEQ ID No 2) |
| pVTSE2 | GCAGGT**GAGACC**TCTAGAGG (SEQ ID No 3) | TGCACT**GAGACC**AAGCTTGG (SEQ ID No 4) |
| pVTSE3 | GGAAGC**GAGACC**TCTAGAGG (SEQ ID No 5) | ACCTGT**GAGACC**AAGCTTGG (SEQ ID No 6) |
| pVTSE4 | AAGTAG**GAGACC**TCTAGAGG (SEQ ID No 7) | GCTTCT**GAGACC**AAGCTTGG (SEQ ID No 8) |

BsaI in bold and the coding extension sequences underlined.

The inverse PCR (iPCR) was performed with Pfu DNA polymerase (Thermo Scientific). The extension step (72° C.) was extended to 6 minutes because of the length of the desired product (2710 bp). The resulting linearized pVTSEx was controlled through gel electrophoresis and purified either with PCR purification or gel extraction. Blunt-end ligation was used to ligate the insert fragments (initial coding polynucleotide sequence) in the linearized pVTSEx. The linearized pVTSEx (50 ng) and the insert fragment were mixed in a 1:3 molar ratio respectively. The composition of the used reaction mixture is given in Table 3 set forth in FIG. 18 (all components were ordered from Thermo Scientific). The reaction mix was incubated for 1 hour at 22° C. followed by an inactivation step of 10 minutes at 65° C.

Chemically competent *E. coli* TOP10 cells (using the rubidium chloride method) were transformed with the ligation mixture of pVTSEx and an insert fragment. Transformation was done by adding 10 μL of the respective ligation mix and incubating this mixture for 30 minutes on ice. After incubation a heat shock (42° C.) was applied and 1 mL LB medium was added. Subsequently, the cells were incubated for one hour at 37° C. to allow for the development of antibiotic resistance. After incubation the cells were plated (900 μL and 100 μL) on selective plates containing 100 μg/ml ampicillin and X-gal. For the blue-white screen an X-gal solution in dimethylformamide (10 mg/mL) was made of which 2 μL per mL medium was added. A directional PCR is performed with one primer located on the pUC19* vector backbone (M13-forward-D20 primer pUC19) and one primer on the insert in the opposite direction. Amplification will only take place when the initial coding polynucleotide is inserted in the correct orientation. From the selective plate eight colonies for each construct were picked up and dissolved in a DreamTaq DNA polymerase (Thermo Scientific) reaction mix. DreamTaq green buffer was used so that after the directional PCR the samples could be immediately loaded for gel electrophoresis. For each analysed colony a replicate was streaked on a new selective plate. Successful clones as analysed by gel electrophoresis were sequence verified by Sanger sequencing and a plasmid stock/glycerol stock was prepared.

Example 2: General Protocol for the Construction of Tile Vectors Using Sticky-End Type II Restriction Enzymes Tile construction was performed using standard restriction and ligation steps. The initial coding polynucleotide sequences were now amplified with primers comprising subsequently a tail sequence (15), a restriction site (HindIII for the forward primer and XbaI for the reverse primer), a first type IIs recognition sequence and the respective coding extension sequences in the 5' terminus of each primer. The pVTSEI receiving vectors used for sticky-end ligation is universal and not specific for each position in the final assembly, in contrast to the pVTSEx used in example 1. The pVTSEI vector is obtained by removal of the internal BsaI recognition site in the ampicillin resistance gene by site-directed mutagenesis starting from pUC19.

Specific PCR products are purified, double digested with HindIII and XbaI and re-purified. The universal pVTSEI vector is prepped, double digested with HindIII and XbaI, dephosphorylated and purified. With a standard ligation and transformation protocol, new clones are obtained, analysed by PCR clone analysis and sequence verified. Clones containing a correct Tile vector with initial coding polynucleotide sequence are stored as a plasmid and glycerol stock.

Example 3: General Protocol for the Construction of Tile Vectors Using Type IIs Restriction Enzymes In a different protocol, the approach in example 2 was further modified. The restriction sites in the primers for PCR were exchanged for the inwards oriented recognition site of the type IIs restriction enzyme BpiI (BbsI) (second type IIs recognition sequence, 14) followed by 6 nt (spacer sequence, 13). The complete order of the different parts of each primer is thus a tail sequence (15), an inwards oriented BpiI recognition site (14), six nucleotides of which 4 are conserved (13), an inwards oriented BsaI recognition site (12), a coding extension sequence and nucleotides matching the end of the fragment that will be amplified. A new universal receiving vector (pVTSEII—SEQ ID No 9) was constructed starting from pVTSEI. Between the HindIII and XbaI restriction sites, a cassette comprising subsequently the same 6 nucleotides as in the spacer sequence of the forward primer of the insert (NNGATA), an outward oriented BpiI recognition site, the sacB gene, an outward oriented BpiI recognition site and the same six nucleotides of the spacer sequence of the reverse primer of the insert (NNAAGC) (FIG. 4).

Mixing the purified PCR product, the pVTSEII receiving vector, BpiI and T4 DNA ligase in a single tube followed by a temperature program cycling between optimal ligation and digestion temperature (Table 4, set forth in FIG. 19), followed by step-wise heat inactivation of the ligase and the type IIs restriction enzyme, respectively, results in a one-step ligation of the initial coding polynucleotide sequence flanked by the first and second terminal sequence in the pVTSEII.

A further extension of the protocol is the construction of pVTSEIII (SEQ ID No 10) which contains a type IIs multiple cloning site comprising several type IIs recognition sites (Table 5) oriented in the same direction as BpiI in pVTSEII (FIG. 4). The presence of more than one type IIs recognition site enables the experimenter to choose the type IIs restriction enzyme that is most appropriate for Tile vector construction. This contributes to the versatility of this Tile vector construction method as the used type IIs restriction enzyme can be selected based on the absence of its recognition site in the respective Tile, this in contrast to pVTSEII where only BpiI can be used.

TABLE 5

Overview type IIs restriction enzymes (recognition and restriction sequence) present in the pVTSEIII multiple cloning site.

| Name | Upstream | Downstream | Optimal temperature |
|---|---|---|---|
| BpiI | GAAGACNN<br>CTTCTGNNNNNN<br>(SEQ ID NO 22) | NNNNNNGTCTTC<br>NNCAGAAG<br>(SEQ ID NO 23) | 37° C. |
| BfuAI | ACCTGCNNNN<br>TGGACGNNNNNNNN<br>(SEQ ID NO 24) | NNNNNNNNGCAGGT<br>NNNNCGTCCA<br>(SEQ ID NO 25) | 50° C. |
| SapI | GCTCTTCN<br>CGAGAAGNNNN<br>(SEQ ID NO 26) | NNNNGAAGAGC<br>NCTTCTCG<br>(SEQ ID NO 27) | 37° C. |
| BtgZI | GCGATG$N_{10}$<br>CGCTAC$N_{10}$NNNN<br>(SEQ ID NO 28) | NNNN$N_{10}$CATCGC<br>$N_{10}$GTAGCG<br>(SEQ ID NO 29) | 60° C. |
| BsmbI | CGTCTCN<br>GCAGAGNNNNN<br>(SEQ ID NO 30) | NNNNNGAGACG<br>NCTCTGC<br>(SEQ ID NO 31) | 55° C. |
| BseRI | GAGGAG$N_8$NN<br>CTCCTC$N_8$<br>(SEQ ID NO 32) | $N_8$CTCCTC<br>NN$N_8$GAGGAG<br>(SEQ ID NO 33) | 37° C. |

The pVTSEIII is constructed starting from the pVTSEII. pVTSEII is linearized with tail bearing primers in such a manner that the sacB fragment is removed and subsequently an outward oriented BseRI and inward oriented BsmbI, BtgZI an BsaI recognition sites are added to the linear vector. Similarly the sacB fragment is amplified with tail bearing primers resulting in the sacB fragment flanked by outward oriented BpiI, BfuAI, SapI and BtgZI recognition sites respectively and an inward oriented BsaI recognition site. The BsaI recognition sites present in the generated linear vector and sacB fragment are positioned in such a manner that after mixing both with T4 DNA ligase and BsaI, the pVTSEIII is constructed in a one-step, one mixture protocol, hereby avoiding the laborious steps of a conventional restriction ligation reaction.

The production of Tile vectors using the pVTSEIII is similar to the protocol for pVTSEII (Table 4, FIG. 13). However, depending on the temperature profile of the used type IIs restriction enzyme, incubation time, temperature and the amount of enzyme used should be adjusted.

Example 4: Use of Primer Cassettes for Tile Vector Construction

In a different protocol, the approach in example 3 (general protocol for the construction of Tile vectors using Type IIs restriction enzymes) was modified for the use of primer cassettes in addition to PCR amplified fragments. Herein the respective initial coding polynucleotide sequence is fully synthesized as a single stranded DNA strand, including the first and second terminal sequences. For fragments with a maximum length of 60 base pairs (including the first and second terminal sequences) two fully complementary primers are synthesized and annealed (Table 6), resulting in a double stranded polynucleotide including the respective initial coding polynucleotide sequence and flanking first (16) and second (17) terminal sequences. Herein, the order of the different parts in the forward primer is as follows: a tail sequence of three random nucleotides (15), an inwards oriented second Type IIs recognition site (14), a spacer sequence (13) of six nucleotides of which three or four nucleotides are conserved, an inwards oriented first Type IIs recognition site (12), a correct coding extension sequence (3×n) (11), the initial coding polynucleotide sequence (8), a correct coding extension sequence (3×n) (11), an inwards oriented first Type IIs recognition site (12), a spacer sequence (13) of six nucleotides of which three or four nucleotides are conserved, an inwards oriented second Type IIs recognition site (12) and a tail sequence (15) of 3 random nucleotides. The reverse primer is the full reverse complement of said first primer and as such fully complementary. Addition of both primers in equal concentrations results in a double stranded polynucleotide including the initial coding polynucleotide sequence and respective terminal sequences, analogous to the PCR amplified fragments in example 1-3.

TABLE 6

Protocol for the generation of primer cassettes

| Component | Amount | Reaction |
|---|---|---|
| Primer 1 | 10 μL of 10 mM stock | Incubate mixture for 2 min at |
| Primer 2 | 10 μL of 10 mM stock | 95° C. and gradually cool down to room temperature |

For initial coding polynucleotide sequences with a length of more than 60 bp multiple primers are annealed, followed by a final fill in polymerase reaction (Table 7) in order to fill in the final gaps in the double stranded polynucleotide sequence. The primers are designed in such a way that mixing them in equal concentrations results in the complete initial coding polynucleotide sequence including the first (16) and second (17) terminal sequences. Herein, there is a minimal 15 nucleotide overlap between two consecutively overlapping primers, designed as such that they ensure primer annealing in the correct order. The first primer contains the first terminal sequence (16), and the first part of the initial coding polynucleotide sequence. The following primer contains at least 15 nucleotides in reverse complement to the end of the first primer and the second part of the initial coding polynucleotide sequence. This is repeated as such until the initial coding polynucleotide sequence is fully covered. The last primer has 15 nucleotides in reverse complement to the end of the previous primer, the last part of the initial coding polynucleotide sequence and the second terminal sequence (17). Mixing of these primers in equal concentration followed by heating and gradual cooing down results in a DNA molecule covering the initial coding polynucleotide sequence and the both the first (16) and second (17) terminal sequence, which is partially double stranded but still contains single stranded stretches where the primers do not have a complementary part. The resulting fragments are used as a template in a final fill in polymerase reaction (Table 7) to fill in the single stranded stretches, resulting in a double stranded polynucleotide (terminal sequences and initial coding polynucleotide sequence) analogous to example 1-3 and the fully overlapping primer cassettes.

TABLE 7

Final fill in polymerase reaction of overlapping primer sets

| component | amount | Reaction |
|---|---|---|
| Overlapping fragments | 20 μL | The reaction mixture is incubated |
| 10x Pfu Buffer | 5 μL | for 10 minutes at 72° C. |
| 2 mM dNTP mix | 5 μL | The resulting mixture is PCR |
| Pfu (2.5 U/μL) polymerase | 1 μL | purified and used for Tile |
| ultrapure $H_2O$ | 19 μL | construction |
| Total volume | 50 μL | |

The protocol for cloning of the double stranded polynucleotides (obtained by primer annealing as described in this example) in the respective receiving is completely analogous to the protocol explained in example 3.

This was tested and verified using primer cassettes (up to 60 bp), and DNA fragments (>60 bp) composed of fully overlapping as well as partially overlapping primers. Cloning of the constructed primer cassettes/double stranded polynucleotides in the respective receiving vector was done with an efficiency larger than 95%.

Example 5: Use of DNA Fragments Produced by Gene Synthesis for Tile Vector Construction In a different protocol the approach of examples 3 and 4 was further modified for the use of chemically synthesized double stranded polynucleotide fragments (e.g DNA strings, gBlocks). Herein the respective initial coding polynucleotide sequence including the first (16) and second (17) terminal sequences is fully generated through gene synthesis. The respective order of the different parts in these synthesized double stranded fragments is as follows: tail sequence (15), a second type IIs recognition site (14), spacer sequence (13), a first type IIs recognition sequence (12), coding extension sequence (11), the initial coding polynucleotide sequence (8), a coding extension sequence (11), a first type IIs recognition site (12), spacer sequence (13), a second type IIs recognition site (14) and a tail sequence (15). The order of the different parts in the chemically synthesized fragments is fully analogous to the PCR amplified fragments or primer cassettes in examples 1-4, and only differ in the method used to obtain the polynucleotide comprising the coding sequences and the respective terminal sequences (16, 17). The protocols for cloning chemically synthesized fragments in the respective receiving is completely analogous to the protocol explained in example 3.

Example 6: Optimized Protocol for Cloning PCR Amplified Polynucleotides in Receiving Vectors The protocol from Example 3 was further optimized for the construction of Tile vectors starting from PCR amplified polynucleotides to avoid unintended cloning of primer dimers which may result from the PCR reaction. Indeed, a frequently occurring problem was the formation of primer dimers due to the long primer tails adding the respective terminal sequences (16, 17). Preferred cloning of the resulting primer dimers significantly reduced the efficiency of the Tile construction protocol and as such there was a significant margin for optimization. In order to prevent this problem, two optimizations were applied: (1) The introduction of a 2-step PCR protocol, and (2) an additional gel extraction of the amplified fragments. The two-step PCR protocols (Table 8, set forth in FIG. 20) employs two different annealing temperatures, in a first step the annealing temperature of solely the overlapping part with the initial coding polynucleotide sequence (8) is used, while in a second step the annealing temperature of both the overlapping part with the initial coding polynucleotide sequence (8) and the terminal sequences (16, 17) is used. The more stringent conditions of the second step reduce the formed amount of primer dimers. The second optimization is the use of gel extraction (e.g. with a commercial kit such as the Genejet Gel extraction kit of Thermo Scientific) to fully remove the primer dimers and to selectively purify amplicons with the correct length, excluding the much smaller primer dimers. These optimization have resulted in a protocol for Tile construction with an efficiency of more than 95%.

Example 7: 2-Step Assembly

In a different protocol the approach from the previous examples was further elaborated to the simultaneous cloning of multiple coding polynucleotide sequences into one Tile. Herein the respective coding polynucleotide sequences are created analogous to example 3 to 5, and cloned in the receiving vector using the same protocol. In contrast to cloning of one coding polynucleotide as a Tile, simultaneous cloning of multiple coding polynucleotide sequences requires the addition of different terminal sequences which ensure assembly in the correct order as well as efficient cloning in the receiving vector.

Herein the first coding polynucleotide contains the following parts in their respective order: tail sequence, an inwards oriented second type IIs recognition site, spacer sequence, an inwards oriented first type IIs recognition site, a correct coding extension sequence, the first fragment initial coding polynucleotide sequence, a coding extension sequence complementary to the second fragment, an inwards oriented second type IIs restriction site and a tail sequence. The following coding polynucleotide sequence consist of a tail sequence, an inwards oriented second type IIs restriction site, a coding extension sequence complementary to the first fragment, the initial coding polynucleotide sequence, a coding extension sequence complementary to the following fragment, an inwards oriented second type IIs recognition site and a tail sequence. The order and different parts of the following coding fragments is analogous to the previous fragment only differing in their coding extension sequence. The last fragments consists of the following parts in their respective order: a tail sequence, a second inwards oriented type IIs recognition site, a coding extension sequence complementary to the previous fragment, the initial coding polynucleotide sequence, coding extension sequence, the inwards oriented first type IIs recognition site, a spacer sequence, an inwards oriented second type IIs recognition site and a tail sequence. Herein the different coding extension sequences must be complementary between two adjacent initial coding polynucleotide sequences. They can either be chosen as a part of one of the initial coding polynucleotide sequences hereby resulting in a scar-less assembly or they can be selected as such that they add a minimum of three nucleotides in between the respective initial coding polynucleotide sequences. Finally, this Tile thus comprises different subfragments that are assembled, and can be used itself in a second assembly with other Tiles in a rational, semi-random or random way.

This was tested for the assembly of two subfragments into one Tile in the pVTSEII. The efficiency of cloning was comparable to the efficiency of VersaTile Cloning of a single fragment, and VersaTile shuffling, and was over 95%. This 2-step method is particularly interesting for the assembly of larger gene products and for the generation of Tile libraries that can be used for VersaTile shuffling.

Example 8A: Optimization VersaTile Shuffling Protocol

As a modification to examples 5-6 (rational, semi-random, random) the protocol for VersaTile Shuffling was optimized in terms of time as well as cost. A range of different conditions were tested, herein the number of cycles, amount of ligase and BsaI were varied. These experiments have led to a new and optimized protocol wherein the time needed and the amount of enzyme used are twofold reduced compared to the original protocol. A distinction can be made for the optimization of the rational protocol (Table 9, set forth in FIG. 21) where only one correct clone is needed, and the semi-random and random protocol (Table 10, set forth in FIG. 22) where the variation needs to be maintained as high as possible. Therefore, the rational protocol has more stringent conditions compared to the semi-random and random protocols.

Example 8B: Construction of a Versatile Set of Destination Vectors with Different Promotors and Purification Tags The destination vector serves as an expression and assembly vector for the final construct created by VersaTile shuffling. The availability of a versatile set of destination vectors enables the experimenter to easily adjust the expression system for the respective protein. This circumvents problems paired with conventional cloning while allowing for an easy way to screen for the optimal expression system in terms of protein expression, purification, stability and solubility. Nine destination vectors based on the pNIC28-BsaI backbone were constructed (FIG. 5). Herein the promotor, N-terminal tag, negative selection marker and C-terminal tag are considered modules that are interchangeable between different vector backbones (FIG. 5). The nine destination vectors contain the kanamycin resistance gene, and the SacB module for negative selection.

Construction of the pVTSDs starting from the pNIC28-Bsa4 vector was done by linearizing the pNIC28-Bsa4 vector, followed by amplification and purification of the respective vector components (e.g., promotor, SacB, tags) with modified primers. The primers were designed in such a manner that by using standard restriction ligation protocols the respective modules and the vector backbone are concatenated in a directional manner, generating the new pVTSDx. For these destination vectors conventional type IIp restriction enzymes were used, however, for a more efficient production type IIs restriction enzymes could be employed. This was confirmed by the generation of a new destination vector (pVTSD4) wherein the SacB module was inserted and the ampicillin resistance marker was exchanged for a kanamycin resistance marker. Given the efficiency of this assembly, type IIs restriction enzymes are a convenient tool for the production and custom assembly of vectors.

The composition of a destination vector compatible with VersaTile shuffling is not limited to the modules (promotor, selection marker, tag) used in these examples. Any vector backbone, promotor (inducible, constitutive, tissue specific, . . . ), negative selection marker (e.g., rpsL, ccdB, URA3, tetAR, . . . ), and N- or C-terminal tag (e.g., GST, MBP, FLAG, . . . ) can be used to design a tailor made destination vector compatible with VersaTile shuffling.

Example 9: VersaTile Shuffling Reaction for Rational or Directed Assemblies of Four Tiles In order to further expand the possibilities of VersaTile shuffling in terms of the number of positions, a system with four Tiles was designed. The following example only includes, but is not limited to engineered endolysins. These modified bacteriophage derived enzymes can be separated into four modules. Creation of a repository, according to example 3, consisting of Tile vectors specific for engineered endolysins (peptides, linkers, enzymatically active domains, and cell wall binding domains) enables an easy selection and assembly of any rationally designed engineered endolysin.

The efficiency of the VersaTile shuffling method was assessed based on the rational design of 96 different engineered endolysins in parallel. These 96 engineered endolysins where designed based on information found in literature with the goal of improving their antibacterial activity and salt resistance. The first step is to pipet all four corresponding Tiles in each well of a multi-well PCR plate together with the destination vector (pVTSD3 in this case), BsaI and T4 DNA ligase followed by the VersaTile reaction as depicted in Tables 11 & 12 (set forth in FIGS. 23-24). Subsequently, *E. coli* BL21(DE3)pLysS competent cells were transformed with the reaction mix and plated on selective medium (Kan$^{50}$ and 5% sucrose). The competent cells were prepared beforehand (rubium chloride method) and stored in a multi-well plate to simplify the transformation step and to keep the 96 engineered endolysins arrayed. Plating was done on a Q-tray plate, a more time efficient alternative to 96 separate petri dishes. Each plate consists of 48 wells in which the respective cultures were inoculated. After overnight incubation, the Q-trays showed an abundance of colonies for 95 out of 96 constructs, indicating the VersaTile reaction was successful. A clone analysis was performed for further confirmation on both a single colony for every construct as well as on the respective purified plasmid DNA of those constructs. As a consequence of the rational design the expected base pair length of the resulting engineered endolysin constructs could be calculated and compared to the obtained lengths of the colony PCRs analyzed by gel electrophoresis. 90 out of 95 clones showed a band with a correct length, thus indicating a 95.7% efficiency. Moreover, nine positive clones and one negative clone were sequenced. All nine positive clones showed a correct assembly of the Tiles. The sequenced negative clone had a wrong order and composition of Tiles, which is most likely due to errors during pipetting of the Tiles in preparation of the VersaTile reaction.

In summary, the results indicate the VersaTile reaction with four Tiles is very efficient, even on a multi-well scale. Compared to the conventional creation of recombinant assemblies comprising four fragments of different origin, the use of a repository immensely simplifies the process. A repository in combination with the arraying in a multi-well format has allowed us to reduce the time required to just three days, hereby emphasizing the potential of the VersaTile format for the high-throughput generation of DNA assemblies of Tiles with no sequence similarity.

Example 10: VersaTile Shuffling Reaction for Semi-Random Assemblies of Four Tiles In a different protocol VersaTile shuffling is employed to semi-randomly generate a large number of engineered endolysins. Semi-random design implies that for at least one position more than one Tile is selected from the repository. On the other positions only one Tile can be selected. Herein the variation of the generated constructs is increased in contrast to rational design (example 9).

To assess the semi-random properties of VersaTile shuffling, the following experiment was set up: 24 outer membrane permeabilizing peptides at position 1, one linker at position 2, four cell wall binding domains at position 3 and 13 enzymatically active domains at position 4. This creates 1248 different possibilities. The selected Tiles were mixed together with the VersaTile reaction mixture and assembled according to the VersaTile protocol (Tables 11 & 12, set forth in FIG. 23-24).

In order to control if all Tiles are built-in in an evenly distributed manner, chemically competent *E. coli* Top10 cells were transformed with the semi-rationally shuffled VersaTile reaction mixture and plated on LB with kanamycin ($Kan^{50}$) and sucrose (5%). 192 colonies were picked up and assessed with a colony PCR followed by agarose gel electrophoresis in order to observe the length distribution of the different assembled products. The bands were manually counted and the lengths were estimated using DNA ladders (Phage Lambda (Psti) and GeneRuler 100 bp DNA ladder). The clones were divided in different groups according to their length (e.g. 1000-1100 bp). The proportion of every group was calculated and plotted with the theoretical length distribution curve calculated with R (statistic software, www.r-project.org) (FIG. 6).

The length distribution of semi-randomly shuffled assemblies does not show significant differences between the theoretical and the experimental data, as both graphs are almost overlapping. The experimental data contained assembled products of every length category. The assembly reaction was performed twice and each time 25 clones were sequenced to assess if the assembled products were correct. None of the clones showed mistakes in the assembled products, demonstrating that VersaTile shuffling assembles the end product in the correct manner with high efficiency. 48 of the 50 obtained sequences were different to each other, confirming that the assembled products are indeed mainly randomly produced. (FIG. 7).

Example 11: VersaTile Shuffling Reaction for Random Assemblies of Four Tiles

In another protocol the feasibility of VersaTile shuffling for the random assembly of Tiles was assessed. Random shuffling means that for every position more than one Tile is selected. This is comparable to example 6, however, random shuffling entails a much larger variety compared to semi-random shuffling.

To determine if VersaTile shuffling will assemble the different Tiles in a random manner, the following experiment was set up: four Tiles with a clear difference in length and present in every pVTSE were selected. Thus, each Tile is present at every position (1, 2, 3 or 4), creating 256 ($4^4$) different possibilities. Due to the larger differences in length between the Tiles, they are brought to equimolar concentration. This is done by setting a concentration of 50 ng/μL for peptide 12, the ideal concentration of a Tile. The required concentrations of the other Tiles were calculated using the following equation:

$$\frac{50\text{ ng}}{\mu\text{L}} \times \frac{\text{length of } pVTSE \text{ and Tile}}{\text{length of } pVTSE \text{ with peptide 12}} = \text{equimolar concentration of Tile}$$

The required amount of every Tile in the four mixtures is taken and the four mixtures are prepared. The concentration of the mixtures is measured with the NanoDrop 2000 and, when necessary, diluted to 50 ng/μL. Afterwards these mixtures are put together and shuffled according to the VersaTile shuffling protocol (Tables 11 & 12, FIGS. 23-24). To assess the length of the assemblies, clone analysis is performed on 192 colonies of which 25 samples are sent for sequencing.

189 of the 192 picked up colonies gave a visible band on an agarose gel. These bands are manually counted and the lengths are estimated in order to determine the respective length distribution of the randomly shuffled Tiles. Analogous to example 6 all clones are divided in different groups according to their length. The proportion of every group was calculated and plotted with the theoretical distribution curve calculated with R (FIG. 8).

The graphs of the theoretical expectation and the experimental data correlate well for each category. It can be concluded that VersaTile shuffling can be used to do random shuffling and that short, intermediate or long Tiles are integrated with close to similar preference.

To verify if the assembled products do not contain any mutations in the Tiles or in the coding extension sequences, 25 samples were sequenced (mentioned above). All assemblies were correct, e.g. the number of Tiles was four, coding extension sequences were correct, the Tiles do not have mutations, etc. This confirms that VersaTile shuffling assembles the end product in a correct manner with high efficiency. In addition, 23 of the 25 obtained sequences were different to each other, indicating that the assembled products are indeed mainly randomly produced.

Example 12: VersaTile Shuffling Reaction in Different Destination Vectors (Including for Expression in Other Hosts than *Escherichia coli*)

A major asset to the use of VersaTile shuffling is the interchangeability of the destination vectors. Any vector can be easily made compatible with the VersaTile shuffling technique. This entails a broad range of options in terms of expression organism and system (e.g., promotors, purification tags, . . . ) hereby contributing to the versatility of this technique. Initial validation for the use of different pVTSDs was done in *E. coli*. Nine differing pVTSDs (pVTSD1-pVTSD9, i.e. SEQ ID No 13-SEQ ID No 21) (depicted in FIG. 5) were generated and employed for the shuffling of a set of recombinant proteins (e.g. engineered endolysins, GFP, carbohydrate degrading enzymes) as explained in example 9-11, 13, 14 and 17. Analysis of the generated constructs confirmed that the high efficiency of the VersaTile shuffling reaction is preserved independently from the pVTSDs composition. Furthermore expression and purification of a VersaTile shuffled recombinant protein in each of the nine generated pVTSDs has shown that these all work.

These results imply that the range of possible pVTSDs is not limited to the nine generated in example 4, and that any *E. coli* expression system can easily be made compatible with VersaTile shuffling.

In a different protocol, two new destination vectors were constructed for expression in a different host (FIG. 9, *Lactococcus lactis* and *Pichia pastoris*). Analogous to the examples in *E. coli* both destination vectors were validated in their respective host organism. pLVTSD (SEQ ID No 12) was constructed specific for protein expression in *Lactococcus lactis*. In contrast to the general lay-out of the VTS destination vectors, the SacB negative selection marker was not included in pLVTSD as expression of SacB is not toxic for *L. lactis*. The usp45 signal peptide present at the N-terminus of the VersaTile shuffled protein ensures that the expressed recombinant protein is secreted by *L. lactis*.

The same was done for pYVTSD (SEQ ID No 11) in *P. pastoris*. VTS as well as protein expression with this destination vector in *P. pastoris* was as efficient as in *E. coli* and *L. lactis*. These examples confirm that VersaTile shuffling is limited neither to a fixed pVTSD lay-out or to a host organism. Confirmation in *E. coli*, L. *Lactis* and *Pichia pastoris* implies this method can be used in a diverse range of expression hosts (bacterial, eukaryotic) and destination vectors.

Example 13: VersaTile Shuffling Reaction with Different Coding Extension Sequences VTS is not limited to the coding extension sequences used in the previous examples. In theory any coding nucleotide sequences (multiple of 3 nucleotides) can be chosen to function as coding extension sequence. Herein the coding extension sequences are conserved nucleotides linking the different Tiles together, they are sequence independent and could be designed to fit the experimenters specific needs. However, the amino acids for which the nucleotides present in the coding extension sequence encode, need to be taken into account on a protein level. Different amino acids have different structures, meaning they can be larger, smaller, flexible or more rigid. These parameters play an important role in the modular assembly of proteins in terms of maintaining their cooperative protein-protein interactions, folding, structure, activity and stability. In order to confirm this, systems with different coding extension sequences were designed and tested (see Table 1). Similar DNA assembly efficiencies were obtained irrespective the specific coding extension sequences used.

Example 14: VersaTile Shuffling Reaction with One Position Occupied by a Mutagenized Library of Tile Vectors Comprising Mutagenized Variants of a Given Initial Coding Polynucleotide Sequence In this protocol the versatility of VersaTile shuffling was further expanded to the use of a repository of mutagenized Tiles. By means of random or rational mutagenesis the variation present in a Tile repository can be further expanded. Thus, the combination of the VersaTile shuffling method with mutagenesis techniques creates the possibility to produce an unprecedented variation that can be utilized for the directed evolution of proteins when supplemented with an adequate screening method. In this example a mutagenized repository of one Tile, generated by error prone PCR, was directly used in a VersaTile reaction to assess its feasibility.

The error prone PCR protocol is depicted in Table 13 (set forth in FIG. 25) and was employed to mutagenize the complete KZ144 endolysin Tile. Following the amplification step the resulting amplicon was controlled using agarose gel electrophoresis and subsequently purified. The purified fragments contained the necessary parts (tail sequence, first type IIs recognition sequence and coding extension sequence) so that they could be used directly for VersaTile shuffling. The VersaTile reaction was done as shown in example 5 using peptide 1 on position one, linker 1 on position two and the mutagenized library of the KZ144 endolysin on position 3. *E. coli* competent cells were transformed with the complete VTS mix and plated on selective medium (kanamycin, sucrose). This resulted in an abundance of colonies, indicating the use of mutagenized Tiles does not affect the efficiency of the VersaTile method. Clone analysis of 192 colonies further confirmed this as the majority (74%) showed a correct migration pattern on an agarose gel. Five samples were sent for sequencing in order to validate that mutations are present. All five samples contained mutations in the KZ144 endolysin Tile of which most were substitutions, hereby confirming that VersaTile shuffling is compatible with mutagenesis without any reduction in efficiency. In addition to directly using the mutagenized PCR products for shuffling, a plasmid library of mutants can also be created by cloning these mutagenized fragments in a pVTSE receiving vector. Therefore, the respective sequences can be amplified using tailed primers (tail sequence, second type IIs recognition site, spacer sequence, first type IIs recognition sequence, coding extension sequence) (FIG. 13) either under error prone conditions, or using a previously mutagenized library of the respective sequence as a template. Due to the efficiency of the type IIs cloning in both pVTSEII & pVTSEIII the variation created in the amplification step is conserved during cloning in the pVTSE, hereby creating a plasmid library which can easily be replicated and used for shuffling. This was confirmed by using a mutagenized library of the therminator DNA polymerase as a template to generate a Tile. Sequencing of the shuffled products resulting from shuffling with the respective Tile confirms that the initial variation of the mutagenized library was conserved during Tile creation.

Example 15: VersaTile Shuffling Reaction with Two Positions Occupied by Sequences Originating from Two Different Libraries of Tile Vectors Each Comprising Mutagenized Variants of a Given Initial Coding Polynucleotide Sequence As an expansion of example 10 two positions in the VersaTile reaction were occupied by a library of mutagenized Tiles. The KZ144 endolysin was divided into two Tiles, KZ144 CBD and KZ144 EAD, which were both submitted to an error prone PCR (Table 13, FIG. 25) to generate two separate libraries of mutagenized Tiles. The protocol used for VTS is completely analogous to example 14.

After transformation of the respective VTS mixture an abundance of colonies was visible. 24 clones were analysed of which 18 showed a correct pattern after clone analysis, and 6 out of 6 sequenced clones contained the correct construct. In all sequenced clones mutations in the two mutagenized Tiles were present.

Both example 14 and 15 indicate that a repository of mutagenized Tiles can easily be combined with the VersaTile shuffling technique, suggesting that mutagenesis can be applied to all used Tiles. In these examples mutagenesis of the Tiles was limited to error prone PCR, however other mutagenesis techniques (e.g., site-directed mutagenesis) could be employed to generate a mutagenized Tile repository. This immensely adds to the versatility of the VTS method as a combination of mutagenesis with DNA shuffling creates an enormous reservoir of protein variation, which can be tapped for proteins with desired functions and properties.

Example 16: VersaTile Shuffling Reaction Using a Different Type IIs Restriction Enzyme (other than BsaI)

In the previous examples BsaI was used for the VTS reaction. However VTS is not limited to BsaI and other type IIs restriction enzymes (Table 5) could also be employed. However, the destination vector should be adjusted to the respective type IIs restriction enzyme.

To confirm this we did a VTS reaction with BfuAI (Table 5). Four Tiles were generated using tail bearing primers. The primer tails contained a part complementary to the initial coding polynucleotide sequence, coding extension sequence and the BfuAI recognition site respectively (first type IIs recognition site). The resulting PCR products were purified and immediately used in a VTS reaction where the pVTSEIII functioned as a destination vector. pVTSEIII could be used as destination vector because of the presence of the BfuAI recognition sites in the multiple cloning site in the correct order and orientation, flanking a negative selection marker. Therefore, this experiment also indicates that pVTSEII and pVTSEIII can be used to assemble shuffled fragments. Transformation of the VTS reaction mixture resulted in an abundance of colonies of which the majority (92%) showed the correct pattern after clone analysis. Moreover four sequenced clones all contained a perfectly concatenated sequence.

To add to this example we also did a VTS reaction using SapI (Table 5). SapI in contrast to BfuAI and BsaI generates a 3 nucleotide overhang, but has the advantage that it has a recognition site of 7 nucleotides. VTS assembly of four Tiles using the SapI restriction enzyme was analogous to VTS with BfuAI and BsaI. There was no reduction in efficiency indicating that a 3 nucleotide overhang is sufficient for a correct assembly. However, a reduced number of coding extension sequences compared to a 4 nucleotide overhang has to be taken into account.

The successful use of different type IIs restriction enzymes, including ones with different cutting characteristics, demonstrate that VTS is not limited to BsaI. A whole range of type IIs restriction enzymes can be employed for VTS, making it possible for the experimenter to select the type IIs restriction enzyme based on the absence of its recognition site in the respective Tiles. Although this makes VTS more versatile, it has to be taken into account that for each type IIs restriction enzyme a compatible destination vector has to be created.

Example 17: Hybrid of VersaTile Shuffling and Golden Gate Shuffling with the Selection of Coding Extension Sequences which are Either Conserved Nucleotides (Golden Gate Shuffling) or Additional Nucleotides Encoding a Linker Between Two Adjacent Modules (VersaTile Shuffling)

This experiment was set up to validate that both conserved and freely chosen nucleotides can be used simultaneously during the VTS reaction. This enables scar-less shuffling of homologous and non-homologous parts (conserved nucleotides as coding extension sequences) while also allowing non-homologous parts (added nucleotides as coding extension sequence) linked by a set of selected coding extension sequences to be shuffled simultaneously.

The first example includes the Therminator DNA polymerase and loop structure of the 929 DNA polymerase. Therminator was divided into seven Tiles based on homologous regions present in the different variants, and conserved nucleotides were selected to function as coding extension sequences. However, the 929 DNA polymerase shows little or no homology with Terminator, thus to introduce this loop structure six additional nucleotides were selected to function as coding extension sequences linking the non-homologous loop structure of φ29 to the palm and finger domains of the Therminator DNA polymerase. This enables simultaneous (homologous) shuffling of Therminator DNA polymerase while allowing for an easy introduction of the φ29 loop structure. Introduction of non-homologous parts could drastically change the DNA polymerases activity, specificity and processivity compared to what can be achieved by solely using homologous DNA shuffling. Analogues to the example described above, all analyzed clones had the correct sequence.

The second example consists of an engineered endolysin divided into 5 Tiles. Four Tiles (pep46, Link2, CBD3 and EAD11) constitute the engineered endolysin coding sequence and are assembled in a scar-less manner (coding extension sequence is part of the adjacent Tile coding sequence). The fifth Tile is a purification tag (e.g. Strep, His, GST, . . . ), and is linked to the engineered endolysin by 6 carefully selected nucleotides coding for 2 extra amino acids. This experiment was done with the purification tag at the N- as well as the C-terminus of the engineered endolysin. The addition of a purification tag as an extra Tile entails a great deal of versatility since it enables the experimenter to choose the used purification method with respect to the recombinant protein. The use of both conserved nucleotides and freely chosen coding extension sequences is as efficient as the conventional Versatile reaction. This was confirmed by clone analysis on 8 clones which all showed the correct length, and sequencing of 2 clones which both had a correct sequence.

Example 18: Purification and Analysis of Proteins Produced with VersaTile Shuffling Key to this technique is the use of additional nucleotide linkers between the different modules as this render VTS a universal shuffling method, including both homologous and non-homologous sequences. The extra nucleotides, on a protein level, result in the addition of extra amino acids between the modules. To validate VTS on a protein level in addition to determining the effect of the extra amino acid linkers on the resulting protein, expression, purification and screening of several VTS generated proteins was performed. In addition to example 8B, where expression of active VTS generated proteins in *L. lactis* was already shown, both large (500 mL) and small scale (96-well) expression of several VTS generated proteins was performed in *E. coli.*

An engineered endolysin consisting of peptide 1 on position one, CBD1 on position two and three, and EAD12 on position four was expressed in 500 mL lysogenic broth containing kanamycin and was purified using the HisGraviTrap column (GE Healthcare). FIG. 10 shows a clear expression of the respective protein, moreover the amount of protein produced was the same as for similar proteins generated by conventional cloning methods. In addition, an enzymatic and antibacterial assay showed that the VTS created protein was functionally active.

In a different protocol 96 different VTS generated proteins were expressed, purified and screened in parallel. BL21-codon plus(DE3)-RIL cells were transformed with the respective plasmids and inoculated in auto-induction medium in an arrayed manner (96-well). The cultures were incubated at 37° C. for 5 hours followed by 24 hours at 16° C. Purification was done using a commercial kit for his-tag purification on a multi-well scale (HisPur™ Ni-NTA spin plate from Thermo Scientific). The protein yield is visualized on SDS-PAGE (FIG. 11). Moreover enzymatic and antibacterial assays showed that the majority of the VTS generated proteins was active.

Both the large scale and small scale expression yielded active proteins, hereby validating the usefulness of VersaTile shuffling on a protein level. The extra amino acid linkers between the protein modules do not abolish the proteins tertiary structure, its ability to be expressed or its activity, rendering VTS a promising method for the production of new recombinant proteins.

Example 19: VersaTile Shuffling for Scar-Less Assembly. Coding Extension Sequences are Chosen as Such that they Allow a Scar-Less Assembly. This Requires for Every Assembly Coding Extension Sequences have to be Taken Dependent on the Sequence Termini of the Adjacent Tiles A major advantage of the VTS method is that it can be used to shuffle an unprecedented amount of modules independently on their sequence homology. However, in some cases the introduction of extra amino acid between the different protein parts could be undesired. In these cases VTS could also be used, however, the coding extension sequences need to be adjusted and selected specifically for each envisioned assembly. The selected coding extension sequence flanking a Tile should be identical to the starting (or ending) nucleotides of the following (or preceding) Tile sequence. As such, scar-less assembly can be achieved as there are no intervening nucleotides added in between two adjacent Tiles. However, in contrast to the universal character of conventional VersaTile shuffling, scar-less assembly implies that for each specific assembly a new set of coding extension sequences needs to be designed, eliminating the possibility for random or combinatorial shuffling.

In this protocol three Tiles (peptide 1, CBD6 and EAD9) were shuffled in such a manner that their assembly is scar-less. The coding extension sequences were selected to be a part of the coding sequence of the preceding Tile. The efficiency of the assembly was analogous to example 5-7. Besides scar-less assembly, this method could also be employed for site directed mutagenesis. Herein point mutations can be introduced in the primers of the Tiles in such a manner that after concatenation of the different Tiles a mutation is introduced at a predefined location in the respective coding polynucleotide sequence.

The invention claimed is:

1. A method for preparing a Tile vector comprising a selectable marker and a coding polynucleotide sequence immediately preceded and followed by a type IIs recognition sequence, wherein the preceding and following recognition sequences are recognized by a same type IIs restriction enzyme, but have an opposite orientation, wherein the Tile vector can be cleaved using a type IIs restriction enzyme recognizing the preceding and following recognition sites resulting in the release of the coding polynucleotide sequence having at its respective ends known overhang sequences, the released coding polynucleotide sequence lacking the preceding and following type IIs recognition sequences;

the method comprising:

a) providing an initial coding polynucleotide and extending the respective ends of the polynucleotide with first and second terminal sequences wherein each of the terminal sequences comprises:

i. a coding extension sequence consisting of one or more sets of three nucleotides, which is added adjacent to the respective end of and in frame with the open reading frame of the initial coding polynucleotide;

ii. a first type IIs recognition sequence adjacent to the coding extension sequence wherein the first recognition sequence is oriented such that a type IIs restriction enzyme recognizing the first recognition site can cleave within the coding extension sequence generating an overhang and wherein the first type IIs recognition sequences of the first and second terminal sequences are recognized by a same type IIs enzyme, but have an opposite orientation;

iii. a spacer sequence adjacent to or within the first type IIs recognition sequence;

iv. a second type IIs recognition sequence adjacent to the spacer sequence wherein the second recognition sequence is oriented such that a type IIs restriction enzyme recognizing the second recognition sequence can cleave the spacer sequence to generate a spacer overhang and wherein the second type IIs recognition sequence is not recognized by a type IIs enzyme recognizing the first type IIs recognition sequence;

v. a tail sequence of sufficient length in order to allow binding of a type IIs restriction enzyme to the second recognition sequence;

b) providing a receiving vector comprising a first nucleotide sequence comprising a selectable marker positioned between first and second type IIs recognition sequences, such that the vector can be cleaved using type IIs recognition enzymes recognizing the first and second type IIs recognition sequences to form:

i. a stuffer sequence comprising the first and second type IIs recognition sequences; and ii. a selectable vector fragment comprising the selectable marker but lacking the first and second type IIs recognition sequences and having non-complementary terminal overhangs, wherein one overhang is complementary to the spacer overhang obtained after cleaving the first terminal sequence using a type IIs recognition enzyme recognizing the second type IIs recognition sequence of the first terminal sequence, while the other overhang sequence is complementary to the spacer overhang obtained by cleaving the second terminal sequence using a type IIs restriction enzyme recognizing the second type IIs recognition sequence of the second terminal sequence; and c) incubating a mixture, wherein the mixture comprises:

i. an extended initial coding polynucleotide of a);

ii. a receiving vector of b);

iii. type IIs restriction enzymes recognizing the second type IIs recognition sequences of the terminal sequences of the extended initial coding polynucleotide;

iv. type IIs restriction enzymes recognizing the first and second type IIs recognition sequences of the receiving vector; and v. a DNA ligase.

2. The method according to claim 1, wherein the stuffer fragment of the receiving vector comprises a counter-selectable marker.

3. The method according to claim 1, wherein the second type IIs recognition sequences of the first and second terminal sequences of the extended polynucleotide are recognized by a same type IIs enzyme.

4. The method according to claim 3, wherein the first and second type IIs recognition sequences of the receiving vector are recognized by a same type IIs enzyme, but have an opposite orientation.

5. The method according to claim 4, wherein the first and second type IIs recognition sequences of the receiving vector are recognized by the same type IIs enzyme as the second type IIs recognition sequences of the first and second terminal sequences of the extended initial coding polynucleotide.

6. The method according to claim 5, wherein the receiving vector comprises two multiple cloning sites, a first multiple cloning site comprising a succession of multiple different type IIs recognition sequences and a second multiple cloning site comprising oppositely oriented type IIs recognition sequences recognized by the same type IIs enzymes as those in the first multiple cloning site, wherein the multiple cloning sites comprise the first and second type IIs recognition sequences of the receiving vector, which are recognized by a same type IIs enzyme as the second type IIs recognition sequences of the first and second terminal sequences of the extended initial coding polynucleotide.

7. The method according to claim 1, wherein the initial coding polynucleotide is extended with the terminal sequences using a polymerase chain reaction (PCR), wherein the PCR involves the use of tailed forward and reverse primers annealing on the respective ends of the initial coding polynucleotide, wherein the tail of the forward primer adds the first terminal sequence and the tail of the reverse primer adds the second terminal sequence.

8. The method according to claim 7, wherein the PCR is an error prone PCR thus generating a multitude of vectors, which vary from one another in that they comprise random mutants of the initial coding polynucleotide.

9. The method according to claim 1, wherein the method further comprises a directed mutation in the sequence of the initial coding polynucleotide in the Tile vector via the Kunkel method, PCR site-directed mutagenesis with mismatch primers, or a whole plasmid mutagenesis method.

* * * * *